(12) United States Patent
Pauli et al.

(10) Patent No.: US 6,309,857 B1
(45) Date of Patent: Oct. 30, 2001

(54) NUCLEOTIDE SEQUENCES ENCODING MAMMALIAN CALCIUM ACTIVATED CHLORIDE CHANNEL-ADHESION MOLECULES

(75) Inventors: Benedicht U. Pauli, Brooktondale; Randolph C. Elble, Ithaca, both of NY (US); Achim D. Gruber, Hanover (DE)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/193,562

(22) Filed: Nov. 17, 1998

Related U.S. Application Data
(60) Provisional application No. 60/065,922, filed on Nov. 17, 1997.

(51) Int. Cl.$^7$ .......................... C07K 14/705; C12N 15/12
(52) U.S. Cl. .................. 435/69.1; 435/252.3; 435/320.1; 530/350; 536/23.5
(58) Field of Search ................................ 435/69.1, 252.3, 435/320.1; 530/350; 536/23.5

(56) References Cited

PUBLICATIONS

Welsh et al. Molecular Mechanisms of CFTR Chloride Channel Dysfunction in Cystic Fibrosis. Cell 73:1251–1254, Jul. 1993.*
Kerem et al. Identification of the Cystic Firrosis Gene: Genetic Analysis. Science 245:1073–1080, Sep. 1989.*

* cited by examiner

Primary Examiner—John Ulm
(74) Attorney, Agent, or Firm—Hodgson Russ LLP

(57) ABSTRACT

Nucleotide sequences which encode a mammalian lung endothelial cell adhesion molecule are disclosed. Also disclosed are nucleotide sequences which encode a lung endothelial cell adhesion molecule-associated protein. Recombinant lung endothelial cell adhesion molecule or recombinant lung endothelial cell adhesion molecule-associated protein may be obtained by culturing in a medium a host cell genetically engineered to contain and express a nucleotide sequence according to the present invention, and recovering the recombinant lung endothelial cell adhesion molecule-associated protein or recombinant lung endothelial cell adhesion molecule-associated protein from the culture medium.

7 Claims, 15 Drawing Sheets a
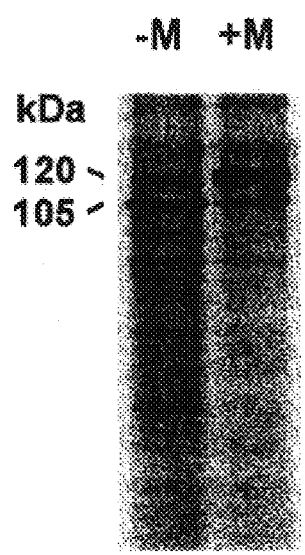
Figure 8
b
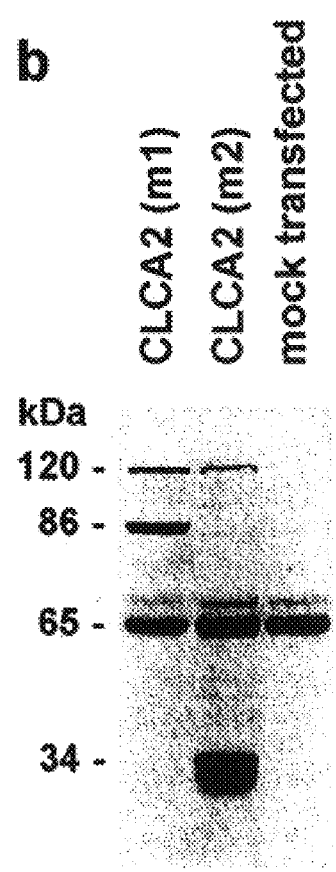

Figure 14

| | Figure 14A |
|---|---|
| | Figure 14B |

```
                 s
h ClCA2     MTQRSIAGPICNLKFVTLLVALSSELPFLGAGVQLQDNGYNGLLIAINPQVPENQNLISNIKEMITEASFYLFNATKRRV  80
h ClCA1     .GPFKSS-----VFILI.HL-.EGA.S--NSLI..NN...E.IVV..D.N...DET..QQ..D.V.Q..L...E..GK.F  72
b ClCA1     .VP.LTV-----IL.L..HL..PG-MK--SSM.N.IN...D.IV......S...DEK..Q......V......T...H....  71
Lu-ECAM-1   .VLCLNV-----IL.L..HL..PG-MK--SSM.N.IN...D.IV......S...DEK..E......V......T...H....  71
m ClCA1     .VPGLQV-----L.L..HL..QN-TE--SSM.H.NS...E.VV......S...DER..PS......V.Q..T...E.SQG...  71
                                                                                          *
h ClCA2     FFRNIKILIPATWKANNN-SKIKQESYEKANVIVTDWYGAHGDDPYTLQYRGCGKEGKYIHFTPNFLLNDNLTAGYGSRG  159
h ClCA1     Y.K.VA....E..TKADYVRP.L.T.KN.D.L.AESTPPGN.E...E.MGN..EK.ER..L..D.IAGKK.AE-..PQ...  151
b ClCA1     Y....VS.....M...SKSEYLMP......DQ.E...ANP.LK.......GR..EK.Q..........TN..PI-.......  150
Lu-ECAM-1   Y....VS.....M...SKSEYFIP......DQ.D...ANP.LKY..........GR..EK...........TN.FHI-.......  150
m ClCA1     Y....S..V.M...SKSEYLMP.R...D...A.PHLQ.........GQ..DR.Q...........T....RI-...P...  150
                *                                                                       *
h ClCA2     RVFVHEWAHLRWGVFDEYNNDKPFYINGQNQIKVTRCSSDITGIFV---CEKGPCPQENCIISK---LFKEGCTFIYNS  232
h ClCA1     KA.............EK..LS-NGR.QAV..AG...TN.V-KK.QG.S.YTKR.TFN.VTG.YEK..E.VLQ.        229
b ClCA1     .A...........I.......G.Q...SRR.T.EA.....TH....TN.IVK-.QG.S.ITRP.RRDSQTG.YEAK...PEK  229
Lu-ECAM-1   .............I......V.Q....SRK.T.EA.....TH....N.VFKK.PG.S.ITSL.RRDSQTG.YEAK...LPKK  230
m ClCA1     .............V.R.......SRK.T.EA.....AS...KK.V-HE.QR.S.VTRA.RRDSKTR.YEPK....PDK  229
               *                                            1
h ClCA2     TQNATASIMFMQSLSSVVEFCNASTHNQEAPNLQNQMCSLRSAWDVITDSADFHHSFPMNGTELPPPTFSLVQAGDKVV  312
h ClCA1     R.TEK.....A.HVD.I...TEQN..K.....K...K.N...T.E..R..E..KKTT..TT--Q..N......L.I.QRI.  307
b ClCA1     S.T.RE......H..T......TEK...V.......K..NGK.T....MN.T..QNTS..TEMNP.TQ.....LKSKQR..  309
Lu-ECAM-1   S.T.KE......P..H..T.....TEK...T.......K..NGK.T....MR.V..QNTS..TEMNP.TH.....LKSKQR..  310
m ClCA1     I.T.G.......N.N.......TENN..A........K..NR..T.....KT.....QNAP..R...A......Y.LKSRRR..  309
                                                               *
h ClCA2     CLVLDVSSKMAEADRLLQLQQAAEFYLMQIVEIHTFVGIASFDSKGEIRAQLHQINSNDDRKLLVSYLPTTVSAKTDISI  392
h ClCA1     ....K.GS..TGN..NR.N..GQLF.L.T...LGSW..MVT...AAHVQSE.I....GS..DT.AKR..AA--..SGGT..  385
b ClCA1     ....K.GS..SSE..FRMN....LF.I..I.KGSL..MVT...VA...IN.TK.TDDNVYENITAN..QE--..NGGT..  387
Lu-ECAM-1   ....K.GS.SAE...F.MN....L..I.VI.KGSL..MVT...VA..QHH.TR.TDDNVYQKITAK..QV--..NGGT..  388
m ClCA1     ....K.GS.DKE...IRMN....L...T.....KESM..LVT...AAH.QNY.IK.T.SS.YQKITAN..QQ--..SGGT..  387
                                                 2
h ClCA2     CSGLKKGFEVVEKLNGKAYGSVMILVTSGDDKLLGNCLPTVLSSGSTIHSIALGSSAAPNLEELSRLTGGLKFFVPDISN  472
h ClCA1     RSA.-T.IRKKYPTD..EIV.L.D.E.NTISG.FNE.KQ..AI..TV...P...QE....KM....QTYAS.QVQ    464
b ClCA1     .R...A..QAIIQSQQSTS..EI..L.D.E.NEIHS.IEE.KQ..VI..T....P....KE..T..DM..HR.YANKDI-  466
Lu-ECAM-1   .R...A..QAIIHSDQSTS..EI..L.D.E.NEINS.FED.KR..AI..T....P....KE..T..NM..YR..ANKDI-  467
m ClCA1     .H..QA..QAITSSDQSTS..EIV.L.D.E.NGIRS.FEA.SR..AI..T....P.R.RE..T..DM..R.YANKDL-  466
```

```
h CLCA2     SNSMIDAFSRISSGTGDIFQQHIQLESTGENVKPHHQLKNTVTVDNTVGNDTMFLVTWQASGPPEIILFDPDGRKYYTNN  552
h CLCA1     N.GL....GAL...N.AVS.RS.....K.LTLQNSQWMNG..I..S...K..L..I...-TTQ..Q.L.W..S.Q.--QGG  541
b CLCA1     -.GLTN.........RS.S.T..T.....KALAITEKKWVNG..P..S.I.....F.V....-TIKK...L.Q..K.K..K.SD  544
Lu-ECAM-1   -TGLTN.........RS.S.T..A.....KALKITGRKRVNG..P..S.......F.V....-TIQK...V.Q..K.K..K.SD  545
m CLCA1     -..L.........TS.SVS..AL....KAFD.RAGAWING..PL.S.......F.VI..-MVKK.....Q..K.K..T.SD  544 h CLCA2     FITN-LTFRTASLWIPGTAKPGHWTYTLNNTHHSLQALKVTVTSRASNSAVPPATVEAFVERDSLHFPHPVMIYANVKQG  631
h CLCA1     .VVDK-NTKM.Y.Q...I..V.T.K.S.---QA.S.T.TL....ATL..I..TSKTNK.TSK..S.LVV...IR..    617
b CLCA1     .KEDK.NIHS.R.R....I.ET.T....S.L.N.A.P.I.T...T.RSPTT..V.AT.HMSQNTA.Y.S..IV..Q.S.  624
Lu-ECAM-1   .KEDK.NI.S.R.Q....I.ET.T....S.L.N.A.S.M.T...T.RSPTI..VIAT.HMSQHTA.Y.S..MIV..Q.S.  625
m CLCA1     .QDDK.NI.S.R.Q....ET.T...SY--.GTKS.LITM...T..RSPTME.LLGYCYMSQSTAQY.SRMIV..R.S..  622 h CLCA2     FYPILNATVTATVEPETGDPVTLRLLDDGAGADVIKNDGIYSRYFFSFAANGRYSLKVHVNHSPSISTPAHSIPGSHAMY  711
h CLCA1     AS...R.S....LI.SVN.KT...E...N....AT.D..V......TTYDT.....V..RALGGVNAARRVIPQQ.G.L.  697
b CLCA1     .L.V.GIN....II.T.D.HQ....E.W.N....TV........TDYRG.........AEARNNTARLSLRQ.QNK.L.  704
Lu-ECAM-1   .L.V.GIS.I.II.T.D.HQ....E.W.N....R.TV........TDYYG.........AQARNNTARLNLRQ.QNKVL.  705
m CLCA1     .L.V.G.N....LI.A.H.HQ....E.W.N....IV......T...TDYHG........R.QAQRNKTRLSLRQ-KNKSL.  701 h CLCA2     VPGYTANGNIQMNAPRKSVGRNEEERKWG-FSRVSSGGSFSVLG-VPAGPHPDVFPPCKIIDLEA-VKVEEELTLSWTAP  788
h CLCA1     I...WIE.DE..W.P..PEINKDDVQH.QVC....T......ASD..NA.I..L...GQ.T..K.EIHGGSLIN.T....  776
b CLCA1     I...IE..K.IL.P..PE.KDDLAKAEIED...LT......T.S.AP.-..N..S.L..N....KF.ED-HIQ......  782
Lu-ECAM-1   I...VE..K.IL.P..PE.KDDLAKA.IED...LT......T.S.AP.P.N..S.....T....KF.ED-YIQ......  784
m CLCA1     I...VE..K.VL.P..PD.QEEAI.ATVED.N...T......T.S.AP.D.D.AR....S.VT....EFIGD-YIH.T..  780 h CLCA2     GEDFDQGQATSYEIRMSKSLQNIQDDFNNAILVNTSKRNPQQAGIREIFTFSPQISTNGPEHQPNGETHESHRIYVAIRA  868
h CLCA1     .D.Y.H.T.HK.I...I.T.ILDLR.K..ESLQ...TALI.KE.NSE.V.L.K.ENI.----FENGTDLFI..Q.    846
b CLCA1     ANVL.K.K.N...I..I....FLDL.K..D..T......SLK.KE...SD.N.E.K.EPFR.----IENGTNF.I.VQ.  852
Lu-ECAM-1   .NVL.K.K.N...I..I....FMDR.E..D..T......NLI.KE...SK.N.E.K.EHFR.----VENGTKF.ISVQ.  854
m CLCA1     .KVL.N.R.HR.I....QHPLDL.E.....T.....A.SLI.KE...SK.A.K.K.ETFK.----IANGIQL.I..Q.   850 h CLCA2     MDRNSLQSAVSNIAQAPLFIPPNSDP-VPARDYLILKGVLTAMGLIGICLLIVVTHHTLSRKKRADKKENGTKLL       943
h CLCA1     V.KVD.K.EI.....RVS.....QTP.ET.SP.---ETSAPCPN.-H.NST.PGIHLKIMW.WIG----LQLSIA     914
b CLCA1     INEAN.T.E......IK.....IK...MP----------------EDSVP.L.-TK.SAINLAIFALAMI------LSIV.  904
Lu-ECAM-1   INEAN.I.E..H.V..IK...LP----------------EDSVHDL.-TK.SEITLAILGLPMI------FSV-F     905
m CLCA1     DNEA..T.E........VKLTSL----------------EDSIS.L.-DD.SAISMTIWGL.VI------FNSI.N    902
```

Figure 14B

```
                        SEQUENCE LISTING

<160> NUMBER OF SEQ ID NOS: 47

<210> SEQ ID NO 1
<211> LENGTH: 3317
<212> TYPE: DNA
<213> ORGANISM: Unknown
<220> FEATURE:
<223> OTHER INFORMATION: sequence encoding Lu-ECAM-1 and Lu-ECAM-1
      associated protein from bovine endothelial cells

<400> SEQUENCE: 1
ggattccagg gtctccagca ttgcctgaat ctggatgtag gtttactgta            50
acatgtgcaa aa atg gtg ctc tgt ctg aat gtt att ctg ttc cta act    98 ttg cat ctc ttg cct gga atg aaa agt tca atg gta aat ttg att     143
```

-continued

```
aac aat ggg tat gat ggc att gtc att gca att aac ccc agt gtg       188
cca gaa gat gaa aaa ctc att gaa aac ata aag gaa atg gta act       233
gaa gct tct act tac ctg ttt cat gcc acc aaa cga aga gtt tat       278
ttc agg aat gtg agc att tta att cca atg acc tgg aaa tca aaa       323
tct gag tac ttc ata cca aaa caa gaa tca tat gac cag gca gat       368
gtc ata gtt gct aat ccc tat cta aaa tat gga gat gat ccc tat       413
aca ctt caa tat gga agg tgt gga gaa aaa gga aaa tat ata cat       458
ttt act cca aac ttc ttg ttg act aat aat ttc cac atc tat ggg       503
tcc cga ggc aga gta ttt gtc cat gag tgg gcc cat ctc cgc tgg       548
gga ata ttt gat gag tat aat gtg gac cag cca ttc tat att tcc       593
aga aag aac act att gaa gca aca aga tgt tca act cat att act       638
ggt att aat gtg gtt ttc aag aaa tgc cct gga ggc agc tgt ata       683
aca agt cta tgc aga cgt gac tca cag aca ggg ctg tat gaa gca       728
aaa tgt aca ttc ctt cca aaa aaa tcc cag act gca aag gaa tcc       773
att atg ttt atg cca agt ctc cat tct gtg act gaa ttt tgt aca       818
gaa aaa aca cac aat aca gaa gct cca aac cta caa aac aaa atg       863
tgc aat ggc aaa agc aca tgg gat gta atc atg aac tct gtt gac       908
ttt cag aat aca tct ccc atg aca gaa atg aat cca ccg act cat       953
cct aca ttt tca ttg ctc aag tcc aaa cag cgg gta gtc tgt ttg       998
gta ctt gat aaa tct gga agc atg tct gca gaa gac cgt ctc ttt      1043
caa atg aat caa gca gca gaa cta tac ttg att caa gtt att gaa      1088
aag gga tct tta gtt ggg atg gtt aca ttt gac agt gtt gct gaa      1133
atc caa aat cat cta aca aga ata act gat gat aat gtt tac caa      1178
aag atc acc gca aaa ctg cct caa gta gct aat ggt gga act tca      1223
att tgt aga ggg ctc aaa gca gga ttc cag gca att atc cac agt      1268
gac cag agt act tct ggt tct gaa atc ata cta tta act gat ggg      1313
gaa gat aat gaa ata aat tca tgc ttt gag gat gta aaa cga agt      1358
ggt gca atc atc cac acc att gct ctg gga ccc tct gct gcc aaa      1403
gaa ctg gag aca ttg tca aat atg aca gga gga tat cgt ttt ttt      1448
gcc aat aaa gac ata act ggc ctt act aat gct ttc agt aga att      1493
tca tct aga agt gga agc atc act cag cag gct att cag ttg gaa      1538
agc aaa gcc ttg aaa att aca gga agg aaa aga gta aac ggc aca      1583
gtg cct gta gac agt aca gtt gga aat gac act ttc ttt gtt gtc      1628
aca tgg aca ata caa aaa cca gaa att gtt ctc caa gat cca aaa      1673
gga aag aaa tat aaa acc tcg gat ttc aaa gaa gat aag tta aat      1718
att cga tct gct cgt ctg caa ata cct ggt att gca gag aca ggt      1763
act tgg act tac agc ctt cta aat aat cat gcc agc tct caa atg      1808
cta aca gtg aca gtg acc act cga gca aga agt cct act ata ccc      1853
cca gta att gca aca gct cac atg agt caa cat aca gca cat tat      1898
```

```
cct agc cca atg att gtt tat gca caa gtc agt caa ggg ttt ttg         1943 cct gta ctg gga atc agt gta ata gcc att ata gaa acc gaa gat         1988 gga cat caa gta aca ttg gag ctc tgg gac aat ggt gca ggt cgt         2033 gat act gtc aag aat gat ggc atc tac tca aga tac ttt aca gat         2078 tac tat gga aat ggt aga tac agt tta aaa gta cat gca cag gca         2123 aga aac aac acg gct agg cta aat tta aga caa cca cag aac aaa         2168 gtt cta tat gtt cca ggc tac gtt gaa aac ggt aaa att ata ctg         2213 aac cca ccc aga cct gaa gtc aaa gat gac ctg gca aaa gct aaa         2258 ata gaa gac ttt agc aga cta acc tct gga ggg tca ttt act gta         2303 tca gga gct cct cct cct ggt aat cac cct tct gtg ttc cca ccc         2348 agt aaa att aca gat ctt gag gct aag ttc aaa gaa gat tat att         2393 caa ctt tca tgg aca gcc cct ggc aat gtc cta gat aaa gga aaa         2438 gcc aac agc tac att ata aga ata agt aag agt ttc atg gat cgt         2483 caa gaa gat ttt gac aat gcg act tta gtg aat act tct aat cta         2528 ata cct aag gag gcc gga tca aaa gaa aat ttt gaa ttt aag cca         2573 gaa cat ttt aga gta gaa aat ggc acc aaa ttc tat att tca gtc         2618 caa gcc atc aac gaa gcc aat ctc atc tca gag gtt tct cac att         2663 gta caa gca atc aaa ttt att cct cta cca gaa gac agt gtc cat         2708 gat ctg ggt acc aag att tct gaa atc act ctg gca att tta gga         2753 tta cca atg att ttc tct gta ttt taaactagga attgtgtcag               2797
cactgataac caatgttata catagttggt acacatttat ttaggattta              2847
attcgctatt ttcttgttct tcagtagcta aattgtgtcc aaccttgcga              2897
ctgcaggact gcagcatgcc aggtttccct gtccatcacc aactcccaga              2947
gcttgctcaa atccatgttc atttgagtca gtaatgctaa ctatctcatc              2997
ctctactgcc ctcttctctg tttaccttca atctttcccc agcattagga              3047
tcttttccaa tgagtcagct cttagcatcg ggtggccaaa atattggcat              3097
tttcagcaac agttcttcaa atgaaatatc cagggtgatt ttctttagga              3147
tagactggtg actgacagtt caagggacac tctggagtct tctccagcac              3197
cgcaccgcag tttgaaagaa ccagttcttt ggtactcagc cttctttata              3247
gtccaatgct cacatctatc atgactcctg gaaaaaccat agctttgaga              3297
aatggatctt tgttgggaaa                                               3317
```

<210> SEQ ID NO 2
<211> LENGTH: 905
<212> TYPE: PRT
<213> ORGANISM: Unknown
<220> FEATURE:
<223> OTHER INFORMATION: Lu-ECAM-1 precursor from bovine endothelial
      cells

<400> SEQUENCE: 2

Met Val Leu Cys Leu Asn Val Ile Leu Phe Leu Thr Leu His Leu
    -20             -15                 -10

Leu Pro Gly Met Lys Ser Ser Met Val Asn Leu Ile Asn Asn Gly
    -5              1               5

-continued

```
Tyr Asp Gly Ile Val Ile Ala Ile Asn Pro Ser Val Pro Glu Asp
 10              15                  20

Glu Lys Leu Ile Glu Asn Ile Lys Glu Met Val Thr Glu Ala Ser
 25              30                  35

Thr Tyr Leu Phe His Ala Thr Lys Arg Arg Val Tyr Phe Arg Asn
 40              45                  50

Val Ser Ile Leu Ile Pro Met Thr Trp Lys Ser Lys Ser Glu Tyr
 55              60                  65

Phe Ile Pro Lys Gln Glu Ser Tyr Asp Gln Ala Asp Val Ile Val
 70              75                  80

Ala Asn Pro Tyr Leu Lys Tyr Gly Asp Asp Pro Tyr Thr Leu Gln
 85              90                  95

Tyr Gly Arg Cys Gly Glu Lys Gly Lys Tyr Ile His Phe Thr Pro
100             105                 110

Asn Phe Leu Leu Thr Asn Asn Phe His Ile Tyr Gly Ser Arg Gly
115             120                 125

Arg Val Phe Val His Glu Trp Ala His Leu Arg Trp Gly Ile Phe
130             135                 140

Asp Glu Tyr Asn Val Asp Gln Pro Phe Tyr Ile Ser Arg Lys Asn
145             150                 155

Thr Ile Glu Ala Thr Arg Cys Ser Thr His Ile Thr Gly Ile Asn
160             165                 170

Val Val Phe Lys Lys Cys Pro Gly Gly Ser Cys Ile Thr Ser Leu
175             180                 185

Cys Arg Arg Asp Ser Gln Thr Gly Leu Tyr Glu Ala Lys Cys Thr
190             195                 200

Phe Leu Pro Lys Lys Ser Gln Thr Ala Lys Glu Ser Ile Met Phe
205             210                 215

Met Pro Ser Leu His Ser Val Thr Glu Phe Cys Thr Glu Lys Thr
220             225                 230

His Asn Thr Glu Ala Pro Asn Leu Gln Asn Lys Met Cys Asn Gly
235             240                 245

Lys Ser Thr Trp Asp Val Ile Met Asn Ser Val Asp Phe Gln Asn
250             255                 260

Thr Ser Pro Met Thr Glu Met Asn Pro Pro Thr His Pro Thr Phe
265             270                 275

Ser Leu Leu Lys Ser Lys Gln Arg Val Val Cys Leu Val Leu Asp
280             285                 290

Lys Ser Gly Ser Met Ser Ala Glu Asp Arg Leu Phe Gln Met Asn
295             300                 305

Gln Ala Ala Glu Leu Tyr Leu Ile Gln Val Ile Glu Lys Gly Ser
310             315                 320

Leu Val Gly Met Val Thr Phe Asp Ser Val Ala Glu Ile Gln Asn
325             330                 335

His Leu Thr Arg Ile Thr Asp Asp Asn Val Tyr Gln Lys Ile Thr
340             345                 350

Ala Lys Leu Pro Gln Val Ala Asn Gly Gly Thr Ser Ile Cys Arg
355             360                 365

Gly Leu Lys Ala Gly Phe Gln Ala Ile Ile His Ser Asp Gln Ser
370             375                 380

Thr Ser Gly Ser Glu Ile Ile Leu Leu Thr Asp Gly Glu Asp Asn
385             390                 395

Glu Ile Asn Ser Cys Phe Glu Asp Val Lys Arg Ser Gly Ala Ile
```

-continued

```
              400                 405                 410

Ile His Thr Ile Ala Leu Gly Pro Ser Ala Ala Lys Glu Leu Glu
415                 420                 425

Thr Lys Ser Asn Met Thr Gly Gly Tyr Arg Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
460                 465                 470

Leu Lys Ile Thr Gly Arg Lys Arg Val Asn Gly Thr Val Pro Val
475                 480                 485

Asp Ser Thr Val Gly Asn Asp Thr Phe Phe Val Val Thr Trp Thr
490                 495                 500

Ile Gln Lys Pro Glu Ile Val Leu Gln Asp Pro Lys Gly Lys Lys
505                 510                 515

Tyr Lys Thr Ser Asp Phe Lys Glu Asp Lys Leu Asn Ile Arg Ser
520                 525                 530

Ala Arg Leu Gln Ile Pro Gly Ile Ala Glu Thr Gly Thr Trp Thr
535                 540                 545

Tyr Ser Leu Leu Asn Asn His Ala Ser Ser Gln Met Leu Thr Val
550                 555                 560

Thr Val Thr Thr Arg Ala Arg Ser Pro Thr Ile Pro Pro Val Ile
565                 570                 575

Ala Thr Ala His Met Ser Gln His Thr Ala His Tyr Pro Ser Pro
580                 585                 590

Met Ile Val Tyr Ala Gln Val Ser Gln Gly Phe Leu Pro Val Leu
595                 600                 605

Gly Ile Ser Val Ile Ala Ile Ile Glu Thr Glu Asp Gly His Gln
610                 615                 620

Val Thr Leu Glu Leu Trp Asp Asn Gly Ala Gly Arg Asp Thr Val
625                 630                 635

Lys Asn Asp Gly Ile Tyr Ser Arg Tyr Phe Thr Asp Tyr Tyr Gly
640                 645                 650

Asn Gly Arg Tyr Ser Leu Lys Val His Ala Gln Ala Arg Asn Asn
655                 660                 665

Thr Ala Arg Leu Asn Leu Arg Gln Pro Gln Asn Lys Val Leu Tyr
670                 675                 680

Val Pro Gly Tyr Val Glu Asn Gly Lys Ile Ile Leu Asn Pro Pro
685                 690                 695

Arg Pro Glu Val Lys Asp Asp Leu Ala Lys Ala Lys Ile Glu Asp
700                 705                 710

Phe Ser Arg Leu Thr Ser Gly Gly Ser Phe Thr Val Ser Gly Ala
715                 720                 725

Pro Pro Pro Gly Asn His Pro Ser Val Phe Pro Pro Ser Lys Ile
730                 735                 740

Thr Asp Leu Glu Ala Lys Phe Lys Glu Asp Tyr Ile Gln Leu Ser
745                 750                 755

Trp Thr Ala Pro Gly Asn Val Leu Asp Lys Gly Lys Ala Asn Ser
760                 765                 770

Tyr Ile Ile Arg Ile Ser Lys Ser Phe Met Asp Arg Gln Glu Asp
775                 780                 785

Phe Asp Asn Ala Thr Leu Val Asn Thr Ser Asn Leu Ile Pro Lys
790                 795                 800
```

-continued

```
Glu Ala Gly Ser Lys Glu Asn Phe Glu Phe Lys Pro Glu His Phe
805                 810                 815

Arg Val Glu Asn Gly Thr Lys Phe Tyr Ile Ser Val Gln Ala Ile
820                 825                 830

Asn Glu Ala Asn Leu Ile Ser Glu Val Ser His Ile Val Gln Ala
835                 840                 845

Ile Lys Phe Ile Pro Leu Pro Glu Asp Ser Val His Asp Leu Gly
850                 855                 860

Thr Lys Ile Ser Glu Ile Thr Leu Ala Ile Leu Gly Leu Pro Met
865                 870                 875

Ile Phe Ser Val Phe
880             884

<210> SEQ ID NO 3
<211> LENGTH: 203
<212> TYPE: PRT
<213> ORGANISM: Unknown
<220> FEATURE:
<223> OTHER INFORMATION: Lu-ECAM-1 associated protein from bovine
      endothelial cells

<400> SEQUENCE: 3

Val Leu Tyr Val Pro Gly Tyr Val Glu Asn Gly Lys Ile Ile Leu
  1               5                  10                  15

Asn Pro Pro Arg Pro Glu Val Lys Asp Asp Leu Ala Lys Ala Lys
                 20                  25                  30

Ile Glu Asp Phe Ser Arg Leu Thr Ser Gly Gly Ser Phe Thr Val
                 35                  40                  45

Ser Gly Ala Pro Pro Gly Asn His Pro Ser Val Phe Pro Pro
                 50                  55                  60

Ser Lys Ile Thr Asp Leu Glu Ala Lys Phe Lys Glu Asp Tyr Ile
                 65                  70                  75

Gln Leu Ser Trp Thr Ala Pro Gly Asn Val Leu Asp Lys Gly Lys
                 80                  85                  90

Ala Asn Ser Tyr Ile Ile Arg Ile Ser Lys Ser Phe Met Asp Arg
                 95                 100                 105

Gln Glu Asp Phe Asp Asn Ala Thr Leu Val Asn Thr Ser Asn Leu
                110                 115                 120

Ile Pro Lys Glu Ala Gly Ser Lys Glu Asn Phe Glu Phe Lys Pro
                125                 130                 135

Glu His Phe Arg Val Glu Asn Gly Thr Lys Phe Tyr Ile Ser Val
                140                 145                 150

Gln Ala Ile Asn Glu Ala Asn Leu Ile Ser Glu Val Ser His Ile
                155                 160                 165

Val Gln Ala Ile Lys Phe Ile Pro Leu Pro Glu Asp Ser Val His
                170                 175                 180

Asp Leu Gly Thr Lys Ile Ser Glu Ile Thr Leu Ala Ile Leu Gly
                185                 190                 195

Leu Pro Met Ile Phe Ser Val Phe
                200             203

<210> SEQ ID NO 4
<211> LENGTH: 26
<212> TYPE: DNA
<213> ORGANISM: Artificial sequence
<220> FEATURE:
<223> OTHER INFORMATION: Amplification primer
```

<400> SEQUENCE: 4
aatttaagcc agaacatttt agagta                26

<210> SEQ ID NO 5
<211> LENGTH: 23
<212> TYPE: DNA
<213> ORGANISM: Artificial sequence
<220> FEATURE:
<223> OTHER INFORMATION: Amplification primer

<400> SEQUENCE: 5
gaaaatggca ccaaattcta tat                23

<210> SEQ ID NO 6
<211> LENGTH: 23
<212> TYPE: DNA
<213> ORGANISM: Artificial sequence
<220> FEATURE:
<223> OTHER INFORMATION: Amplification primer

<400> SEQUENCE: 6
atatagaatt tggtgccatt ttc                23

<210> SEQ ID NO 7
<211> LENGTH: 19
<212> TYPE: DNA
<213> ORGANISM: Artificial sequence
<220> FEATURE:
<223> OTHER INFORMATION: Amplification primer

<400> SEQUENCE: 7
tagaagtatt cactaaagt                19

<210> SEQ ID NO 8
<211> LENGTH: 28
<212> TYPE: DNA
<213> ORGANISM: Artificial Sequence
<220> FEATURE:
<223> OTHER INFORMATION: Amplification primer

<400> SEQUENCE: 8
tactgtctac aggcactgtg ccgtttac                28

<210> SEQ ID NO 9
<211> LENGTH: 18
<212> TYPE: DNA
<213> ORGANISM: Artificial sequence
<220> FEATURE:
<223> OTHER INFORMATION: Amplification primer

<400> SEQUENCE: 9
ggaatatttg atgagtat                18

<210> SEQ ID NO 10
<211> LENGTH: 18
<212> TYPE: DNA
<213> ORGANISM: Artificial sequence
<220> FEATURE:
<223> OTHER INFORMATION: Amplification primer

<400> SEQUENCE: 10
attcatttga aagagacg                18

<210> SEQ ID NO 11

-continued

```
<211> LENGTH: 795
<212> TYPE: PRT
<213> ORGANISM: Unknown
<220> FEATURE:
<223> OTHER INFORMATION: Variant of Lu-ECAM-1 from bovine endothelial
      cells

<400> SEQUENCE: 11

Met Val Leu Cys Leu Asn Val Ile Leu Phe Leu Thr Leu His Leu
    -20                 -15                 -10

Leu Pro Gly Met Lys Ser Ser Met Val Asn Leu Ile Asn Asn Gly
    -5                   1                   5

Tyr Asp Gly Ile Val Ile Ala Ile Asn Pro Ser Val Pro Glu Asp
 10                  15                  20

Glu Lys Leu Ile Glu Asn Ile Lys Glu Met Val Thr Glu Ala Ser
 25                  30                  35

Thr Tyr Leu Phe His Ala Thr Lys Arg Arg Val Tyr Phe Arg Asn
 40                  45                  50

Val Ser Ile Leu Ile Pro Met Thr Trp Lys Ser Lys Ser Glu Tyr
 55                  60                  65

Phe Ile Pro Lys Gln Glu Ser Tyr Asp Gln Ala Asp Val Ile Val
 70                  75                  80

Ala Asn Pro Tyr Leu Lys Tyr Gly Asp Asp Pro Tyr Thr Leu Gln
 85                  90                  95

Tyr Gly Arg Cys Gly Glu Lys Gly Lys Tyr Ile His Phe Thr Pro
100                 105                 110

Asn Phe Leu Leu Thr Asn Asn Phe His Ile Tyr Gly Ser Arg Gly
115                 120                 125

Arg Val Phe Val His Glu Trp Ala His Leu Arg Trp Gly Ile Phe
130                 135                 140

Asp Glu Tyr Asn Val Asp Gln Pro Phe Tyr Ile Ser Arg Lys Asn
145                 150                 155

Thr Ile Glu Ala Thr Arg Cys Ser Thr His Ile Thr Gly Ile Asn
160                 165                 170

Val Val Phe Lys Lys Cys Pro Gly Gly Ser Cys Ile Thr Ser Leu
175                 180                 185

Cys Arg Arg Asp Ser Gln Thr Gly Leu Tyr Glu Ala Lys Cys Thr
190                 195                 200

Phe Leu Pro Lys Lys Ser Gln Thr Ala Lys Glu Ser Ile Met Phe
205                 210                 215

Met Pro Ser Leu His Ser Val Thr Glu Phe Cys Thr Glu Lys Thr
220                 225                 230

His Asn Thr Glu Ala Pro Asn Leu Gln Asn Lys Met Cys Asn Gly
235                 240                 245

Lys Ser Thr Trp Asp Val Ile Met Asn Ser Val Asp Phe Gln Asn
250                 255                 260

Thr Ser Pro Met Thr Glu Met Asn Pro Pro Thr His Pro Thr Phe
265                 270                 275

Ser Leu Leu Lys Ser Lys Gln Arg Val Val Cys Leu Val Leu Asp
280                 285                 290

Lys Ser Gly Ser Met Ser Ala Glu Asp Arg Leu Phe Gln Met Asn
295                 300                 305

Gln Ala Ala Glu Leu Tyr Leu Ile Gln Val Ile Glu Lys Gly Ser
310                 315                 320

Leu Val Gly Met Val Thr Phe Asp Ser Val Ala Glu Ile Gln Asn
```

-continued

```
             325                 330                 335

His Leu Thr Arg Ile Thr Asp Asp Asn Val Tyr Gln Lys Ile Thr
340                 345                 350

Ala Lys Leu Pro Gln Val Ala Asn Gly Gly Thr Ser Ile Cys Arg
355                 360                 365

Gly Leu Lys Ala Gly Phe Gln Ala Ile Ile His Ser Asp Gln Ser
370                 375                 380

Thr Ser Gly Ser Glu Ile Ile Leu Leu Thr Asp Gly Glu Asp Asn
385                 390                 395

Glu Ile Asn Ser Cys Phe Glu Asp Val Lys Arg Ser Gly Ala Ile
400                 405                 410

Ile His Thr Ile Ala Leu Gly Pro Ser Ala Lys Glu Leu Glu
415                 420                 425

Thr Lys Ser Asn Met Thr Gly Gly Tyr Arg Phe Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
460                 465                 470

Leu Lys Ile Thr Gly Arg Lys Arg Val Asn Gly Thr Val Pro Val
475                 480                 485

Asp Ser Thr Val Gly Asn Asp Thr Phe Phe Val Val Thr Trp Thr
490                 495                 500

Ile Gln Lys Pro Glu Ile Val Leu Gln Asp Pro Lys Gly Lys Lys
505                 510                 515

Tyr Lys Thr Ser Asp Phe Lys Glu Asp Lys Leu Asn Ile Arg Ser
520                 525                 530

Ala Arg Leu Gln Ile Pro Gly Ile Ala Glu Thr Gly Thr Trp Thr
535                 540                 545

Tyr Ser Leu Leu Asn Asn His Ala Ser Ser Gln Met Leu Thr Val
550                 555                 560

Thr Val Thr Thr Arg Ala Arg Ser Pro Thr Ile Pro Pro Val Ile
565                 570                 575

Ala Thr Ala His Met Ser Gln His Thr Ala His Tyr Pro Ser Pro
580                 585                 590

Met Ile Val Tyr Ala Gln Val Ser Gln Gly Phe Leu Pro Val Leu
595                 600                 605

Gly Ile Ser Val Ile Ala Ile Ile Glu Thr Glu Asp Gly His Gln
610                 615                 620

Val Thr Leu Glu Leu Trp Asp Asn Gly Ala Gly Arg Asp Thr Val
625                 630                 635

Lys Asn Asp Gly Ile Tyr Ser Arg Tyr Phe Thr Asp Tyr Tyr Gly
640                 645                 650

Asn Gly Arg Tyr Ser Leu Lys Val His Ala Gln Ala Arg Asn Asn
655                 660                 665

Thr Ala Arg Leu Asn Leu Arg Gln Pro Gln Asn Lys Val Leu Tyr
670                 675                 680

Val Pro Gly Tyr Val Glu Asn Gly Lys Ile Ile Leu Asn Pro Pro
685                 690                 695

Arg Pro Glu Val Lys Asp Asp Leu Ala Lys Ala Lys Ile Glu Asp
700                 705                 710

Phe Ser Arg Leu Thr Ser Gly Gly Ser Phe Thr Val Ser Gly Ala
715                 720                 725
```

-continued

```
Pro Pro Pro Gly Asn His Pro Ser Val Phe Pro Pro Ser Lys Ile
730             735                 740

Thr Asp Leu Glu Ala Lys Phe Lys Glu Asp Tyr Ile Gln Leu Ser
745             750                 755

Trp Thr Ala Pro Gly Asn Val Leu Asp Lys Gly Lys Ala Glu Ser
760             765                 770             774

<210> SEQ ID NO 12
<211> LENGTH: 821
<212> TYPE: PRT
<213> ORGANISM: Unknown
<220> FEATURE:
<223> OTHER INFORMATION: Variant of Lu-ECAM-1 from bovine endothelial
      cells

<400> SEQUENCE: 12

Met Val Leu Cys Leu Asn Val Ile Leu Phe Leu Thr Leu His Leu
        -20             -15                 -10

Leu Pro Gly Met Lys Ser Ser Met Val Asn Leu Ile Asn Asn Gly
        -5              1                   5

Tyr Asp Gly Ile Val Ile Ala Ile Asn Pro Ser Val Pro Glu Asp
10              15                  20

Glu Lys Leu Ile Glu Asn Ile Lys Glu Met Val Thr Glu Ala Ser
25              30                  35

Thr Tyr Leu Phe His Ala Thr Lys Arg Arg Val Tyr Phe Arg Asn
40              45                  50

Val Ser Ile Leu Ile Pro Met Thr Trp Lys Ser Lys Ser Glu Tyr
55              60                  65

Phe Ile Pro Lys Gln Glu Ser Tyr Asp Gln Ala Asp Val Ile Val
70              75                  80

Ala Asn Pro Tyr Leu Lys Tyr Gly Asp Asp Pro Tyr Thr Leu Gln
85              90                  95

Tyr Gly Arg Cys Gly Glu Lys Gly Lys Tyr Ile His Phe Thr Pro
100             105                 110

Asn Phe Leu Leu Thr Asn Asn Phe His Ile Tyr Gly Ser Arg Gly
115             120                 125

Arg Val Phe Val His Glu Trp Ala His Leu Arg Trp Gly Ile Phe
130             135                 140

Asp Glu Tyr Asn Val Asp Gln Pro Phe Tyr Ile Ser Arg Lys Asn
145             150                 155

Thr Ile Glu Ala Thr Arg Cys Ser Thr His Ile Thr Gly Ile Asn
160             165                 170

Val Val Phe Lys Lys Cys Pro Gly Gly Ser Cys Ile Thr Ser Leu
175             180                 185

Cys Arg Arg Asp Ser Gln Thr Gly Leu Tyr Glu Ala Lys Cys Thr
190             195                 200

Phe Leu Pro Lys Lys Ser Gln Thr Ala Lys Glu Ser Ile Met Phe
205             210                 215

Met Pro Ser Leu His Ser Val Thr Glu Phe Cys Thr Glu Lys Thr
220             225                 230

His Asn Thr Glu Ala Pro Asn Leu Gln Asn Lys Met Cys Asn Gly
235             240                 245

Lys Ser Thr Trp Asp Val Ile Met Asn Ser Val Asp Phe Gln Asn
250             255                 260

Thr Ser Pro Met Thr Glu Met Asn Pro Pro Thr His Pro Thr Phe
```

```
                265                 270                 275

Ser Leu Leu Lys Ser Lys Gln Arg Val Val Cys Leu Val Leu Asp
280                 285                 290

Lys Ser Gly Ser Met Ser Ala Glu Asp Arg Leu Phe Gln Met Asn
295                 300                 305

Gln Ala Ala Glu Leu Tyr Leu Ile Gln Val Ile Glu Lys Gly Ser
310                 315                 320

Leu Val Gly Met Val Thr Phe Asp Ser Val Ala Glu Ile Gln Asn
325                 330                 335

His Leu Thr Arg Ile Thr Asp Asp Asn Val Tyr Gln Lys Ile Thr
340                 345                 350

Ala Lys Leu Pro Gln Val Ala Asn Gly Gly Thr Ser Ile Cys Arg
355                 360                 365

Gly Leu Lys Ala Gly Phe Gln Ala Ile Ile His Ser Asp Gln Ser
370                 375                 380

Thr Ser Gly Ser Glu Ile Ile Leu Leu Thr Asp Gly Glu Asp Asn
385                 390                 395

Glu Ile Asn Ser Cys Phe Glu Asp Val Lys Arg Ser Gly Ala Ile
400                 405                 410

Ile His Thr Ile Ala Leu Gly Pro Ser Ala Ala Lys Glu Leu Glu
415                 420                 425

Thr Lys Ser Asn Met Thr Gly Gly Tyr Arg Phe Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
460                 465                 470

Leu Lys Ile Thr Gly Arg Lys Arg Val Asn Gly Thr Val Pro Val
475                 480                 485

Asp Ser Thr Val Gly Asn Asp Thr Phe Phe Val Val Thr Trp Thr
490                 495                 500

Ile Gln Lys Pro Glu Ile Val Leu Gln Asp Pro Lys Gly Lys Lys
505                 510                 515

Tyr Lys Thr Ser Asp Phe Lys Glu Asp Lys Leu Asn Ile Arg Ser
520                 525                 530

Ala Arg Leu Gln Ile Pro Gly Ile Ala Glu Thr Gly Thr Trp Thr
535                 540                 545

Tyr Ser Leu Leu Asn His His Ala Ser Ser Gln Met Leu Thr Val
550                 555                 560

Thr Val Thr Thr Arg Ala Arg Ser Pro Thr Ile Pro Pro Val Ile
565                 570                 575

Ala Thr Ala His Met Ser Gln His Thr Ala His Tyr Pro Ser Pro
580                 585                 590

Met Ile Val Tyr Ala Gln Val Ser Gln Gly Phe Leu Pro Val Leu
595                 600                 605

Gly Ile Ser Val Ile Ala Ile Ile Glu Thr Glu Asp Gly His Gln
610                 615                 620

Val Thr Leu Glu Leu Trp Asp Asn Gly Ala Gly Arg Asp Thr Val
625                 630                 635

Lys Asn Asp Gly Ile Tyr Ser Arg Tyr Phe Thr Asp Tyr Tyr Gly
640                 645                 650

Asn Gly Arg Tyr Ser Leu Lys Val His Ala Gln Ala Arg Asn Asn
655                 660                 665
```

```
Thr Ala Arg Leu Asn Leu Arg Gln Pro Gln Asn Lys Val Leu Tyr
670                 675                 680

Val Pro Gly Tyr Val Glu Asn Gly Lys Ile Ile Leu Asn Pro Pro
685                 690                 695

Arg Pro Glu Val Lys Asp Asp Leu Ala Lys Ala Lys Ile Glu Asp
700                 705                 710

Phe Ser Arg Leu Thr Ser Gly Gly Ser Phe Thr Val Ser Gly Ala
715                 720                 725

Pro Pro Pro Gly Asn His Pro Ser Val Phe Pro Pro Ser Lys Ile
730                 735                 740

Thr Asp Leu Glu Ala Lys Phe Lys Glu Asp Tyr Ile Gln Leu Ser
745                 750                 755

Trp Thr Ala Pro Gly Asn Val Leu Asp Lys Gly Lys Ala Ala Ser
760                 765                 770

Gly Ser Phe Pro Met Ser Arg Phe Ser His Gln Val Ala Lys Val
775                 780                 785

Leu Glu Leu Gln Leu Gln His Gln Ser Phe Gln
790                 795                 800

<210> SEQ ID NO 13
<211> LENGTH: 342
<212> TYPE: PRT
<213> ORGANISM: Unknown
<220> FEATURE:
<223> OTHER INFORMATION: Variant of Lu-ECAM-1 from bovine endothelial
      cells

<400> SEQUENCE: 13

Met Val Leu Cys Leu Asn Val Ile Leu Phe Leu Thr Leu His Leu
    -20                 -15                 -10

Leu Pro Gly Met Lys Ser Ser Met Val Asn Leu Ile Asn Asn Gly
    -5                   1                   5

Tyr Asp Gly Ile Val Ile Ala Ile Asn Pro Ser Val Pro Glu Asp
10                  15                  20

Glu Lys Leu Ile Glu Asn Ile Lys Glu Met Val Thr Glu Ala Ser
25                  30                  35

Thr Tyr Leu Phe His Ala Thr Lys Arg Arg Val Tyr Phe Arg Asn
40                  45                  50

Val Ser Ile Leu Ile Pro Met Thr Trp Lys Ser Lys Ser Glu Tyr
55                  60                  65

Phe Ile Pro Lys Gln Glu Ser Tyr Asp Gln Ala Asp Val Ile Val
70                  75                  80

Ala Asn Pro Tyr Leu Lys Tyr Gly Asp Asp Pro Tyr Thr Leu Gln
85                  90                  95

Tyr Gly Arg Cys Gly Glu Lys Gly Lys Tyr Ile His Phe Thr Pro
100                 105                 110

Asn Phe Leu Leu Thr Asn Asn Phe His Ile Tyr Gly Ser Arg Gly
115                 120                 125

Arg Val Phe Val His Glu Trp Ala His Leu Arg Trp Gly Ile Phe
130                 135                 140

Asp Glu Tyr Asn Val Asp Gln Pro Phe Tyr Ile Ser Arg Lys Asn
145                 150                 155

Thr Ile Glu Ala Thr Arg Cys Ser Thr His Ile Thr Gly Ile Asn
160                 165                 170

Val Val Phe Lys Lys Cys Pro Gly Gly Ser Cys Ile Thr Ser Leu
```

-continued

```
                        175                 180                 185
Cys Arg Arg Asp Ser Gln Thr Gly Leu Tyr Glu Ala Lys Cys Thr
190                 195                 200

Phe Leu Pro Lys Lys Ser Gln Thr Ala Lys Glu Ser Ile Met Phe
205                 210                 215

Met Pro Ser Leu His Ser Val Thr Glu Phe Cys Thr Glu Lys Thr
220                 225                 230

His Asn Thr Glu Ala Pro Asn Leu Gln Asn Lys Met Cys Asn Gly
235                 240                 245

Lys Ser Thr Trp Asp Val Ile Met Asn Ser Val Asp Phe Gln Asn
250                 255                 260

Thr Ser Pro Met Thr Glu Met Asn Pro Pro Thr His Pro Thr Phe
265                 270                 275

Ser Leu Leu Lys Ser Lys Gln Arg Val Val Cys Leu Val Leu Asp
280                 285                 290

Lys Ser Gly Ser Met Ser Ala Glu Asp Ile Tyr Leu Leu Ala Leu
295                 300                 305

Leu Ile Lys Ile Phe Lys Leu Ile Gly Asn Thr Ile
310                 315                 320 321
```

<210> SEQ ID NO 14
<211> LENGTH: 335
<212> TYPE: DNA
<213> ORGANISM: Artificial sequence
<220> FEATURE:
<223> OTHER INFORMATION: Oligonucleotide probe

<400> SEQUENCE: 14

```
caacagctac attataagaa taagtaagag tttcatggat cgtcaagaag         50
attttgacaa tgcgacttta gtgaatactt ctaatctaat acctaaggag        100
gccggatcaa agaaaatttt gaatttaag ccagaacatt ttagagtaga         150
aaatggcacc aaattctata tttcagtcca agccatcaac gaagccaatc        200
tcatctcaga ggtttctcac attgtacaag caatcaaatt tattcctcta        250
ccagaagaca gtgtccatga tctgggtacc aagatttctg aaatcactct        300
ggcaatttta ggattaccaa tgatttctc tgtat                         335
```

<210> SEQ ID NO 15
<211> LENGTH: 17
<212> TYPE: PRT
<213> ORGANISM: Artificial sequence
<220> FEATURE:
<223> OTHER INFORMATION: Synthetic peptide

<400> SEQUENCE: 15

```
Glu Asp Glu Lys Leu Ile Glu Asn Ile Lys Glu Met Val Thr Glu
                  5                  10                  15
Ala Ser
    17
```

<210> SEQ ID NO 16
<211> LENGTH: 17
<212> TYPE: PRT
<213> ORGANISM: Artificial sequence
<220> FEATURE:
<223> OTHER INFORMATION: synthetic peptide

<400> SEQUENCE: 16

Gln Asp Pro Lys Gly Lys Lys Tyr Lys Thr Ser Asp Phe Lys Glu

```
            1               5              10              15
Asp Lys
    17

<210> SEQ ID NO 17
<211> LENGTH: 24
<212> TYPE: DNA
<213> ORGANISM: Artificial Sequence
<220> FEATURE:
<223> OTHER INFORMATION: Amplification primer

<400> SEQUENCE: 17
atgttcaact catattactg gtat                                          24

<210> SEQ ID NO 18
<211> LENGTH: 20
<212> TYPE: DNA
<213> ORGANISM: Artificial sequence
<220> FEATURE:
<223> OTHER INFORMATION: Amplification primer

<400> SEQUENCE: 18
tgtaggtttg gagcttctgt                                               20

<210> SEQ ID NO 19
<211> LENGTH: 20
<212> TYPE: DNA
<213> ORGANISM: Artificial Sequence
<220> FEATURE:
<223> OTHER INFORMATION: Amplification primer

<400> SEQUENCE: 19
cacagacagg gctgtatgaa                                               20

<210> SEQ ID NO 20
<211> LENGTH: 23
<212> TYPE: DNA
<213> ORGANISM: Artificial Sequence
<220> FEATURE:
<223> OTHER INFORMATION: Amplification Primer

<400> SEQUENCE: 20
ggagatgtat tctgaaagtc aac                                           23

<210> SEQ ID NO 21
<211> LENGTH: 24
<212> TYPE: DNA
<213> ORGANISM: Artificial Sequence
<220> FEATURE:
<223> OTHER INFORMATION: Amplification primer

<400> SEQUENCE: 21
atgttcaact catattactg gtac                                          24

<210> SEQ ID NO 22
<211> LENGTH: 20
<212> TYPE: DNA
<213> ORGANISM: Artificial Sequence
<220> FEATURE:
<223> OTHER INFORMATION: Amplification primer

<400> SEQUENCE: 22
tgtaggtttg gagcttccac                                               20

<210> SEQ ID NO 23
```

```
<211> LENGTH: 20
<212> TYPE: DNA
<213> ORGANISM: Artificial Sequence
<220> FEATURE:
<223> OTHER INFORMATION: Amplification primer

<400> SEQUENCE: 23
cacagacagg gctgtatgag                                                    20

<210> SEQ ID NO 24
<211> LENGTH: 23
<212> TYPE: DNA
<213> ORGANISM: Artificial Sequence
<220> FEATURE:
<223> OTHER INFORMATION: Amplification primer

<400> SEQUENCE: 24
ggagatgtat tttgaaagtc agt                                                23

<210> SEQ ID NO 25
<211> LENGTH: 32
<212> TYPE: DNA
<213> ORGANISM: Artificial Sequence
<220> FEATURE:
<223> OTHER INFORMATION: Amplification primer

<400> SEQUENCE: 25
actgaattca gcagactaac ctctggaggg tc                                      32

<210> SEQ ID NO 26
<211> LENGTH: 32
<212> TYPE: DNA
<213> ORGANISM: Artificial Sequence
<220> FEATURE:
<223> OTHER INFORMATION: Amplification primer

<400> SEQUENCE: 26
tctactagta gctttagcta ctgaagaaca ag                                      32

<210> SEQ ID NO 27
<211> LENGTH: 3007
<212> TYPE: DNA
<213> ORGANISM: Homo sapiens

<400> SEQUENCE: 27
taacccgcat tttccaaaga gaggaatcac agggagatgt  acagca atg ggg              52 cca ttt aag agt tct gtg ttc atc ttg att ctt cac ctt cta gaa              97 ggg gcc ctg agt aat tca ctc att cag ctg aac aac aat ggc tat             142 gaa ggc att gtc gtt gca atc gac ccc aat gtg cca gaa gat gaa             187 aca ctc att caa caa ata aag gac atg gtg acc cag gca tct ctg             232 tat ctg ttt gaa gct aca gga aag cga ttt tat ttc aaa aat gtt             277 gcc att ttg att cct gaa aca tgg aag aca aag gct gac tat gtg             322 aga cca aaa ctt gag acc tac aaa aat gct gat gtt ctg gtt gct             367 gag tct act cct cca ggt aat gat gaa ccc tac act gag cag atg             412 ggc aac tgt gga gag aag ggt gaa agg atc cac ctc act cct gat             457 ttc att gca gga aaa aag tta gct gaa tat gga cca caa ggt aag             502 gca ttt gtc cat gag tgg gct cat cta cga tgg gga gta ttt gac             547 gag tac aat aat gat gag aaa ttc tac tta tcc aat gga aga ata             592
```

-continued

```
caa gca gta aga tgt tca gca ggt att act ggt aca aat gta gta       637
aag aag tgt cag gga ggc agc tgt tac acc aaa aga tgc aca ttc       682
aat aaa gtt aca gga ctc tat gaa aaa gga tgt gag ttt gtt ctc       727
caa tcc cgc cag acg gag aag gct tct ata atg ttt gca caa cat       772
gtt gat tct ata gtt gaa ttc tgt aca gaa caa aac cac aac aaa       817
gaa gct cca aac aag caa atc aaa tgc aat ctc cga agc aca           862
tgg gaa gtg atc cgt gat tct gag gac ttt aag aaa acc act cct       907
atg aca aca cag cca cca aat ccc acc ttc tca ttg ctg cag att       952
gga caa aga att gtg tgt tta gtc ctt gac aaa tct gga agc atg       997
gcg act ggt aac cgc ctc aat cga ctg aat caa gca ggc cag ctt       1042
ttc ctg ctg cag aca gtt gag ctg ggg tcc tgg gtt ggg atg gtg       1087
aca ttt gac agt gct gcc cat gta caa agt gaa ctc ata cag ata       1132
aac agt ggc agt gac agg gac aca ctc gcc aaa aga tta cct gca       1177
gca gct tca gga ggg acg tcc atc tgc agc ggg ctt cga tcg gca       1222
ttt act gtg att agg aag aaa tat cca act gat gga tct gaa att       1267
gtg ctg ctg acg gat ggg gaa gac aac act ata agt ggg tgc ttt       1312
aac gag gtc aaa caa agt ggt gcc atc atc cac aca gtc gct ttg       1357
ggg ccc tct gca gct caa gaa cta gag gag ctg tcc aaa atg aca       1402
gga ggt tta cag aca tat gct tca gat caa gtt cag aac aat ggc       1447
ctc att gat gct ttt ggg gcc ctt tca tca gga aat gga gct gtc       1492
tct cag cgc tcc atc cag ctt gag agt aag gga tta acc ctc cag       1537
aac agc cag tgg atg aat ggc aca gtg atc gtg gac agc acc gtg       1582
gga aag gac act ttg ttt ctt atc acc tgg aca acg cag cct ccc       1627
caa atc ctt ctc tgg gat ccc agt gga cag aag caa ggt ggc ttt       1672
gta gtg gac aaa aac acc aaa atg gcc tac ctc caa atc cca ggc       1717
att gct aag gtt ggc act tgg aaa tac agt ctg caa gca agc tca       1762
caa acc ttg acc ctg act gtc acg tcc cgt gcg tcc aat gct acc       1807
ctg cct cca att aca gtg act tcc aaa acg aac aag gac acc agc       1852
aaa ttc ccc agc cct ctg gta gtt tat gca aat att cgc caa gga       1897
gcc tcc cca att ctc agg gcc agt gtc aca gcc ctg att gaa tca       1942
gtg aat gga aaa aca gtt acc ttg gaa cta ctg gat aat gga gca       1987
ggt gct gat gct act aag gat gac ggt gtc tac tca agg tat ttc       2032
aca act tat gac acg aat ggt aga tac agt gta aaa gtg cgg gct       2077
ctg gga gga gtt aac gca gcc aga cgg aga gtg ata ccc cag cag       2122
agt gga gca ctg tac ata cct ggc tgg att gag aat gat gaa ata       2167
caa tgg aat cca cca aga cct gaa att aat aag gat gat gtt caa       2212
cac aag caa gtg tgt ttc agc aga aca tcc tcg gga ggc tca ttt       2257
gtg gct tct gat gtc cca aat gct ccc ata cct gat ctc ttc cca       2302
cct ggc caa atc acc gac ctg aag gcg gaa att cac ggg ggc agt       2347
```

-continued

```
ctc att aat ctg act tgg aca gct cct ggg gat gat tat gac cat       2392 gga aca gct cac aag tat atc att cga ata agt aca agt att ctt       2437 gat ctc aga gac aag ttc aat gaa tct ctt caa gtg aat act act       2482 gct ctc atc cca aag gaa gcc aac tct gag gaa gtc ttt ttg ttt       2527 aaa cca gaa aac att act ttt gaa aat ggc aca gat ctt ttc att       2572 gct att cag gct gtt gat aag gtc gat ctg aaa tca gaa ata tcc       2617 aac att gca cga gta tct ttg ttt att cct cca cag act ccg cca       2662 gag aca cct agt cct gat gaa acg tct gct cct tgt cct aat att       2707 cat atc aac agc acc att cct ggc att cac att tta aaa att atg       2752 tgg aag tgg ata gga gaa ctg cag ctg tca ata gcc tagggctgaa        2798 tttttgtcag ataaataaaa taaatcattc atccttttt ttgattataa             2848 aattttttaa aatgtatttt agaattcctg tagggggcga tatactaaat            2898
gtatatagta catttatact aaatgtattc ctgtagggggg cgatatacta           2948 aatgtatttt agaattcctg tagggggcga taaaataaaa tgctaaacaa            2998
ctggggaaa                                                          3007
```

<210> SEQ ID NO 28
<211> LENGTH: 914
<212> TYPE: PRT
<213> ORGANISM: Homo sapiens

<400> SEQUENCE: 28

```
Met Gly Pro Phe Lys Ser Ser Val Phe Ile Leu Ile Leu His Leu
1               5                   10                  15

Leu Glu Gly Ala Leu Ser Asn Ser Leu Ile Gln Leu Asn Asn Asn
                20                  25                  30

Gly Tyr Glu Gly Ile Val Val Ala Ile Asp Pro Asn Val Pro Glu
                35                  40                  45

Asp Glu Thr Leu Ile Gln Gln Ile Lys Asp Met Val Thr Gln Ala
                50                  55                  60

Ser Leu Tyr Leu Phe Glu Ala Thr Gly Lys Arg Phe Tyr Phe Lys
                65                  70                  75

Asn Val Ala Ile Leu Ile Pro Glu Thr Trp Lys Thr Lys Ala Asp
                80                  85                  90

Tyr Val Arg Pro Lys Leu Glu Thr Tyr Lys Asn Ala Asp Val Leu
                95                  100                 105

Val Ala Glu Ser Thr Pro Pro Gly Asn Asp Glu Pro Tyr Thr Glu
                110                 115                 120

Gln Met Gly Asn Cys Gly Glu Lys Gly Glu Arg Ile His Leu Thr
                125                 130                 135

Pro Asp Phe Ile Ala Gly Lys Lys Leu Ala Glu Tyr Gly Pro Gln
                140                 145                 150

Gly Lys Ala Phe Val His Glu Trp Ala His Leu Arg Trp Gly Val
                155                 160                 165

Phe Asp Glu Tyr Asn Asn Asp Glu Lys Phe Tyr Leu Ser Asn Gly
                170                 175                 180

Arg Ile Gln Ala Val Arg Cys Ser Ala Gly Ile Thr Gly Thr Asn
                185                 190                 195

Val Val Lys Lys Cys Gln Gly Gly Ser Cys Tyr Thr Lys Arg Cys
                200                 205                 210
```

-continued

```
Thr Phe Asn Lys Val Thr Gly Leu Tyr Glu Lys Gly Cys Glu Phe
            215                 220                 225
Val Leu Gln Ser Arg Gln Thr Glu Lys Ala Ser Ile Met Phe Ala
            230                 235                 240
Gln His Val Asp Ser Ile Val Glu Phe Cys Thr Glu Gln Asn His
            245                 250                 255
Asn Lys Glu Ala Pro Asn Lys Gln Asn Gln Lys Cys Asn Leu Arg
            260                 265                 270
Ser Thr Trp Glu Val Ile Arg Asp Ser Glu Asp Phe Lys Lys Thr
            275                 280                 285
Thr Pro Met Thr Thr Gln Pro Pro Asn Pro Thr Phe Ser Leu Leu
            290                 295                 300
Gln Ile Gly Gln Arg Ile Val Cys Leu Val Leu Asp Lys Ser Gly
            305                 310                 315
Ser Met Ala Thr Gly Asn Arg Leu Asn Arg Leu Asn Gln Ala Gly
            320                 325                 330
Gln Leu Phe Leu Leu Gln Thr Val Glu Leu Gly Ser Trp Val Gly
            335                 340                 345
Met Val Thr Phe Asp Ser Ala Ala His Val Gln Ser Glu Leu Ile
            350                 355                 360
Gln Ile Asn Ser Gly Ser Asp Arg Asp Thr Leu Ala Lys Arg Leu
            365                 370                 375
Pro Ala Ala Ala Ser Gly Gly Thr Ser Ile Cys Ser Gly Leu Arg
            380                 385                 390
Ser Ala Phe Thr Val Ile Arg Lys Lys Tyr Pro Thr Asp Gly Ser
            395                 400                 405
Glu Ile Val Leu Leu Thr Asp Gly Glu Asp Asn Thr Ile Ser Gly
            410                 415                 420
Cys Phe Asn Glu Val Lys Gln Ser Gly Ala Ile Ile His Thr Val
            425                 430                 435
Ala Leu Gly Pro Ser Ala Ala Gln Glu Leu Glu Glu Leu Ser Lys
            440                 445                 450
Met Thr Gly Gly Leu Gln Thr Tyr Ala Ser Asp Gln Val Gln Asn
            455                 460                 465
Asn Gly Leu Ile Asp Ala Phe Gly Ala Leu Ser Ser Gly Asn Gly
            470                 475                 480
Ala Val Ser Gln Arg Ser Ile Gln Leu Glu Ser Lys Gly Leu Thr
            485                 490                 495
Leu Gln Asn Ser Gln Trp Met Asn Gly Thr Val Ile Val Asp Ser
            500                 505                 510
Thr Val Gly Lys Asp Thr Leu Phe Leu Ile Thr Trp Thr Thr Gln
            515                 520                 525
Pro Pro Gln Ile Leu Leu Trp Asp Pro Ser Gly Gln Lys Gln Gly
            530                 535                 540
Gly Phe Val Val Asp Lys Asn Thr Lys Met Ala Tyr Leu Gln Ile
            545                 550                 555
Pro Gly Ile Ala Lys Val Gly Thr Trp Lys Tyr Ser Leu Gln Ala
            560                 565                 570
Ser Ser Gln Thr Leu Thr Leu Thr Val Thr Ser Arg Ala Ser Asn
            575                 580                 585
Ala Thr Leu Pro Pro Ile Thr Val Thr Ser Lys Thr Asn Lys Asp
            590                 595                 600
```

```
Thr Ser Lys Phe Pro Ser Pro Leu Val Val Tyr Ala Asn Ile Arg
            605                 610                 615

Gln Gly Ala Ser Pro Ile Leu Arg Ala Ser Val Thr Ala Leu Ile
            620                 625                 630

Glu Ser Val Asn Gly Lys Thr Val Thr Leu Gln Leu Leu Asp Asn
            635                 640                 645

Gly Ala Gly Ala Asp Ala Thr Lys Asp Asp Gly Val Tyr Ser Arg
            650                 655                 660

Tyr Phe Thr Thr Tyr Asp Thr Asn Gly Arg Tyr Ser Val Lys Val
            665                 670                 675

Arg Ala Leu Gly Gly Val Asn Ala Ala Arg Arg Val Ile Pro
            680                 685                 690

Gln Gln Ser Gly Ala Leu Tyr Ile Pro Gly Trp Ile Glu Asn Asp
            695                 700                 705

Glu Ile Gln Trp Asn Pro Pro Arg Pro Glu Ile Asn Lys Asp Asp
            710                 715                 720

Val Gln His Lys Gln Val Cys Phe Ser Arg Thr Ser Ser Gly Gly
            725                 730                 735

Ser Phe Val Ala Ser Asp Val Pro Asn Ala Pro Ile Pro Asp Leu
            740                 745                 750

Phe Pro Pro Gly Gln Ile Thr Asp Leu Lys Ala Glu Ile His Gly
            755                 760                 765

Gly Ser Leu Ile Asn Leu Thr Trp Thr Ala Pro Gly Asp Asp Tyr
            770                 775                 780

Asp His Gly Thr Ala His Lys Tyr Ile Ile Arg Ile Ser Thr Ser
            785                 790                 795

Ile Leu Asp Leu Arg Asp Lys Phe Asn Glu Ser Leu Gln Val Asn
            800                 805                 810

Thr Thr Ala Leu Ile Pro Lys Glu Ala Asn Ser Glu Glu Val Phe
            815                 820                 825

Leu Phe Lys Pro Glu Asn Ile Thr Phe Glu Asn Gly Thr Asp Leu
            830                 835                 840

Phe Ile Ala Ile Gln Ala Val Asp Lys Val Asp Leu Lys Ser Glu
            845                 850                 855

Ile Ser Asn Ile Ala Arg Val Ser Leu Phe Ile Pro Pro Gln Thr
            860                 865                 870

Pro Pro Glu Thr Pro Ser Pro Asp Glu Thr Ser Ala Pro Cys Pro
            875                 880                 885

Asn Ile His Ile Asn Ser Thr Ile Pro Gly Ile His Ile Leu Lys
            890                 895                 900

Ile Met Trp Lys Trp Ile Gly Glu Leu Gln Leu Ser Ile Ala
            905                 910                 914

<210> SEQ ID NO 29
<211> LENGTH: 3418
<212> TYPE: DNA
<213> ORGANISM: Homo sapiens

<400> SEQUENCE: 29
tttgtttaac atgcaaga atg gtg ttc agt ctg aag gtg att ctc ttc          48 cta tcc ttg ctt ctc tcg cct gta ttg aaa agc tca ctg gta act          93 ttg aat aac aat gga tat gat ggc att gtg att gca att aat ccc         138 agt gta cca gaa gat gaa aaa ctc att caa aac ata aag gaa atg         183
```

```
gta act gaa gca tct act cac ctg ttt cat gcc acc aaa caa aga      228
gct tat ttc agg aat gta agc att tta att cca atg acc tac aaa      273
tca aaa tct gag tac tta atc cca aaa caa gaa aca tat gac cag      318
gca gat gtc ata gtt gct gat ctt tac ctg aaa tac gga gat gat      363
ccc tat aca ctt caa tat gga caa tgt gga gat aaa gga caa tat      408
ata cat ttt act cca aac ttc ttg ttg act aat aac ttg gct acc      453
tat ggg cct cga ggt aaa gta ttt gtc cat ggg tgg gcc cat ctc      498
cgg tgg gga gta ttt gat gag tat aat gtg gac cag cca ttc tat      543
att tcc aga aga aac act act gaa gca aca aga tgt tcc act cgt      588
att act gtt tac atg gtt ttg aac gaa tgc aag ggg gcc agc tgt      633
ata gca cga cca ttc aga cgt gac tca cag aca ggg ctg tat gaa      678
gca aaa tgt aca ttt atc cca aag aga tcc cag act gcc aag gaa      723
tcc att gtg ttt atg caa aat ctt gat tct gtg act gaa ttt tgt      768
act gaa aaa aca cac aat aaa gaa gct cca aac cta tat aac aaa      813
atg tgc aat cac aga agc aca tgg gat gta atc atg agc tct gaa      858
gat ttt cag cat tta tct ccc atg aca gaa ata aat tta cct cgt      903
cct aca ttt tca ttg ctc aag tcc aaa cag cgt gta gtc tgt ttg      948
gta ctt gat aaa tct gga agc atg aat gca gaa gac cgt ctc ttt      993
cga atg aat caa gca gca gaa ttg tac ttg att caa att att gaa     1038
aag gga tcc ttg gtt ggg ttg gtc aca ttt gac agt ttt gct aaa     1083
atc caa agt aag ctc ata aaa ata att gat gat aac act tac caa     1128
aag atc act gca aac ctg cct caa gaa gct gat ggt ggc act tca     1173
att tgc agg gga ctc aaa gca gga ttt cag gca att ccc cag agt     1218
aat cag agt act ttc ggt tct gaa atc ata tta cta aca gat ggg     1263
gaa gat tat caa ata agc tta tgc ttt gga gag gta aaa caa agt     1308
ggc aca gtc atc cac acc att gct ctg ggg ccg tct gct gac gaa     1353
gaa ctg gag acc ctg tca aat atg aca gga tta cat aag gga cac     1398
tgt tat act gaa agt tca tat agt gct ggg aag ttc atc ttt tgt     1443
gga cat cgt ttt tat gcc cat aaa aac ata aat ggc ctt att gat     1488
gct ttc agc aga att tca tct aga agt ggc agc atc tct cag cag     1533
gct ctt cag ttg gaa agt aaa act ttg aat atc cca gcg aag aaa     1578
tgg ata aat ggt aca gtg cct gtg gat agt aca gtt aga aat gat     1623
act tcc ttt gtt gtc aca tgg acg ata caa aag cca gca ata att     1668
ctt caa gat cca aaa gga aaa aaa tat act acc tca gat ttt caa     1713
gaa ggt gaa cta aat att cgg tct gcc cgt ctt cga ata cca ggt     1758
att gca gag aca ggc act tgg act tac agc gtt cga aac aat cat     1803
acc aaa tct caa ttg cta act gtg aca atg acc act cga gca aga     1848
agc cct acc aca ctc cca gta att gca act gct cac atg agt caa     1893
aat aca gct cat tac cct agc cca gtg att gtt tat gca tgt gtc     1938
agt caa ggg ttt ctt cct gtt ctg gga atc aat gta aca gcc att     1983
```

-continued

```
ata gaa aat gaa gag gga cat caa gta aca ttg gag ctc tgc gac      2028
aat ggc gca ggt gct gat tct gtc aag aat gat ggc atc tac tca      2073
agg tat ttt aca gat tac cat gga aat ggt aga tac agt tta aaa      2118
gtg ctt acc cag gca aga aaa aac aca gct agg cta agt caa caa      2163
cag aat aaa gct ctg tat gta ccg cgc tat gct gaa aat gga aaa      2208
att ata ctg aac cca tcc aaa cct gaa gtc aca gat gat gtg aaa      2253
gga gct caa aca gac gac ttc agc aga ctc acc tct gga ggg tcg      2298
ttt act gta tca gga gtg cct cct aat ggt aat cat tct cag gtg      2343
ttc tca cct ggt aaa att gta gac ctc gag gct aag ttt caa gga      2388
gat cat att caa ctt tca tgg act gcc cct ggc aag gtc ctc gat      2433
aaa gga aga gct gag agc tac att ata aga ata agt aaa cat ttc      2478
ctg gac ctc caa gaa gat ttt gat aaa gct gct tta ata aat act      2523
tct ggt ctg ata cct aag gag cct ggt tca gta gaa agt ttt gaa      2568
ttt aaa cca gaa cct tct aaa ata gag aat ggt acg aca ttc tat      2613
att gca att caa gcc atc cat gaa gcc aat gtc acc tca gag gtt      2658
tca aac att gca caa gca act aac ttt att cct cca cag gaa ccc      2703
agc att cct gat ctg ggt acc aat att tct gca atc agt ttg gca      2748
att ttt gga tta gct gta att tta tct ata ttt tat act aga aat      2793
tat att aga act caa att caa tgt tat aca tac ttg gta aac att      2838
tat tta aaa ttt aat tta cta tac tta ttg tct att ata aag ctc      2883
att ata ata tat aaa gtg aag tac aaa agt tgt aag ttt cct aat      2928
tac ttg att aat tat tac tat ttg agt tat tat atg tta atc aaa      2973
atg agt ata tca ttt cct gtc tgg aat aat cca ctc att aat ttt      3018
taatatgaaa agatatatat ttgtacttgt aagcatttta agaaacattt           3068
ttaaagtgtg ctacaaattc atttggtgta ctaacatcaa aatgtatcca           3118
agccatttaa aaaatattta tatatacata gtagcaaata gttttataga           3168
tttatttgta tcgcattttt tattacaaat gaatatttca tgtttatata           3218
agctgtaatc aaaaaggact agtagtagta gtaaggaagt caaatttgtt           3268
tttttatcat tgattataag tggtatattt gttttttgtc attgattaaa           3318
agtgatttta gccctaggcc cgaaatgact agcaaatatc attttctgta           3368
tgaattgtgg aacatcacaa taaaattatt tctgtgctga tgctaaaaaa           3418
```

<210> SEQ ID NO 30
<211> LENGTH: 1000
<212> TYPE: PRT
<213> ORGANISM: Homo sapiens

<400> SEQUENCE: 30

Met Val Phe Ser Leu Lys Val Ile Leu Phe Ser Leu Leu Leu
1               5                   10                  15

Ser Pro Val Leu Lys Ser Ser Leu Val Thr Leu Asn Asn Gly
                20                  25                  30

Tyr Asp Gly Ile Val Ile Ala Ile Asn Pro Ser Val Pro Glu Asp
                35                  40                  45

-continued

```
Glu Lys Leu Ile Gln Asn Ile Lys Glu Met Val Thr Gln Ala Ser
                50                  55                  60

Thr His Leu Phe His Ala Thr Lys Gln Arg Ala Tyr Phe Arg Asn
                65                  70                  75

Val Ser Ile Leu Ile Pro Met Thr Tyr Lys Ser Lys Ser Glu Tyr
                80                  85                  90

Leu Ile Pro Lys Gln Glu Thr Tyr Asp Gln Ala Asp Val Ile Val
                95                 100                 105

Ala Asp Leu Tyr Leu Lys Tyr Gly Asp Pro Tyr Thr Leu Gln
               110                 115                 120

Tyr Gly Gln Cys Gly Asp Lys Gly Gln Tyr Ile His Phe Thr Pro
               125                 130                 135

Asn Phe Leu Leu Thr Asn Asn Leu Ala Thr Tyr Gly Pro Arg Gly
               140                 145                 150

Lys Val Phe Val His Gly Trp Ala His Leu Arg Trp Gly Val Phe
               155                 160                 165

Asp Glu Tyr Asn Val Asp Gln Pro Phe Tyr Ile Ser Arg Arg Asn
               170                 175                 180

Thr Thr Glu Ala Thr Arg Cys Ser Thr Arg Ile Thr Val Tyr Met
               185                 190                 195

Val Leu Asn Glu Cys Lys Gly Ala Ser Cys Ile Ala Arg Pro Phe
               200                 205                 210

Arg Arg Asp Ser Gln Thr Gly Leu Tyr Glu Ala Lys Cys Thr Phe
               215                 220                 225

Ile Pro Lys Arg Ser Gln Thr Ala Lys Glu Ser Ile Val Phe Met
               230                 235                 240

Gln Asn Leu Asp Ser Val Thr Glu Phe Cys Thr Glu Lys Thr His
               245                 250                 255

Asn Lys Glu Ala Pro Asn Leu Tyr Asn Lys Met Cys Asn His Arg
               260                 265                 270

Ser Thr Trp Asp Val Ile Met Ser Ser Glu Asp Phe Gln His Leu
               275                 280                 285

Ser Pro Met Thr Glu Ile Asn Leu Pro Arg Pro Thr Phe Ser Leu
               290                 295                 300

Leu Lys Ser Lys Gln Arg Val Val Cys Leu Val Leu Asp Lys Ser
               305                 310                 315

Gly Ser Met Asn Ala Glu Asp Arg Leu Phe Arg Met Asn Gln Ala
               320                 325                 330

Ala Glu Leu Tyr Leu Ile Gln Ile Ile Glu Lys Gly Ser Leu Val
               335                 340                 345

Gly Leu Val Thr Phe Asp Ser Phe Ala Lys Ile Gln Ser Lys Leu
               350                 355                 360

Ile Lys Ile Ile Asp Asp Asn Thr Tyr Gln Lys Ile Thr Ala Asn
               365                 370                 375

Leu Pro Gln Glu Ala Asp Gly Gly Thr Ser Ile Cys Arg Gly Leu
               380                 385                 390

Lys Ala Gly Phe Gln Ala Ile Pro Gln Ser Asn Gln Ser Thr Phe
               395                 400                 405

Gly Ser Glu Ile Ile Leu Leu Thr Asp Gly Glu Asp Tyr Gln Ile
               410                 415                 420

Ser Leu Cys Phe Gly Glu Val Lys Gln Ser Gly Thr Val Ile His
               425                 430                 435
```

-continued

```
Thr Ile Ala Leu Gly Pro Ser Ala Asp Glu Leu Glu Thr Leu
            440                 445                 450

Ser Asn Met Thr Gly Leu His Lys Gly His Cys Tyr Thr Glu Ser
            455                 460                 465

Ser Tyr Ser Ala Gly Lys Phe Ile Phe Cys Gly His Arg Phe Tyr
            470                 475                 480

Ala His Lys Asn Ile Asn Gly Leu Ile Asp Ala Phe Ser Arg Ile
            485                 490                 495

Ser Ser Arg Ser Gly Ser Ile Ser Gln Gln Ala Leu Gln Leu Glu
            500                 505                 510

Ser Lys Thr Leu Asn Ile Pro Ala Lys Lys Trp Ile Asn Gly Thr
            515                 520                 525

Val Pro Val Asp Ser Thr Val Arg Asn Asp Thr Ser Phe Val Val
            530                 535                 540

Thr Trp Thr Ile Gln Lys Pro Ala Ile Ile Leu Gln Asp Pro Lys
            545                 550                 555

Gly Lys Lys Tyr Thr Thr Ser Asp Phe Gln Glu Gly Glu Leu Asn
            560                 565                 570

Ile Arg Ser Ala Arg Leu Arg Ile Pro Gly Ile Ala Glu Thr Gly
            575                 580                 585

Ile Trp Thr Tyr Ser Val Arg Asn Asn His Thr Lys Ser Gln Leu
            590                 595                 600

Leu Thr Val Thr Met Thr Thr Arg Ala Arg Ser Pro Thr Thr Leu
            605                 610                 615

Pro Val Ile Ala Thr Ala His Ser Met Gln Asn Thr Ala His Tyr
            620                 625                 630

Pro Ser Pro Val Ile Val Tyr Ala Cys Val Ser Gln Gly Phe Leu
            635                 640                 645

Pro Val Leu Gly Ile Asn Val Thr Ala Ile Ile Glu Asn Glu Glu
            650                 655                 660

Gly His Gln Val Thr Leu Glu Leu Cys Asp Asn Gly Ala Gly Ala
            665                 670                 675

Asp Ser Val Lys Asn Asp Gly Ile Tyr Ser Arg Tyr Phe Thr Asp
            680                 685                 690

Tyr His Gly Asn Gly Arg Tyr Ser Leu Lys Val Leu Thr Gln Ala
            695                 700                 705

Arg Lys Asn Thr Ala Arg Leu Ser Gln Gln Asn Lys Ala Leu
            710                 715                 720

Tyr Val Pro Arg Tyr Ala Glu Asn Gly Lys Ile Ile Leu Asn Pro
            725                 730                 735

Ser Lys Pro Glu Val Thr Asp Asp Val Glu Gly Ala Gln Thr Asp
            740                 745                 750

Asp Phe Ser Arg Leu Thr Ser Gly Gly Ser Phe Thr Val Ser Gly
            755                 760                 765

Val Pro Pro Asn Gly Asn His Ser Gln Val Phe Ser Pro Gly Lys
            770                 775                 780

Ile Val Asp Leu Glu Ala Lys Phe Gln Gly Asp His Ile Gln Leu
            785                 790                 795

Ser Trp Thr Ala Pro Gly Lys Val Leu Asp Lys Gly Arg Ala Glu
            800                 805                 810

Ser Tyr Ile Ile Arg Ile Ser Lys His Phe Leu Asp Leu Gln Glu
            815                 820                 825

Asp Phe Asp Lys Ala Ala Leu Ile Asn Thr Ser Gly Leu Ile Pro
```

```
                    830                 835                 840
Lys Glu Pro Gly Ser Val Glu Ser Phe Glu Phe Lys Pro Glu Pro
                845                 850                 855
Ser Lys Ile Glu Asn Gly Thr Thr Phe Tyr Ile Ala Ile Gln Ala
            860                 865                 870
Ile His Glu Ala Asn Val Thr Ser Glu Val Ser Asn Ile Ala Gln
        875                 880                 885
Ala Thr Asn Phe Ile Pro Pro Gln Pro Ser Ile Pro Asp Leu
    890                 895                 900
Gly Thr Asn Ile Ser Ala Ile Ser Leu Ala Ile Phe Gly Leu Ala
                905                 910                 915
Val Ile Leu Ser Ile Phe Tyr Thr Arg Asn Tyr Ile Arg Thr Gln
                920                 925                 930
Ile Gln Cys Tyr Thr Tyr Leu Val Asn Ile Tyr Leu Lys Phe Asn
                935                 940                 945
Leu Leu Tyr Leu Leu Ser Ile Ile Lys Leu Ile Ile Tyr Lys
                950                 955                 960
Val Lys Tyr Lys Ser Cys Lys Phe Pro Asn Tyr Leu Ile Asn Tyr
                965                 970                 975
Tyr Tyr Leu Ser Tyr Tyr Met Leu Ile Lys Met Ser Ile Ser Phe
                980                 985                 990
Pro Val Trp Asn Asn Pro Leu Ile Asn Phe
                995                 1000

<210> SEQ ID NO 31
<211> LENGTH: 2970
<212> TYPE: DNA
<213> ORGANISM: Homo sapiens

<400> SEQUENCE: 31
acctaaaacc ttgcaagttc aggaagaaac catctgcatc catattgaaa          50
acctgacaca atgtatgcag caggctcagt gtgagtgaac tggaggcttc         100 tctacaac atg acc caa agg agc att gca ggt cct att tgc aac       144 ctg aag ttt gtg act ctc ctg gtt gcc tta agt tca gaa ctc cca   189 ttc ctg gga gct gga gta cag ctt caa gac aat ggg tat aat gga   234 ttg ctc att gca att aat cct cag gta cct gag aat cag aac ctc   279 atc tca aac att aag gaa atg ata act gaa gct tca ttt tac cta   324 ttt aat gct acc aag aga aga gta ttt ttc aga aat ata aag att   369 tta ata cct gcc aca tgg aaa gct aat aat aac agc aaa ata aaa   414 caa gaa tca tat gaa aag gca aat gtc ata gtg act gac tgg tat   459 ggg gca cat gga gat gat cca tac acc cta caa tac aga ggg tgt   504 gga aaa gag gga aaa tac att cat ttc aca cct aat ttc cta ctg   549 aat gat aac tta aca gct ggc tac gga tca cga ggc cga gtg ttt   594 gtc cat gaa tgg gcc cac ctc cgt tgg ggt gtg ttc gat gag tat   639 aac aat gac aaa cct ttc tac ata aat ggg caa aat caa att aaa   684 gtg aca agg tgt tca tct gac atc aca ggc att ttt gtg tgt gaa   729 aaa ggt cct tgc ccc caa gaa aac tgt att att agt aag ctt ttt   774 aaa gaa gga tgc acc ttt atc tac aat agc acc caa aat gca act   819
```

-continued

```
gca tca ata atg ttc atg caa agt tta tct tct gtg gtt gaa ttt        864
tgt aat gca agt acc cac aac caa gaa gca cca aac cta cag aac        909
cag atg tgc agc ctc aga agt gca tgg gat gta atc aca gac tct        954
gct gac ttt cac cac agc ttt ccc atg aat ggg act gag ctt cca        999
cct cct ccc aca ttc tcg ctt gta cag gct ggt gac aaa gtg gtc       1044
tgt tta gtg ctg gat gtg tcc agc aag atg gca gag gct gac aga       1089
ctc ctt caa cta caa caa gcc gca gaa ttt tat ttg atg cag att       1134
gtt gaa att cat acc ttc gtg ggc att gcc agt ttc gac agc aaa       1179
gga gag atc aga gcc cag cta cac caa att aac agc aat gat gat       1224
cga aag ttg ctg gtt tca tat ctg ccc acc act gta tca gct aaa       1269
aca gac atc agc att tgt tca ggg ctt aag aaa gga ttt gag gtg       1314
gtt gaa aaa ctg aat gga aaa gct tat ggc tct gtg atg ata tta       1359
gtg acc agc gga gat gat aag ctt ctt ggc aat tgc tta ccc act       1404
gtg ctc agc agt ggt tca aca att cac tcc att gcc ctg ggt tca       1449
tct gca gcc cca aat ctg gag gaa tta tca cgt ctt aca gga ggt       1494
tta aag ttc ttt gtt cca gat ata tca aac tcc aat agc atg att       1539
gat gct ttc agt aga att tcc tct gga act gga gac att ttc cag       1584
caa cat att cag ctt gaa agt aca ggt gaa aat gtc aaa cct cac       1629
cat caa ttg aaa aac aca gtg act gtg gat aat act gtg ggc aac       1674
gac act atg ttt cta gtt acg tgg cag gcc agt ggt cct cct gag       1719
att ata tta ttt gat cct gat gga cga aaa tac tac aca aat aat       1764
ttt atc acc aat cta act ttt cgg aca gct agt ctt tgg att cca       1809
gga aca gct aag cct ggg cac tgg act tac acc ctg aac aat acc       1854
cat cat tct ctg caa gcc ctg aaa gtg aca gtg acc tct cgc gcc       1899
tcc aac tca gct gtg ccc cca gcc act gtg aaa gcc ttt gtg aaa       1944
aga gac agc ctc att ttt cct cat cct gtg atg att tat gcc aat       1989
gtg aaa cag gga ttt tat ccc att ctt aat gcc act gtc act gcc       2034
aca gtt gag cca gag act gga gat cct gtt acg ctg aga ctc ctt       2079
gat gat gga gca ggt gct gat gtt ata aaa aat gat gga att tac       2124
tcg agg tat ttt ttc tcc ttt gct gca aat ggt aga tat agc ttg       2169
aaa gtg cat gtc aat cac tct ccc agc ata agc acc cca gcc cac       2214
tct att cca ggg agt cat gct atg tat gta cca ggt tac aca gca       2259
aac ggt aat att cag atg aat gct cca agg aaa tca gta ggc aga       2304
aat gag gag gag cga aag tgg ggc ttt agc cga gtc agc tca gga       2349
ggc tcc ttt tca gtg ctg gga gtt cca gct ggc ccc cac cct gat       2394
gtg ttt cca cca tgc aaa att att gac ctg gaa gct gta aaa gta       2439
gaa gag gaa ttg acc cta tct tgg aca gca cct gga gaa gac ttt       2484
gat cag ggc cag gct aca agc tat gaa ata aga atg agt aaa agt       2529
cta cag aat atc caa gat gac ttt aac aat gct att tta gta aat       2574
aca tca aag cga aat cct cag caa gct ggc atc agg gag ata ttt       2619
```

-continued

| | |
|---|---|
| acg ttc tca ccc cag att tcc acg aat gga cct gaa cat cag cca | 2664 |
| aat gga gaa aca cat gaa agc cac aga att tat gtt gca ata cga | 2709 |
| gca atg gat agg aac tcc tta cag tct gct gta tct aac att gcc | 2754 |
| cag gcg cct ctg ttt att ccc ccc aat tct gat cct gta cct gcc | 2799 |
| aga gat tat ctt ata ttg aaa gga gtt tta aca gca atg ggt ttg | 2844 |
| ata gga atc att tgc ctt att ata gtt gtg aca cat cat act tta | 2889 |
| agc agg aaa aag aga gca gac aag aaa gag aat gga aca aaa tta | 2934 |
| tta taaataaata tccaaagtgt cttccttctc aaa | 2970 |

<210> SEQ ID NO 32
<211> LENGTH: 943
<212> TYPE: PRT
<213> ORGANISM: Homo sapiens

<400> SEQUENCE: 32

Met Thr Gln Arg Ser Ile Ala Gly Pro Ile Cys Asn Leu Lys Phe
1               5                   10                  15

Val Thr Leu Leu Val Ala Leu Ser Ser Glu Leu Pro Phe Leu Gly
                20                  25                  30

Ala Gly Val Gln Leu Gln Asp Asn Gly Tyr Asn Gly Leu Leu Ile
                35                  40                  45

Ala Ile Asn Pro Gln Val Pro Glu Asn Gln Asn Leu Ile Ser Asn
                50                  55                  60

Ile Lys Glu Met Ile Thr Glu Ala Ser Phe Tyr Leu Phe Asn Ala
                65                  70                  75

Thr Lys Arg Arg Val Phe Phe Arg Asn Ile Lys Ile Leu Ile Pro
                80                  85                  90

Ala Thr Trp Lys Ala Asn Asn Asn Ser Lys Ile Lys Gln Glu Ser
                95                  100                 105

Tyr Glu Lys Ala Asn Val Ile Val Thr Asp Trp Tyr Gly Ala His
                110                 115                 120

Gly Asp Asp Pro Tyr Thr Leu Gln Tyr Arg Gly Cys Gly Lys Glu
                125                 130                 135

Gly Lys Tyr Ile His Phe Thr Pro Asn Phe Leu Leu Asn Asp Asn
                140                 145                 150

Leu Thr Ala Gly Tyr Gly Ser Arg Gly Arg Val Phe Val His Glu
                155                 160                 165

Trp Ala His Leu Arg Trp Gly Val Phe Asp Glu Tyr Asn Asn Asp
                170                 175                 180

Lys Pro Phe Tyr Ile Asn Gly Gln Asn Gln Ile Lys Val Thr Arg
                185                 190                 195

Cys Ser Ser Asp Ile Thr Gly Ile Phe Val Cys Glu Lys Gly Pro
                200                 205                 210

Cys Pro Gln Glu Asn Cys Ile Ile Ser Lys Leu Phe Lys Glu Gly
                215                 220                 225

Cys Thr Phe Ile Tyr Asn Ser Thr Gln Asn Ala Thr Ala Ser Ile
                230                 235                 240

Met Phe Met Gln Ser Leu Ser Ser Val Val Glu Phe Cys Asn Ala
                245                 250                 255

Ser Thr His Asn Gln Glu Ala Pro Asn Leu Gln Asn Gln Met Cys
                260                 265                 270

-continued

```
Ser Leu Arg Ser Ala Trp Asp Val Ile Thr Asp Ser Ala Asp Phe
            275                 280                 285

His His Ser Phe Pro Met Asn Gly Thr Glu Leu Pro Pro Pro
            290                 295                 300

Thr Phe Ser Leu Val Gln Ala Gly Asp Lys Val Val Cys Leu Val
            305                 310                 315

Leu Asp Val Ser Ser Lys Met Ala Glu Ala Asp Arg Leu Leu Gln
            320                 325                 330

Leu Gln Gln Ala Ala Glu Phe Tyr Leu Met Gln Ile Val Glu Ile
            335                 340                 345

His Thr Phe Val Gly Ile Ala Ser Phe Asp Ser Lys Gly Glu Ile
            350                 355                 360

Arg Ala Gln Leu His Gln Ile Asn Ser Asn Asp Arg Lys Leu
            365                 370                 375

Leu Val Ser Tyr Leu Pro Thr Thr Val Ser Ala Lys Thr Asp Ile
            380                 385                 390

Ser Ile Cys Ser Gly Leu Lys Lys Gly Phe Glu Val Val Glu Lys
            395                 400                 405

Leu Asn Gly Lys Ala Tyr Gly Ser Val Met Ile Leu Val Thr Ser
            410                 415                 420

Gly Asp Asp Lys Leu Leu Gly Asn Cys Leu Pro Thr Val Leu Ser
            425                 430                 435

Ser Gly Ser Thr Ile His Ser Ile Ala Leu Gly Ser Ser Ala Ala
            440                 445                 450

Pro Asn Leu Glu Glu Leu Ser Arg Leu Thr Gly Gly Leu Lys Phe
            455                 460                 465

Phe Val Pro Asp Ile Ser Asn Ser Asn Ser Met Ile Asp Ala Phe
            470                 475                 480

Ser Arg Ile Ser Ser Gly Thr Gly Asp Ile Phe Gln Gln His Ile
            485                 490                 495

Gln Leu Glu Ser Thr Gly Glu Asn Val Lys Pro His His Gln Leu
            500                 505                 510

Lys Asn Thr Val Thr Val Asp Asn Thr Val Gly Asn Asp Ile Met
            515                 520                 525

Phe Leu Val Thr Trp Gln Ala Ser Gly Pro Pro Glu Ile Ile Leu
            530                 535                 540

Phe Asp Pro Asp Gly Arg Lys Tyr Tyr Thr Asn Asn Phe Thr Thr
            545                 550                 555

Asn Leu Thr Phe Arg Thr Ala Ser Leu Trp Ile Pro Gly Thr Ala
            560                 565                 570

Lys Pro Gly His Trp Thr Tyr Thr Leu Asn Asn Thr His His Ser
            575                 580                 585

Leu Gln Ala Leu Lys Val Thr Val Thr Ser Arg Ala Ser Asn Ser
            590                 595                 600

Ala Val Pro Pro Ala Thr Val Glu Ala Phe Val Glu Arg Asp Ser
            605                 610                 615

Leu His Phe Pro His Pro Val Met Ile Tyr Ala Asn Val Lys Gln
            620                 625                 630

Gly Phe Tyr Pro Ile Ile Asn Ala Thr Val Thr Ala Thr Val Glu
            635                 640                 645

Pro Glu Thr Gly Asp Pro Val Thr Leu Arg Leu Leu Asp Asp Gly
            650                 655                 660

Ala Gly Ala Asp Val Ile Lys Asn Asp Gly Ile Tyr Ser Arg Tyr
```

```
                    665                 670                 675
Phe Phe Ser Phe Ala Ala Asn Gly Arg Tyr Ser Leu Lys Val His
                680                 685                 690
Val Asn His Ser Pro Ser Ile Ser Thr Pro Ala His Ser Ile Pro
                695                 700                 705
Gly Ser His Ala Met Tyr Val Pro Gly Tyr Thr Ala Asn Gly Asn
                710                 715                 720
Ile Gln Met Asn Ala Pro Arg Lys Ser Val Gly Arg Asn Glu Glu
                725                 730                 735
Glu Arg Lys Trp Gly Phe Ser Arg Val Ser Ser Gly Ser Phe
                740                 745                 750
Ser Val Leu Gly Val Pro Ala Gly Pro His Pro Asp Val Phe Pro
                755                 760                 765
Pro Cys Lys Ile Ile Asp Leu Glu Ala Val Lys Val Glu Glu Glu
                770                 775                 780
Leu Thr Leu Ser Trp Thr Ala Pro Gly Glu Asp Phe Asp Gln Gly
                785                 790                 795
Gln Ala Thr Ser Tyr Glu Ile Arg Met Ser Lys Ser Leu Gln Asn
                800                 805                 810
Ile Gln Asp Asp Phe Asn Asn Ala Ile Leu Val Asn Thr Ser Lys
                815                 820                 825
Arg Asn Pro Gln Gln Ala Gly Ile Arg Glu Ile Phe Thr Phe Ser
                830                 835                 840
Pro Gln Ile Ser Thr Asn Gly Pro Glu His Gln Pro Asn Gly Glu
                845                 850                 855
Thr His Glu Ser His Arg Ile Tyr Val Ala Ile Arg Ala Met Asp
                860                 865                 870
Arg Asn Ser Leu Gln Ser Ala Val Ser Asn Ile Ala Gln Ala Pro
                875                 880                 885
Leu Phe Ile Pro Pro Asn Ser Asp Pro Val Pro Ala Arg Asp Tyr
                890                 895                 900
Leu Ile Leu Lys Gly Val Leu Thr Ala Met Gly Leu Ile Gly Ile
                905                 910                 915
Ile Cys Leu Ile Ile Val Val Thr His His Thr Leu Ser Arg Lys
                920                 925                 930
Lys Arg Ala Asp Lys Lys Glu Asn Gly Thr Lys Leu Leu
                935                 940         943

<210> SEQ ID NO 33
<211> LENGTH: 3022
<212> TYPE: DNA
<213> ORGANISM: Mus musculus

<400> SEQUENCE: 33
actggagcag tgcgacc atg gtg cca ggg ctg cag gtc ctt ctg ttc         47 ctc acc ctg cat ctc ctg cag aac aca gag agc tcc atg gtg cat         92 ctc aac agc aat gga tac gag ggt gtg gtc att gcc att aac ccc        137 agt gtg cca gag gac gaa agg ctc atc cca agc ata aag gaa atg        182 gta act caa gct tct acc tac ctg ttt gaa gcc agc caa gga aga        227 gtt tat ttc agg aac ata agc ata tta gtc ccg atg acc tgg aag        272 tcg aaa tct gag tac tta atg cca aaa cga gaa tcg tac gac aaa        317 gca gac gtc ata gtt gcg gat cct cac ctg caa cat gga gac gac        362
```

-continued

| | |
|---|---|
| ccc tac acc ctt cag tat gga cag tgt ggg gac aga gga cag tac | 407 |
| ata cac ttc act cca aac ttc cta ctc act gat aac ttg cgt atc | 452 |
| tat gga ccc cga ggc aga gtc ttt gtc cat gag tgg gcc cat ctc | 497 |
| cgg tgg gga gta ttt gat gag tat aac gtg gac cgg tca ctt tac | 542 |
| att tct aga aag aac act ata gaa gca aca agg tgc tcc gcc agc | 587 |
| atc aca ggc aag aag gtg gtc cac gag tgt cag aga ggc agc tgt | 632 |
| gtg aca agg gcg tgc cgg cgt gac tcg aag aca cgg ctg tat gaa | 677 |
| ccc aaa tgt aca ttt atc cca gac aaa ata cag aca gct ggg gcc | 722 |
| tcc ata atg ttc atg caa aac ctc aat tct gtg gtt gaa ttt tgc | 767 |
| aca gaa aat aac cac aat gca gaa gcc cca aac cta caa aac aaa | 812 |
| atg tgc aat cgc aga agc acg tgg gat gta atc aag acg tct gct | 857 |
| gac ttt cag aat gcc cct ccc atg aga gga aca gaa gcc cct cct | 902 |
| cca cct aca ttt tat ctg ctc aag tcc aga agg cga gtg gtg tgc | 947 |
| ttg gtg ctg gat aaa tct gga agc atg gac aaa gaa gac cgt ctt | 992 |
| att cga atg aat caa gca gca gaa ctg tac tta act caa att gtg | 1037 |
| gaa aag gag tct atg gtt gga tta gtc aca ttt gac agc gct gcc | 1082 |
| cac atc caa aat tat cta ata aaa ata acg agt agt agt gac tac | 1127 |
| caa aag atc acc gca aac ctc ccc caa cag gct tct ggt gga act | 1172 |
| tca att tgc cat gga ctc cag gca gga ttt cag gca att acc tcc | 1217 |
| agt gac cag agc act tcc ggt tct gag atc gta ttg ctg aca gat | 1262 |
| ggg gaa gat aat gga ata cgt tcc tgc ttt gag gcc gtc tct cgc | 1307 |
| agc ggt gcc atc atc cac acc atc gct ctg ggg cct tcg cgt gcc | 1352 |
| cga gaa ctg gag act ctg tcg gac atg aca gga ggg ctt cgt ttc | 1397 |
| tat gcc aac aaa gac cta aac agc ctt atc gat gct ttc agt aga | 1442 |
| att tca tct aca agt ggc agc gtc tcc cag cag gct ctg cag ttg | 1487 |
| gag agc aaa gcc ttc gat gtc aga gca ggg gca tgg ata aac ggt | 1532 |
| aca gta cct ctg gac agt acc gtc ggc aac gac acg ttc ttt gtt | 1577 |
| atc acc tgg atg gta aaa aag cca gaa atc att ctt caa gat cca | 1622 |
| aaa gga aaa aaa tat aca acc tca gat ttc caa gat gat aaa cta | 1667 |
| aac atc cgg tct gct aga ctt caa ata ccg ggc act gca gag aca | 1712 |
| ggt act tgg act tac agc tac acg ggt acc aag tct cag ttg att | 1757 |
| aca atg aca gtg acc act cga gca aga agt ccc acc atg gaa cca | 1802 |
| ctc ctg ggc tac tgc tac atg agt cag agc aca gcc cag tac cct | 1847 |
| agc cgg atg att gtg tac gca cgg tca gca agg gat ttt gcc cct | 1892 |
| gtt ctg gga gcc aat gtc aca gcc ctc ata gaa gct gaa cat gga | 1937 |
| cat caa gtc acc ttg gag ctc tgg gac aat ggg gca ggt gct gat | 1982 |
| atc gtt aaa aat gat ggc atc tac aca aga tac ttt aca gat tat | 2027 |
| cat gga aat ggt aga tac agc cta aaa gtg cgt gtc cag gca caa | 2072 |
| aga aac aaa acc aga ctg agc tta aga cag aag aac aag tct tta | 2117 |

-continued

```
tat ata cct ggc tat gtg gaa aat ggt aaa att gta ctg aat cca        2162 ccc aga cca gat gtc caa gaa gaa gcc ata gaa gct aca gtg gaa        2207 gac ttc aac aga gta acc tct gga ggg tcg ttt act gtg tct gga        2252 gcg ccc cct gat ggc gac cac gct cgt gtg ttc cca cca agt aaa        2297 gtc aca gac ctg gag gct gag ttt ata ggt gat tat att cac ctt        2342 aca tgg acg gcc cct ggc aag gtt ctc gac aat gga aga gca cat        2387 aga tac atc atc aga atg agc cag cat cct ctg gat ctc caa gaa        2432 gat ttt aac aat gct act tta gtg aat gct tcc agt ctg ata cct        2477 aaa gaa gct ggc tca aaa gaa gca ttt aaa ttc aaa cca gaa act        2522 ttt aaa ata gca aat ggc atc cag ctc tac att gca atc cag gca        2567 gac aat gaa gcc agt ctc acc tct gag gtc tcc aac atc gca cag        2612 gct gtc aag ctt act tct cta gaa gat agt atc tct gca ctg ggt        2657 gat gat att tct gca atc tct atg aca att tgg ggg tta act gtg        2702 att ttt aac tct att tta aac tagaagatag aatggcacta                  2743
aaatgcaatc ctgtacatat ttgctaagtg ttgctttaga atgtctttac             2793
tacacactca aaggctgcct gtcaacaatt gtaatataga agttcatatt             2843
caaagttgaa atcccgagt tactaacaca attcttttgc tatatgtaga              2893
tcaagattaa cagttcctca ttcaatttct taattgttcc atttactatg             2943
gaaataagat atccattctc ttttcacagt gtgatgcaag ttcactttgt             2993
atatgaaaat aaaaaatttg tacaactcg                                    3022
```

<210> SEQ ID NO 34
<211> LENGTH: 902
<212> TYPE: PRT
<213> ORGANISM: Mus musculus

<400> SEQUENCE: 34

```
Met Val Pro Gly Leu Gln Val Leu Leu Phe Leu Thr Leu His Leu
                 5                  10                  15

Leu Gln Asn Thr Glu Ser Ser Met Val His Leu Asn Ser Asn Gly
             20                  25                  30

Tyr Glu Gly Val Val Ile Ala Ile Asn Pro Ser Val Pro Glu Asp
             35                  40                  45

Glu Arg Leu Ile Pro Ser Ile Lys Glu Met Val Thr Gln Ala Ser
             50                  55                  60

Thr Tyr Leu Phe Glu Ala Ser Gln Gly Arg Val Tyr Phe Arg Asn
             65                  70                  75

Ile Ser Ile Leu Val Pro Met Thr Trp Lys Ser Lys Ser Glu Tyr
             80                  85                  90

Leu Met Pro Lys Arg Glu Ser Tyr Asp Lys Ala Asp Val Ile Val
             95                 100                 105

Ala Asp Pro His Leu Gln His Gly Asp Pro Tyr Thr Leu Gln
            110                 115                 120

Tyr Gly Gln Cys Gly Asp Arg Gly Gln Tyr Ile His Phe Thr Pro
            125                 130                 135

Asn Phe Leu Leu Thr Asp Asn Leu Arg Ile Tyr Gly Pro Arg Gly
            140                 145                 150

Arg Val Phe Val His Glu Trp Ala His Leu Arg Trp Gly Val Phe
```

-continued

```
                            155                 160                 165

Asp Glu Tyr Asn Val Asp Arg Ser Pro Tyr Ile Ser Arg Lys Asn
                170                 175                 180

Thr Ile Glu Ala Thr Arg Cys Ser Ala Ser Ile Thr Gly Lys Lys
                185                 190                 195

Val Val His Glu Cys Gln Arg Gly Ser Cys Val Thr Arg Ala Cys
                200                 205                 210

Arg Arg Asp Ser Lys Thr Arg Leu Tyr Glu Pro Lys Cys Thr Phe
                215                 220                 225

Ile Pro Asp Lys Ile Gln Thr Ala Gly Ala Ser Ile Met Phe Met
                230                 235                 240

Gln Asn Leu Asn Ser Val Val Glu Phe Cys Thr Glu Asn Asn His
                245                 250                 255

Asn Ala Glu Ala Pro Asn Leu Gln Asn Lys Met Cys Asn Arg Arg
                260                 265                 270

Ser Thr Trp Asp Val Ile Lys Thr Ser Ala Asp Phe Gln Asn Ala
                275                 280                 285

Pro Pro Met Arg Gly Thr Glu Ala Pro Pro Pro Thr Phe Tyr
                290                 295                 300

Leu Leu Lys Ser Arg Arg Val Val Cys Leu Val Leu Asp Lys
                305                 310                 315

Ser Gly Ser Met Asp Lys Glu Asp Arg Leu Ile Arg Met Asn Gln
                320                 325                 330

Ala Ala Glu Leu Tyr Leu Thr Gln Ile Val Glu Lys Glu Ser Met
                335                 340                 345

Val Gly Leu Val Thr Phe Asp Ser Ala Ala His Ile Gln Asn Tyr
                350                 355                 360

Leu Ile Lys Ile Thr Ser Ser Asp Tyr Gln Lys Ile Thr Ala
                365                 370                 375

Asn Leu Pro Gln Gln Ala Ser Gly Gly Thr Ser Ile Cys His Gly
                380                 385                 390

Leu Gln Ala Gly Phe Gln Ala Ile Thr Ser Ser Asp Gln Ser Thr
                395                 400                 405

Ser Gly Ser Glu Ile Val Leu Leu Thr Asp Gly Glu Asp Asn Gly
                410                 415                 420

Ile Arg Ser Cys Phe Glu Ala Val Ser Arg Ser Gly Ala Ile Ile
                425                 430                 435

His Thr Ile Ala Leu Gly Pro Ser Arg Ala Arg Glu Leu Glu Thr
                440                 445                 450

Leu Ser Asp Met Thr Gly Gly Leu Arg Phe Tyr Ala Asn Lys Asp
                455                 460                 465

Leu Asn Ser Leu Ile Asp Ala Phe Ser Arg Ile Ser Ser Thr Ser
                470                 475                 480

Gly Ser Val Ser Gln Gln Ala Leu Gln Leu Glu Ser Lys Ala Phe
                485                 490                 495

Asp Val Arg Ala Gly Ala Trp Ile Asn Gly Thr Val Pro Leu Asp
                500                 505                 510

Ser Thr Val Gly Asn Asp Thr Phe Phe Val Ile Thr Trp Met Val
                515                 520                 525

Lys Lys Pro Glu Ile Ile Leu Gln Asp Pro Lys Gly Lys Lys Tyr
                530                 535                 540

Thr Thr Ser Asp Phe Gln Asp Asp Lys Leu Asn Ile Arg Ser Ala
                545                 550                 555
```

-continued

```
Arg Leu Gln Ile Pro Gly Thr Ala Glu Thr Gly Thr Trp Thr Tyr
              560                 565                 570

Ser Tyr Thr Gly Thr Lys Ser Gln Leu Ile Thr Met Thr Val Thr
              575                 580                 585

Thr Arg Ala Arg Ser Pro Thr Met Glu Pro Leu Leu Gly Tyr Cys
              590                 595                 600

Tyr Met Ser Gln Ser Thr Ala Gln Tyr Pro Ser Arg Met Ile Val
              605                 610                 615

Tyr Ala Arg Val Ser Gln Gly Phe Leu Pro Val Leu Gly Ala Asn
              620                 625                 630

Val Thr Ala Leu Ile Glu Ala Glu His Gly His Gln Val Thr Leu
              635                 640                 645

Glu Leu Trp Asp Asn Gly Ala Gly Ala Asp Ile Val Lys Asn Asp
              650                 655                 660

Gly Ile Tyr Thr Arg Tyr Phe Thr Asp Tyr His Gly Asn Gly Arg
              665                 670                 675

Tyr Ser Leu Lys Val Arg Val Gln Ala Gln Arg Asn Lys Thr Arg
              680                 685                 690

Leu Ser Leu Arg Gln Lys Asn Lys Ser Leu Tyr Ile Pro Gly Tyr
              695                 700                 705

Val Glu Asn Gly Lys Ile Val Leu Asn Pro Pro Arg Pro Asp Val
              710                 715                 720

Gln Glu Glu Ala Ile Glu Ala Thr Val Glu Asp Phe Asn Arg Val
              725                 730                 735

Thr Ser Gly Gly Ser Phe Thr Val Ser Gly Ala Pro Pro Asp Gly
              740                 745                 750

Asp His Ala Arg Val Phe Pro Pro Ser Lys Val Thr Asp Leu Glu
              755                 760                 765

Ala Glu Phe Ile Gly Asp Tyr Ile His Leu Thr Trp Thr Ala Pro
              770                 775                 780

Gly Lys Val Leu Asp Asn Gly Arg Ala His Arg Tyr Ile Ile Arg
              785                 790                 795

Met Ser Gln His Pro Leu Asp Leu Gln Glu Asp Phe Asn Asn Ala
              800                 805                 810

Thr Leu Val Asn Ala Ser Ser Leu Ile Pro Lys Glu Ala Gly Ser
              815                 820                 825

Lys Glu Ala Phe Lys Phe Lys Pro Glu Thr Phe Lys Ile Ala Asn
              830                 835                 840

Gly Ile Gln Leu Tyr Ile Ala Ile Gln Ala Asp Asn Glu Ala Ser
              845                 850                 855

Leu Thr Ser Glu Val Ser Asn Ile Ala Gln Ala Val Lys Leu Thr
              860                 865                 870

Ser Leu Glu Asp Ser Ile Ser Ala Leu Gly Asp Asp Ile Ser Ala
              875                 880                 885

Ile Ser Met Thr Ile Trp Gly Leu Thr Val Ile Phe Asn Ser Ile
              890                 895                 900

Leu Asn
    902

<210> SEQ ID NO 35
<211> LENGTH: 18
<212> TYPE: DNA
<213> ORGANISM: Artificial sequence
<220> FEATURE:
```

<223> OTHER INFORMATION: Amplification primer

<400> SEQUENCE: 35
gaaccttgcc aggggccg                                                      18

<210> SEQ ID NO 36
<211> LENGTH: 22
<212> TYPE: DNA
<213> ORGANISM: Artificial sequence
<220> FEATURE:
<223> OTHER INFORMATION: Amplification primer

<400> SEQUENCE: 36
ccacgtgctt ctgcgattgc ac                                                 22

<210> SEQ ID NO 37
<211> LENGTH: 31
<212> TYPE: DNA
<213> ORGANISM: Artificial sequence
<220> FEATURE:
<223> OTHER INFORMATION: Amplification primer

<400> SEQUENCE: 37
gcggccgcaa tggggccatt taagagttct g                                       31

<210> SEQ ID NO 38
<211> LENGTH: 30
<212> TYPE: DNA
<213> ORGANISM: Artificial sequence
<220> FEATURE:
<223> OTHER INFORMATION: Amplification primer

<400> SEQUENCE: 38
gcggccgcag ccctaggcta ttgacagctg                                         30

<210> SEQ ID NO 39
<211> LENGTH: 24
<212> TYPE: DNA
<213> ORGANISM: Artificial sequence
<220> FEATURE:
<223> OTHER INFORMATION: Amplification primer

<400> SEQUENCE: 39
agaatcaaga tgaacacaga actc                                               24

<210> SEQ ID NO 40
<211> LENGTH: 26
<212> TYPE: DNA
<213> ORGANISM: Artificial sequence
<220> FEATURE:
<223> OTHER INFORMATION: Amplification primer

<400> SEQUENCE: 40
caaggtattt cacaacttat gacacg                                             26

<210> SEQ ID NO 41
<211> LENGTH: 29
<212> TYPE: DNA
<213> ORGANISM: Artificial sequence
<220> FEATURE:
<223> OTHER INFORMATION: Amplification primer

<400> SEQUENCE: 41
gcggccgcta caacatgacc caaaggagc                                          29

-continued

<210> SEQ ID NO 42
<211> LENGTH: 43
<212> TYPE: DNA
<213> ORGANISM: Artificial sequence
<220> FEATURE:
<223> OTHER INFORMATION: Amplification primer

<400> SEQUENCE: 42
gcggccgcga cactttggat atttatttat aataattttg ttc                43

<210> SEQ ID NO 43
<211> LENGTH: 19
<212> TYPE: DNA
<213> ORGANISM: Artificial sequence
<220> FEATURE:
<223> OTHER INFORMATION: Amplification primer

<400> SEQUENCE: 43
cctttatgtt ttgaatgag                                            19

<210> SEQ ID NO 44
<211> LENGTH: 22
<212> TYPE: DNA
<213> ORGANISM: Artificial sequence
<220> FEATURE:
<223> OTHER INFORMATION: Amplification primer

<400> SEQUENCE: 44
caactatgac atctgcctgg tc                                        22

<210> SEQ ID NO 45
<211> LENGTH: 25
<212> TYPE: DNA
<213> ORGANISM: Artificial sequence
<220> FEATURE:
<223> OTHER INFORMATION: Amplification primer

<400> SEQUENCE: 45
cacaaagcta ggctaagtca agaac                                     25

<210> SEQ ID NO 46
<211> LENGTH: 903
<212> TYPE: PRT
<213> ORGANISM: Unknown
<220> FEATURE:
<223> OTHER INFORMATION: Calcium sensitive chloride channel from bovine
      tracheal epithelium (Cunningham et al., 1995, J. Biol Chem.,
      270:31016-31026)

<400> SEQUENCE: 46

Met Val Pro Arg Leu Thr Val Ile Leu Phe Leu Thr Leu His Leu
                 5                  10                  15

Leu Pro Gly Met Lys Ser Ser Met Val Asn Leu Ile Asn Asn Gly
                20                  25                  30

Tyr Asp Gly Ile Val Ile Ala Ile Asn Pro Ser Val Pro Glu Asp
                35                  40                  45

Glu Lys Leu Ile Gln Asn Ile Lys Glu Met Val Thr Glu Ala Ser
                50                  55                  60

Thr Tyr Leu Phe His Ala Thr Lys Arg Arg Val Tyr Phe Arg Asn
                65                  70                  75

Val Ser Ile Leu Ile Pro Met Thr Trp Lys Ser Lys Ser Glu Tyr
                80                  85                  90

Leu Met Pro Lys Gln Glu Ser Tyr Asp Gln Ala Glu Val Ile Val
                95                  100                 105

-continued

```
Ala Asn Pro Tyr Leu Lys His Gly Asp Asp Pro Tyr Thr Leu Gln
            110                 115                 120

Tyr Gly Arg Cys Gly Glu Lys Gly Gln Tyr Ile His Phe Thr Pro
            125                 130                 135

Asn Phe Leu Leu Thr Asn Asn Leu Pro Ile Tyr Gly Ser Arg Gly
            140                 145                 150

Arg Ala Phe Val His Glu Trp Ala His Leu Arg Trp Gly Ile Phe
            155                 160                 165

Asp Glu Tyr Asn Gly Asp Gln Pro Phe Tyr Ile Ser Arg Arg Asn
            170                 175                 180

Thr Ile Glu Ala Thr Arg Cys Ser Thr His Ile Thr Gly Thr Asn
            185                 190                 195

Val Ile Val Lys Cys Gln Gly Gly Ser Cys Ile Thr Arg Pro Cys
            200                 205                 210

Arg Arg Asp Ser Gln Thr Gly Leu Tyr Glu Ala Lys Cys Thr Phe
            215                 220                 225

Ile Pro Glu Lys Ser Gln Thr Ala Arg Glu Ser Ile Met Phe Met
            230                 235                 240

Gln Ser Leu His Ser Val Thr Glu Phe Cys Thr Glu Lys Thr His
            245                 250                 255

Asn Val Glu Ala Pro Asn Leu Gln Asn Lys Met Cys Asn Gly Lys
            260                 265                 270

Ser Thr Trp Asp Val Ile Met Asn Ser Thr Asp Phe Gln Asn Thr
            275                 280                 285

Ser Pro Met Thr Glu Met Asn Pro Pro Thr Gln Pro Thr Phe Ser
            290                 295                 300

Leu Leu Lys Ser Lys Gln Arg Val Val Cys Leu Val Leu Asp Lys
            305                 310                 315

Ser Gly Ser Met Ser Ser Glu Asp Arg Leu Phe Arg Met Asn Gln
            320                 325                 330

Ala Ala Glu Leu Phe Leu Ile Gln Ile Ile Glu Lys Gly Ser Leu
            335                 340                 345

Val Gly Met Val Thr Phe Asp Ser Val Ala Glu Ile Arg Asn Asn
            350                 355                 360

Leu Thr Lys Ile Thr Asp Asp Asn Val Tyr Glu Asn Ile Thr Ala
            365                 370                 375

Asn Leu Pro Gln Glu Ala Asn Gly Gly Thr Ser Ile Cys Arg Gly
            380                 385                 390

Leu Lys Ala Gly Phe Gln Ala Ile Ile Gln Ser Gln Gln Ser Thr
            395                 400                 405

Ser Gly Ser Glu Ile Ile Leu Leu Thr Asp Gly Glu Asp Asn Glu
            410                 415                 420

Ile His Ser Cys Ile Glu Glu Val Lys Gln Ser Gly Val Ile Ile
            425                 430                 435

His Thr Val Ala Leu Gly Pro Ser Ala Ala Lys Glu Leu Glu Thr
            440                 445                 450

Leu Ser Asp Met Thr Gly Gly His Arg Phe Tyr Ala Asn Lys Asp
            455                 460                 465

Ile Asn Gly Leu Thr Asn Ala Phe Ser Arg Ile Ser Ser Arg Ser
            470                 475                 480

Gly Ser Ile Thr Gln Gln Thr Ile Gln Leu Glu Ser Lys Ala Leu
            485                 490                 495
```

-continued

```
Ala Ile Thr Glu Lys Lys Trp Val Asn Gly Thr Val Pro Val Asp
                500                 505                 510

Ser Thr Ile Gly Asn Asp Thr Phe Phe Val Thr Trp Thr Ile
            515                 520                 525

Lys Lys Pro Glu Ile Leu Leu Gln Asp Pro Lys Gly Lys Lys Tyr
                530                 535                 540

Lys Thr Ser Asp Phe Lys Glu Asp Lys Leu Asn Ile His Ser Ala
                545                 550                 555

Arg Leu Arg Ile Pro Gly Ile Ala Glu Thr Gly Thr Trp Thr Tyr
                560                 565                 570

Ser Leu Leu Asn Asn His Ala Ser Pro Gln Ile Leu Thr Val Thr
                575                 580                 585

Val Thr Thr Arg Ala Arg Ser Pro Thr Thr Pro Pro Val Thr Ala
                590                 595                 600

Thr Ala His Met Asn Gln Asn Thr Ala His Tyr Pro Ser Pro Val
                605                 610                 615

Ile Val Tyr Ala Gln Val Ser Gln Gly Phe Leu Pro Val Leu Gly
                620                 625                 630

Ile Asn Val Thr Ala Ile Ile Glu Thr Glu Asp Gly His Gln Val
                635                 640                 645

Thr Leu Glu Leu Trp Asp Asn Gly Ala Gly Ala Asp Ala Thr Lys
                650                 655                 660

Asp Asp Gly Val Tyr Ser Arg Tyr Phe Thr Thr Tyr Asp Thr Asn
                665                 670                 675

Gly Arg Tyr Ser Val Lys Val His Ala Glu Ala Arg Asn Asn Thr
                680                 685                 690

Ala Arg Leu Ser Leu Arg Gln Pro Gln Asn Lys Ala Leu Tyr Ile
                695                 700                 705

Pro Gly Tyr Ile Glu Asn Gly Lys Ile Ile Leu Asn Pro Pro Arg
                710                 715                 720

Pro Glu Val Lys Asp Asp Leu Ala Lys Ala Glu Ile Glu Asp Phe
                725                 730                 735

Ser Arg Leu Thr Ser Gly Gly Ser Phe Thr Val Ser Gly Ala Pro
                740                 745                 750

Pro Gly Asn His Pro Ser Val Leu Pro Pro Asn Lys Ile Thr Asp
                755                 760                 765

Leu Glu Ala Lys Phe Lys Glu Asp His Ile Gln Leu Ser Trp Thr
                770                 775                 780

Ala Pro Ala Asn Val Leu Asp Lys Gly Lys Ala Asn Ser Tyr Ile
                785                 790                 795

Ile Arg Ile Ser Lys Ser Phe Leu Asp Leu Gln Lys Asp Phe Asp
                800                 805                 810

Asn Ala Thr Leu Val Asn Thr Ser Ser Leu Lys Pro Lys Glu Ala
                815                 820                 825

Gly Ser Asp Glu Asn Phe Glu Phe Lys Pro Glu Pro Phe Arg Ile
                830                 835                 840

Glu Asn Gly Thr Asn Phe Tyr Ile Ala Val Gln Ala Ile Asn Glu
                845                 850                 855

Ala Asn Leu Thr Ser Glu Val Ser Asn Ile Ala Gln Ala Ile Lys
                860                 865                 870

Phe Ile Pro Met Pro Glu Asp Ser Val Pro Ala Leu Gly Thr Lys
                875                 880                 885

Ile Ser Ala Ile Asn Leu Ala Ile Phe Ala Leu Ala Met Ile Leu
```

-continued

```
                    890             895             900
Ser Ile Val
        903

<210> SEQ ID NO 47
<211> LENGTH: 10
<212> TYPE: PRT
<213> ORGANISM: Homo sapiens
<220> FEATURE:
<223> OTHER INFORMATION: partial sequence of human c-myc protein

<400> SEQUENCE: 47

Glu Gln Lys Leu Ile Ser Glu Glu Asp Leu
  1               5                  10
```

NUCLEOTIDE SEQUENCES ENCODING MAMMALIAN CALCIUM ACTIVATED CHLORIDE CHANNEL-ADHESION MOLECULES

This application claims the priority of a Provisional Application Ser. No. 60/065,922 filed on Nov. 17, 1997, which disclosure is herein incorporated herein by reference.

This invention was made with government support under grants CA 47668 and 09682 from the National Cancer Institute. The government has certain rights in the invention.

FIELD OF THE INVENTION

The present invention relates to nucleotide sequences encoding a family of mammalian calcium activated chloride channels which may alternatively, or additionally function as adhesion molecules. More particularly, the invention is directed to genes isolated from bovine endothelial cells, human endothelial cells and murine endothelial cells, which encode calcium activated chloride channel molecules and include the lung-endothelial cell adhesion molecules (Lu-ECAM-1) and associated proteins.

BACKGROUND OF THE INVENTION

Calcium Activated Chloride Channels

Ion channels are not only required for normal cellular functions but also play a critical role in numerous diseased states. For example, cystic fibrosis results when ion transport in epithelial cells of individuals is altered due to a genetic defect of the cystic fibrosis transmembrane conductance regulator (CFTR; Knowles et al., 1983, *J. Clin. Invest.* 71:1410–1417). Although serious airway pathology is usually the primary cause of mortality in young adults with CF, intestinal epithelial alterations have also been observed. However, the severity of tissue lesions does not correlate with the expression of CFTR in humans or mice, suggesting the involvement of cell-specific channels in addition to CFTR. Further support for the involvement of other channel protein molecules in CF comes from observations that calcium activated chloride secretion is preserved in respiratory epithelia of CF patients compared to unaffected individuals, but is significantly reduced or absent from CFTR-defective epithelia. These results strongly suggest that an alternative non-CFTR regulated chloride channel activity might account for attenuating CF disease in some tissues. Thus, a need exists for identification, isolation and functional analysis of alternative chloride channels.

Adhesion Molecules

It is apparent that endothelial cell adhesion molecules may have functions in addition to their adhesive functions. For example, integrins have transmembrane signalling capacities which may play a role in the adherence process. However, the primary function of endothelial cell adhesion molecules is adherence to a substrate such as (a) to promote adherence of endothelial cells to basement membrane, (b) to promote vascular arrest and to facilitate extravasation of leukocytes such as during an immune response, and (c) to promote homing of lymphocytes to a particular lymphoid tissue. Other molecules may play a role in controlling adherence of endothelial cells. For example, chloride ion channels are thought to be involved in a signalling cascade when lymphatic endothelial cells begin to adhere to a substrate (Martin et al., 1996, *Microvasc. Res.* 52:200–9).

There is considerable evidence that metastatic nonlymphoid tumor cells mimic leukocytes in recognizing and adhering to one or more endothelial cell adhesion molecules to migrate in blood vessels, to arrest in vascular areas of organs which may provide the microenvironment conducive for metastatic growth, and to extravasate into surrounding tissues. An example of such an endothelial cell adhesion molecule which promotes adhesion of tumor cells and mediates metastasis is lung-endothelial cell adhesion molecule (Lu-ECAM-1). Lu-ECAM-1 is a 90 kilodalton (kDa) integral membrane protein constitutively expressed primarily in endothelial cells of pleural and subpleural microvessels. Both in vitro studies and in vivo studies indicate that Lu-ECAM-1-expressing endothelial cells promote adhesion of certain lung-colonizing tumor cells in a manner that is consistent with the expression level of the adhesion molecule and the metastatic propensity of tumor cells. For example, in an in vitro tumor cell/endothelial cell adhesion assay, highly lung-metastatic B16-F10 melanoma cells bind to lung-matrix-modulated endothelial cells expressing Lu-ECAM-1 in significantly larger numbers than their intermediate or low lung-metastatic counterparts (B16-L8-F10 and B16F0, respectively; Zhu et al., 1991, *Proc. Natl. Acad. Sci. USA* 88:9568–720). Such binding appears to be calcium ($Ca^{2+}$) dependent. Further, anti-Lu-ECAM-1 monoclonal antibodies significantly inhibit adhesion of B16F10 melanoma cells to Lu-ECAM-1 expressing endothelial cells in culture (Zhu et al., 1991, supra). Anti-Lu-ECAM-1 monoclonal antibodies are also efficient in preventing metastatic colonization of the lungs by highly lung-metastatic B16F10 cells in a standard animal model for metastasis (Zhu et al., 1991, supra). Lu-ECAM-1, affinity purified from detergent extracts of bovine aortic endothelial cells, was used to immunize mice. The immunized mice showed an inhibition of metastatic colonization of the lungs by B16F10 melanoma cells, the efficiency of which was dependent upon the anti-Lu-ECAM-1 serum titer (Zhu et al., 1992, *J. Clin. Invest.* 89:1718–1724). Lu-ECAM-1 appears to be the endothelial cell adhesion molecule for metastatic tumor cells that express the ligand β4 integrin subunit (and possibly other ligands) including, but not limited to, lung-metastatic breast tumor cells, and lung-metastatic melanoma tumor cells.

Anti-adhesion therapy may be used to interfere with adhesion between organ-specific endothelial cells and blood-borne cancer cells in preventing the formation of metastatic colony formation in organs that support metastatic cell growth. The amount of endothelial cell adhesion molecule that can be made from detergent extracts, as well as the rate of production of the endothelial cell adhesion molecule, is generally insufficient for cost-effective commercial production. More efficient production of proteins, with a concomitant reduction in production cost, can often be achieved by producing a protein through recombinant means. In that regard, in some cases a host cell may be genetically engineered such that an increased amount of the protein is produced and/or the protein is produced in a manner which facilitates its isolation (as compared to harvesting the protein from cell membranes).

SUMMARY OF THE INVENTION

It is an object of the invention to provide nucleotide sequences, isolated from mammalian endothelial cells, which encode molecules that function as a calcium activated chloride channel-adhesion molecule (CACC-AM).

It is also an object of the present invention to provide nucleotide sequences which are variants (including portions) of the gene comprising the CACC-AM, and which encode a polypeptide having substantially the biological activity as compared to the biological activity of the CACC-AM.

It is an object of the present invention to provide a means for recombinantly producing CACC-AM molecule.

It is an object of the present invention to provide a means for recombinantly producing proteins associated with CACC-AM molecule.

It is a further object of the present invention to provide expression vectors containing a nucleotide sequence that encodes a CACC-AM molecule; or containing a nucleotide sequence which is a variant of the gene for CACC-AM, and that encodes a polypeptide having substantial biological activity of a CACC-AM; or containing a nucleotide sequence that encodes a protein associated with a CACC-AM.

It is an additional object of the present invention to provide recombinant host cells which contain multiple copies of a nucleotide sequence that encodes a CACC-AM molecule, wherein the CACC-AM molecule is recombinantly produced by culturing the recombinant host cells under suitable conditions.

Other objects, features, and advantages of the present invention will become apparent from the following drawings and detailed description.

BRIEF DESCRIPTION OF THE DRAWINGS

FIG. 8 is a representation of biochemical analysis of the hCLCA2 protein for in vitro translation (a) and immunoblot detection of myc tagged hCLCA2 constructs in HEK293 cells (b).

FIG. 14 is a representation of a comparison of the amino acid sequences of the calcium activated chloride channels, hCLCA1 (SEQ ID NO:27); hCLCA2 (SEQ ID NO:31); bCLCA1 (SEQ ID NO:46); LU-ECAM-1 (SEQ ID NO:1); and mCLCA1 (SEQ ID NO:33).

DETAILED DESCRIPTION

Definitions

Figure 1:
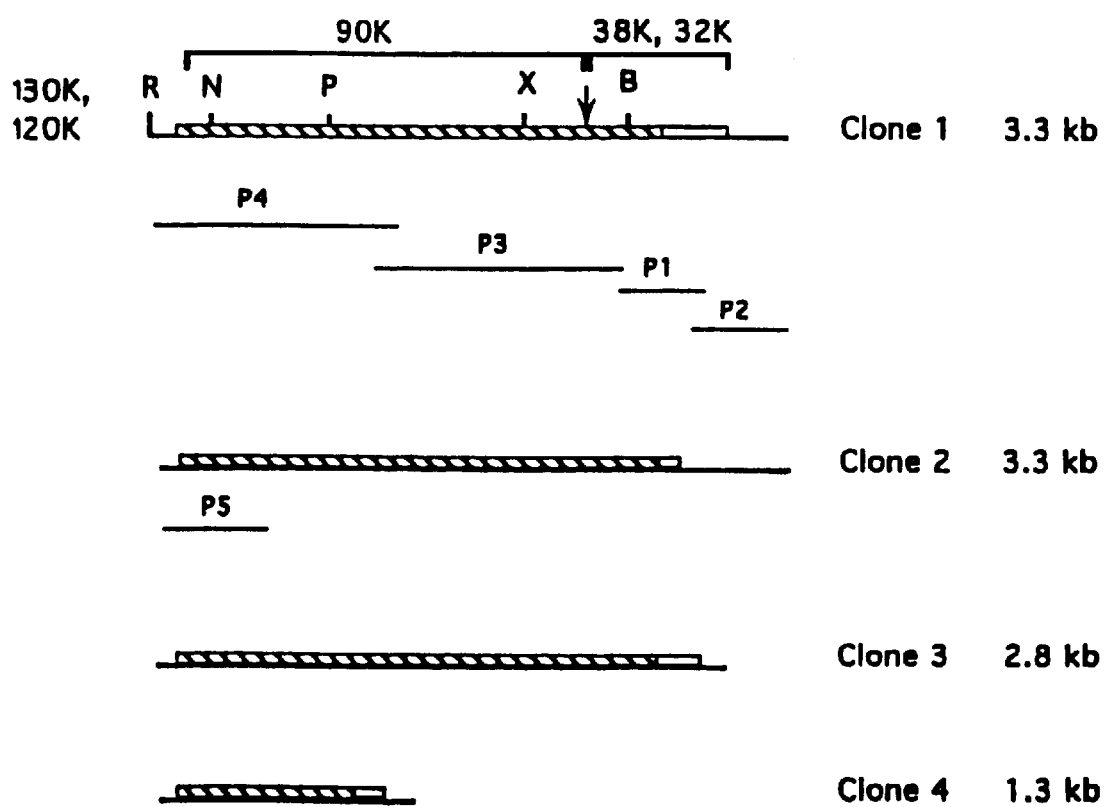
FIG. 1 is a schematic diagram of a method for identifying clones using polymerase chain reaction. Also shown are restriction enzyme sites EcoRI ("R"); NdeI ("N"), PstI ("P"), and BglII ("B").

"Precursor" is a term used in conjunction with "lung-endothelial cell adhesion molecule" hereinafter for the purposes of the specification and claims to refer to a sequence of amino acids bound to and located upstream from the N-terminal portion of the mature form of a lung-endothelial cell adhesion molecule, wherein the removal of this sequence results in the formation of the "mature form" of the lung-endothelial cell adhesion molecule. A precursor protein is a form of a lung-endothelial cell containing a prepro-region. The prepro-region is made up of amino acids comprising a signal sequence, wherein the signal sequence is cleaved to form the mature form of a lung-endothelial cell adhesion molecule.

"Calcium activated chloride channel-adhesion molecule" or "CACC-AM" is a term used hereinafter for the purposes of the specification and claims to mean a molecule isolated from mammalian endothelial cells that when expressed in cells induces the expression of calcium activated chloride conductance channels.

"Calcium activated chloride channel(s)" is a term used for the purposes of the specification and claims to mean chloride channels whose conductance is activated by calcium as judged by inhibition of conductance by DIDS, DTT or niflumic acid.

"Recombinant calcium activated chloride channel-adhesion molecule" or "Recombinant CACC-AM" is a term used hereinafter for the purposes of the specification and claims to refer to a CACC-AM molecule produced from a heterologous cell (e.g., other than from vascular endothelial cells), wherein the heterologous cell has been genetically engineered to contain a nucleotide sequence that encodes a CACC-AM molecule.

"Recombinant calcium activated chloride channel-adhesion molecule-associated protein" or "recombinant CACC-AM-associated molecule" is a term used hereinafter for the purposes of the specification and claims to refer to a CACC-AM associated protein produced from a heterologous cell (e.g., other than from vascular endothelial cells) wherein the heterologous cell has been genetically engineered to contain a nucleotide sequence that encodes a CACC-AM associated molecule. "Lung-endothelial cell adhesion molecule-associated protein" is a term used hereinafter for the purposes of the specification and claims to refer to a protein which (a) is smaller in kilodaltons than the mature form of the lung-endothelial cell adhesion molecule, as determined by, for example, sodium dodecyl polyacrylamide gel electrophoresis (SDS-PAGE) or amino acid analysis; (b) is encoded by messages that also encode the lung-endothelial cell adhesion molecule; (c) is antigenically distinct from the lung-endothelial cell adhesion molecule; and (d) is extracellularly associated in a complex (e.g, specific binding) with the lung-endothelial cell adhesion molecule.

By the term "operably linked" is meant, for the purposes of the specification and claims to refer to the chemical fusion (restriction with subsequent ligation) or synthesis of heterologous DNA with a nucleotide sequence that encodes a lung-endothelial cell adhesion molecule or a lung-endothelial cell adhesion molecule-associated protein such that the resultant recombinant DNA molecule is formed in a proper orientation and reading frame for the nucleotide sequence to be transcribed into functional RNA. In the construction of the recombinant DNA molecule, it is generally preferred to position a promoter at a distance upstream from the initial codon of the nucleotide sequence that is approximately the same as the distance in its natural setting (e.g., in an endothelial cell). However, as known in the art, some variation in the distance can be accommodated without loss of promoter function. Likewise, it is generally preferred to position an enhancer element at a distance upstream from the promoter, or incorporated into the promoter sequences as a promoter element, or located between the promoter and the DNA molecule to be expressed. However, as known in the art, some variation in the placement can be accommodated without loss of the enhancer element's function. "Expression control sequences" is meant, for the purposes of the specification and claims to refer to a promoter or promoter-enhancer combination.

By the term "expression vector" is meant, for the purposes of the specification and claims to refer to a DNA molecule which is operably linked to a nucleotide sequence that encodes one or more recombinant proteins comprising a lung-endothelial cell adhesion molecule and/or a lung-endothelial cell adhesion molecule-associated protein such that the production of the recombinant protein is effected in a suitable host. The vector may include, but is not limited to, a plasmid, phage, or a potential genomic insert.

By the terms "degeneracy substitutions", for the purposes of the specification and claims to refer to the base pair changes (substitutions) in the nucleotide sequence such as a change in one or more bases of a triplet codon (e.g., third base degeneracy) resulting in the encoding of the same amino acid as before the change, or a change resulting in the encoding of a conservative substitution in the amino acid sequence encoded. With respect to such variations, and as appreciated by those skilled in the art, because of third base degeneracy, almost every amino acid can be represented by more than one triplet codon in a coding nucleotide sequence. Thus, in nature or by mutagenic means, the nucleotide sequence be modified slightly in sequence (e.g., substitution of a nucleotide in a triplet codon), and yet still encode its respective gene product of the same amino acid sequence as encoded by the disclosed nucleotide sequences.

Further, the nucleotide sequence may have minor base pair changes which may result in variation (conservative substitution) in the amino acid sequence encoded. Such conservative substitutions are not expected to substantially alter the biological activity of the gene product. A "conservative substitution" for the purpose of the specification and claims means modification of one or more amino acids are such that the tertiary configuration of the recombinant protein is substantially unchanged. Conservative substitutions is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. It is noted that a nucleotide sequence according to the present invention encodes a mammalian Lu-ECAM-1, as to be described more fully herein, and does not encompass the nucleotide sequence encoding the bovine tracheal epithelial chloride channel described recently (Cunningham et al., 1995, *J. Biol. Chem.* 270:31016–26).

By the terms "% identity of amino acid sequence" are meant, for the purposes of the specification and claims to refer to the percent of amino acid positions that are identical between two amino acid sequences as determined by sequence comparisons performed using algorithms known to those skilled in the art.

By the terms "% identity of nucleotide sequence" are meant, for the purposes of the specification and claims to refer to the percent of nucleotide base pair positions that are identical between two nucleotide sequences as determined by sequence comparisons performed using algorithms known to those skilled in the art.

By the term "substantially" is used in conjunction with the biological activity (e.g., adhesive function or chloride ion channel function) to mean, for the purposes of the specification and claims, to refer to retaining a degree of the biological activity ranging from approximately 50% of the activity to greater than 100% of the activity, in relation to the molecule with which it is compared.

By the term "unexpectedly improved" is used in conjunction with the biological activity (e.g., adhesive function or chloride ion channel function) of a recombinant protein to mean, for the purposes of the specification and claims, to refer to a degree of the biological activity which is approximately greater or equal to 30% more biological activity than that of the molecule to which it is compared, and which improvement in activity was unforeseen for this recombinant protein.

The present invention relates to nucleotide sequences and variants thereof that encode a polypeptide which is a calcium activated chloride channel and/or has adhesion properties. In accordance with this invention, nucleotide sequences encoding Lu-ECAM-1/mouse calcium activated chloride channel (mCLCA), and human calcium activated chloride channel molecules (hCLCA1, hCLCA2, and hCLCA3) are disclosed. The nucleotide sequences have been derived from bovine aortic endothelial cells, from murine aortic endothelial cells, or from human endothelial cells. In one embodiment, a nucleotide sequence of the present invention, SEQ ID NO:1, contains sequences that encode either Lu-ECAM-1 or Lu-ECAM-1-associated protein. From SEQ ID NO:1, the lung-endothelial cell adhesion molecule precursor is deduced to be approximately 905 amino acids (SEQ ID NO:2). Cleavage of the signal peptide (amino acids −21 to −1 of SEQ ID NO:2) from the lung-endothelial cell adhesion molecule precursor, and subsequent post-translational processing, results in a Lu-ECAM-1 of about 799 amino acids (amino acid 1 to amino acid 799 of SEQ ID NO:2) and with a predicted molecular size of approximately 87 kDa. It was also discovered during the development of the invention that a SEQ ID NO:1 encodes a Lu-ECAM-1-associated protein (SEQ ID NO:3) which, depending on the glycosylation pattern, has an apparent molecular size (e.g., as determined by SDS-PAGE) ranging from about 22 kDa (little or no glycosylation present) to 38 kDa. More particularly, SEQ ID NO:1 encodes Lu-ECAM-1-associated proteins of apparent molecular size of about 38 kDa and of about 32 kDa. Further, these two LIEU-ECAM-1-associated proteins bind with Lu-ECAM-1 (amino acid 1 to amino acid 799 of SEQ ID NO:2) in forming Lu-ECAM-1 complex. The mCLCA, human CLCA1, and human CLCA2 were then cloned and sequenced using the Lu-ECAM-1 open reading frame as a probe.

In accordance with another embodiment of this invention, using recombinant techniques a nucleic acid molecule containing the nucleotide sequence encoding calcium activated chloride channel-adhesion molecule is incorporated into an expression vector. The recombinant vector is introduced into an appropriate host cell thereby directing the expression of the sequence in that particular host cell. The expression system, comprising the recombinant vector introduced into the host cell, can be used to produce recombinant CACC-AM, or associated proteins. According to the present invention, recombinant CACC-AM, a recombinant polypeptide having CACC-AM activity, and/or recombinant CACC-AM associated protein, can be purified by methods known in the art including ion-exchange chromatography, affinity chromatography, or other chromatographic separation techniques.

Another embodiment of the present invention is a method for providing calcium-activated chloride conductance channels to mammalian cells. In mammalian cells in which the membrane chloride ion channels are deficient in number or function (e.g., in airway epithelial cells of cystic fibrosis patients), a method of providing to mammalian cells a calcium-activated chloride conductance channel, comprising CACC-AM or a polypeptide having CACC-AM activity, comprises administering directly to the cells an expression vector. The expression vector contains a nucleic acid molecule operably linked to expression control sequences, wherein the nucleic acid molecule encodes a CACC-AM, with the resultant expression vector being introduced into the mammalian cell, and the calcium-dependent chloride conductance produced in the mammalian cells containing the expression vector.

The bovine Lu-ECAM-1 complex appears to be expressed in lung, spleen, and aortic epithelial cells. The murine Lu-ECAM-1 complex appears to be expressed in lung, trachea, spleen, mammary gland, intestine, uterus, epididymis, testis, pancreas, kidney, liver and skin. A first human CLCA1 (hCLCA1) molecule (SEQ ID NO:28) appears to be expressed in small intestine, and colon mucosa. A second human CLCA2 (hCLCA2) molecule (SEQ ID NO:32) appears to be expressed in trachea and mammary gland. A third human CLCA3 (hCLCA3) molecule (SEQ ID NO:30) appears to be expressed in small intestine, trachea, mammary gland, stomach, bone marrow, spleen, lymph node, and peripheral blood leukocytes. That these various mammalian proteins appear to be expressed in tissues which are affected in cystic fibrosis may allow them to be used as chloride channels in accordance with Example 8 herein.

For purposes of the description, the following embodiments illustrate the manner and process of making and using the invention and set forth the best mode contemplated by the inventor for carrying out the invention, but are not to be construed as limiting.

EXAMPLE 1

This embodiment illustrates the molecular cloning of calcium activated chloride channel-adhesion molecules. Lu-ECAM-1

A nucleic acid molecule encoding Lu-ECAM-1 and Lu-ECAM-1-associated proteins according to the present invention can be obtained by preparing cDNA from total RNA isolated from a host cell expressing Lu-ECAM-1. To illustrate this example, total RNA was isolated from bovine aortic endothelial cells by the guanidinium chloride procedure, and a Lu-ECAM-1 cDNA clone was constructed using nucleic acid amplification as summarized in FIG. 1. First, the N-terminal and internal amino acid sequences of a 38 kDa Lu-ECAM-1-associated protein (SEQ ID NO:3) were used to design degenerate primers for primary and nested polymerase chain reactions using the reverse-transcribed total RNA as template. Upstream primers corresponded to nucleotide sequences encoding amino acids 685 to 693, and amino acids 698 to 705, of SEQ ID NO:3. Downstream antisense primers corresponded to nucleotide sequences encoding amino acids 839 to 832, and amino acids 852 to 846, of SEQ ID NO:3. A product of approximately 450 bp was amplified (illustrated in FIG. 1 as "P1"). From these sequences, nondegenerate primers (SEQ ID NOs: 4 and 5) were designed, and the resultant amplification for 3' sequences resulted in a product of approximately 750 bp (FIG. 1, "P2"). Nondegenerate primers (SEQ ID NOs: 6 and 7) were designed, and the resultant amplification for 5' sequences resulted in a product of approximately 1000 bp (FIG. 1, "P3"). To obtain the remaining 5' sequences (FIG. 1, "P4") including a signal sequence and the ATG initiation codon, used was an internal primer (SEQ ID NO:8). To reconstitute the cDNA sequence from the amplified products (Pi-P4), the overlapping products were assembled into one open reading frame by an over-lap extension strategy using a high fidelity polymerase combination. The result was clone 1 (FIG. 1) comprising 3.3 kb and encoding the amino acid sequence of SEQ ID NO:2. Hydrophilicity analysis revealed six significant generally nonpolar regions. In particular, a hydrophobic sequence from amino acid 595 to amino acid 618 appears to be a transmembrane domain. Nine potential sites exist for asparagine-linked glycosylation.

Using the primers to probe a lambda cDNA library, three additional clones (clones 2, 3, and 4; FIG. 1) were identified and sequenced. Additional primers (SEQ ID NOs: 9 and 10) were used to obtain the 5' end sequences. Clone 2, a 3.3 kb variant of clone 1, was identical to clone 1 from nucleotide 252 to nucleotide 2438 of SEQ ID NO:1, but then the sequence diverged. The amino acid sequence deduced from clone 2 (SEQ ID NO:11) was identical to that of clone 1 up to amino acid 772 (of SEQ ID NO:2) followed by a glutamate and serine. Clone 3 was 2.8 kb variant of clone 1. The amino acid sequence deduced from clone 3 (SEQ ID NO:12) was identical to that of clone 1 up to amino acid 772 (of SEQ ID NO:2), followed by an additional 28 amino acids. Clone 4, of 1.3 kb, appears to encode a truncated 321 amino acid (SEQ ID NO:13) variant of Lu-ECAM-1 that may be secreted, and is identical in sequence to amino acids 1 to 303 of SEQ ID NO:2, followed by 18 divergent amino acids. An oligonucleotide probe (SEQ ID NO:14) synthesized from the unique 3' region of clone 1 was used to hybridize MRNA isolated from bovine aortic endothelial cells. The probe detected high molecular weight bands (6–10 kb) in Northern blot analysis as well as the 3.3 kb band. However, the probe did not hybridize to the 2.8 and 1.3 kb bands. These results indicate that the 38 kDa and 32 kDa proteins appear to be encoded only by the messages that also encode the 90 kDa protein.

This embodiment also illustrates that CACC-AM is conserved in mammalian species, and thus may serve the same or similar functions in mammalian species other than the ones disclosed herein. Conservation of the gene encoding CACC-AM was determined by multispecies genomic DNA (from human, green monkey, rat, mouse, dog, bovine, rabbit, chicken, and budding yeast) blot with probes derived from various regions of the bovine cDNA sequence for Lu-ECAM-1. These probes hybridized to all mammalian species genomic DNA, although the hybridization to rat DNA was comparatively weak. No hybridization signal was detected for chicken DNA or yeast DNA. These results indicate that the gene (or variant sequence thereof) encoding Lu-ECAM-1 is highly conserved in mammalian evolution.

Accordingly, using similar methods and primer sequences for isolating and sequencing of a nucleotide sequence encoding a bovine Lu-ECAM-1, various nucleotide sequences encoding other CACC-AMs may be identified.

Mouse Calcium Activated Chloride Channel

As an illustration, a murine CACC/AM has been identified. A mouse lung cDNA library in lambda-gt11 was screened with the open reading frame of Lu-ECAM-1 cDNA (EcoR1-BglII 2.4 kb fragment of the Lu-ECAM-1 cDNA) using low stringency hybridization conditions (hybridization at 65 C. in 5×SSC, 5×Denhardt's solution and 0.2% SDS solution overnight with agitation; washing with 2×SSC followed by several washes in 0.2×SSC, 0.2% SDS at room temperature for a total of 30 minutes). Positive phages were purified and analyzed by Southern blot hybridization techniques. Standard sequencing techniques (eg. automatic sequencing techniques) were used to determine the sequence of the clones. The largest of the isolated CDNA was 2.2 kb in length. It lacked the 5' end as determined by sequence comparison with the known bovine homolog. A full length mouse Lu-ECAM-1 was constructed by amplification of the 5' cDNA ends from a pool of mouse lung poly(A)+RNA (CLONTECH). A gene-specific primer (SEQ ID NO:35) was used to reverse transcribe the cDNA from mouse lung mRNA. A nested primer (SEQ ID NO:36) and a primer recognizing the 5'terminal tag were used to amplify the 5' end of the cDNA by polymerase chain reaction. PCR products were cloned into an expression vector (pGEM-3; Promega). A full length mouse mCLCA1 was assembled by fusing the rapid amplification product clone with the 2.2 cDNA insert in an expression vector (pmlI site of pBluescript, Stratagene). Thus a 3.02 kb long sequence (SEQ ID NO:33) encoding a polypeptide of 902 amino acids (SEQ ID NO:34) was obtained.

Human CLCA1

In another illustration, a nucleic acid molecule encoding human calcium sensitive chloride channels was obtained from either the genomic library or a cDNA library. A human genomic library was screened with the ORF of bovine Lu-ECAM-1 as probe using standard plaque hybridization techniques. Three positive clones of 4,6, and 7 kb were isolated and sequenced, spanning a contiguous genomic fragment of 14 kb with interspersed segments of 58 to 65% nucleotide identity to parts of the Lu-ECAM-1 ORF. Since the regions of homology did not encode a contiguous open reading frame and did not cover the entire Lu-ECAM-1 ORF, the remaining parts of the gene were obtained by genomic walking using nested PCR primers from each 5' and 3' end of the clones obtained by plaque hybridizations. Nested PCR conditions were 20 cycles for the first amplification step and 30 cycles for the second amplification with annealing temperatures of approximately 2° C. below the calculated melting point of the primers and extension times of 5 min per cycle. PCR products were cloned into a vector (pGem-T, Promega) and sequenced. The full length gene was isolated and sequenced spanning 31,902 bp. The reading frame of the genomic sequence was determined according to its sequence homology with bCLCA1, Lu-ECAM-1 and mCLCA1.

Using an RT-PCR based strategy, the CLCA1 cDNA was cloned and sequenced from small intestinal mRNA. PCR primers (downstream primer SEQ ID NO:37, and upstream primer SEQ ID NO:38) flanking the ORF and containing linkers with NotI restriction sites were generated and used to amplify the 2745 bp ORF. RT-PCR was performed with 500 ng of human small intestinal poly(A+) (CLONTECH). Reverse transcription was carried out at 48° C. with Superscript RNase H-reverse transcriptase and PCR was performed with Pwo DNA polymerase (Boehringer). PCR conditions were as follows: initial denaturation at 94° C. for 3 min followed by addition of DNA polymerase; 35 cycles of 94° C. for 50 s, 58° C. for 30 s, and 72° C. for 2 min with a time increment of 3 s per cycle for each extension step, followed by a final extension step of 72° C. for 8 min. Foe obtaining the untranslated region of CLCA1 mRNA, amplification of the 5' and 3' ends was carried out using primers SEQ ID NO:39 and SEQ ID NO:40 respectively. The resulting CDNA sequence (SEQ ID NO:27) comprises 3007 bp and is identical to the genomic fragments with high sequence similarity to the previously cloned homolog. It contains a single ORF of 2745 bp encoding a polypeptide of 914 amino acids (SEQ ID NO:28).

hCLCA2 cDNA

A human lung cDNA library (Clontech) was screened using Lu-ECAM-1 cDNA as probe as described above. Missing 5' and 3' ends of the isolated cDNA species were completed using RACE (Life Technologies). A single 3.6 kb cDNA species was identified and termed CLCA2. A sequence of 2970 bp is shown in SEQ ID NO:31. The open reading frame of The nucleotide sequence encoding a polypeptide of 943 amino acids (SEQ ID NO:32) shared high degrees of identity with those of Lu-ECAM-1 (86%), bCLCAl (85%), mCLCAl (76%), and hCLCAI (63%)—FIG. 14.

hCLCA3 cDNA

A human spleen CDNA library packed in phage λgt11 (Clontech) was screened using standard plaque hybridization protocols. The open reading frame (ORF) of the Lu-ECAM-1 cDNA was used as probe as described above. Phage colony blots were hybridized and washed at low stringency conditions (hybridization: 55° C. overnight in 4×SSC standard hybridization buffer without formamide; two stringency washes with 2×SSC, 0.1% SDS at room temperature, and two washes with lxSSC, 0.1% SDS at 40° C.). After exhaustive screening of the library ($>7 \times 10^6$ plaques), a single positive phage clone was plaque-purified, amplified, and subjected to DNA purification (Wizard Lambda Preps, Promega). The insert was cut out using the EcoRI sites and cloned into pbluescript II SK (Stratagene). Automated sequencing with initial plasmid-derived primers followed by internal gene-specific primers was performed by the Cornell University DNA Sequencing Facility using dRhodamine Terminator Cycle Sequencing on an ABI Prism 377 DNA Sequencer (PE Applied Biosystems). Missing 5' and 3' ends of the cDNA were isolated using the rapid amplification of cDNA ends (RACE) technique (Life Technologies) and human spleen poly-A+RNA (Clontech) as template. The primers for amplification of 5' end were SEQ ID NO:43 and SEQ ID NO:44, and the primers for 3' end was SEQ ID NO:45. The resulting cDNA sequence of 3599 base paris (deposited in GenBank under accession no. AF043976) was obtained. A sequence of 3418 bp is shown in SEQ ID NO:29, which encodes for a polypeptide of 1000 amino acids (SEQ ID NO:30).

EXAMPLE 2

This example illustrates the proteins encoded by the cDNAs isolated in Example 1 and the relationship between CACC-AM and associated proteins. As an illustration, the relationship is between Lu-ECAM-1 and Lu-ECAM-1 associated protein is demonstrated. Antigenic characterization was performed by generating anti-Lu-ECAM-1 antibodies, and testing the antibodies in Western blot analyses of bovine aortic endothelial cell extracts. Rats were immunized with either the 90 kDa band excised from a polyacrylamide gel and mixed with adjuvant, resulting in polyclonal antibody R4; or a 38 kDa band excised from a polyacrylamide gel and mixed with adjuvant, resulting in polyclonal antibody R41. Two peptides (SEQ ID NOs: 15 and 16) were synthesized, conjugated to KLH, and used to immunize rabbits in forming polyclonal antibodies CU11 and CU8, respectively. Monoclonal antibody 6D3 has binding specificity to Lu-ECAM-1 as described previously (Zhu et al., 1992, supra).

Figure 2A:
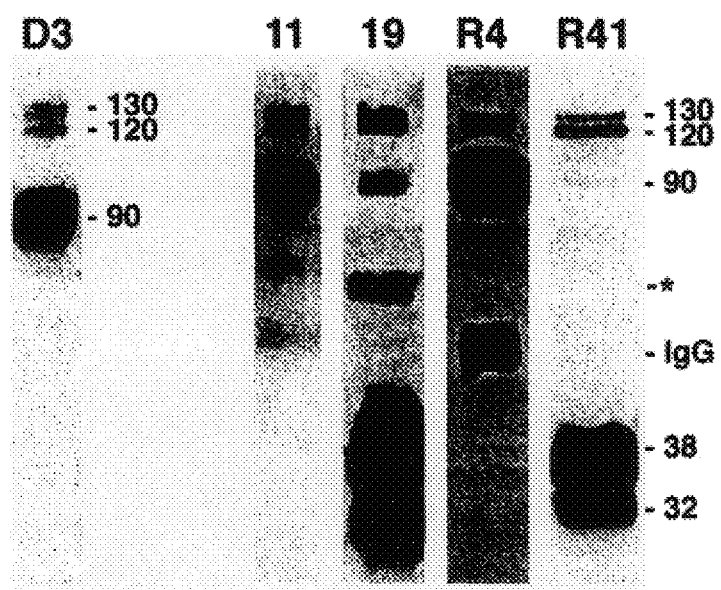
FIG. 2A is a representation of immunoblots of bovine aortic endothelial cell proteins using either monoclonal antibody D3 ("D3"), polyclonal antibody CU11 ("11"), polyclonal antibody CU19 ("19"), polyclonal antibody R4 ("R4"), and polyclonal antibody R41 ("R41").

As shown in FIG. 2A, mAb 6D3 detected a 90 kDa component (Lu-ECAM-1) and two larger bands of approximately 120 kDa and 130 kDa (Lu-ECAM-1 precursors); but not the 38 kDa or the 32 kDa components (Lu-ECAM-1-associated proteins). Likewise, polyclonal antibody (against amino acid residues of SEQ ID NO:15) recognized only the 90 kDa, 120 kDa, and 130 kDa components (FIG. 2A). In contrast, polyclonal antibody CU19 (against amino acid residues 618 to 767 of SEQ ID NO:2) strongly detected the 38 kDa and 32 kDa components, and the 120 kDa and 130 kDa components, but only weakly detected the 90 kDa component. These results are evidence that the initial translation products of the open reading frame in SEQ ID NO:1 are the 120 kDa and 130 kDa components, which are then processed to yield the 90 kDa, 38 kDa, and 32 kDa components.

Figure 2B:
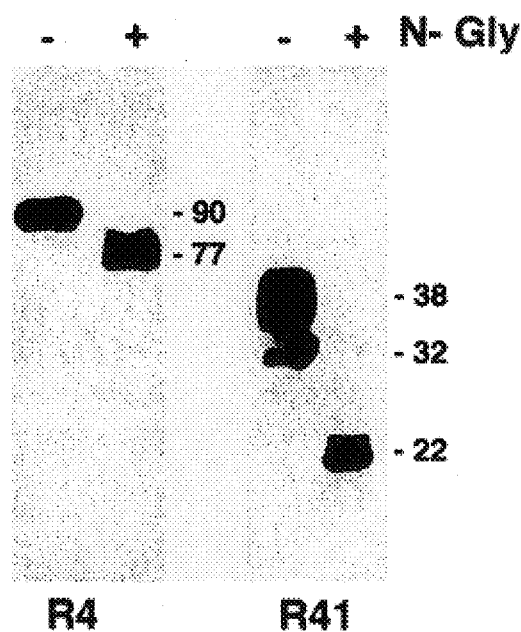
FIG. 2B is a representation of Lu-ECAM-1 untreated ("−") or Lu-ECAM-1 treated with N-glycosidase F ("+") followed by immunoblot analysis using polyclonal antibody R4; and Lu-ECAM-1-associated proteins untreated ("−") or Lu-ECAM-1-associated proteins treated with N-glycosidase F ("+") followed by immunoblot analysis using polyclonal antibody R41.

These results were confirmed with polyclonal antibodies R4 and R41. R4, a polyclonal anti-90 kDa protein antibody, detected the 90 kDa band, as well as the 120 kDa and 130 kDa components; but not the 38 kDa, and 32 kDa components (FIG. 2A). R41, a polyclonal anti-38 kDa protein antibody, detected the 38 kDa and 32 kDa bands, as well as the 120 kDa and 130 kDa components; but not the 90 kDa component (FIG. 2A). These results indicate that (a) the 38 kDa and 32 kDa bands are antigenically related; (b) the 120 kDa and 130 kDa bands are antigenically related; and (c) the 120 kDa and 130 kDa bands have sequence in common with both the 90 kDa protein, and the 38 kDa and 32 kDa proteins. Treatment of Lu-ECAM-1 complex with Nglycosidase F reduced the 38 kDa and 32 kDa components to a common band of about 22 kDa, indicating the these two proteins represent alternate glycoforms (FIG. 2B). N-glycosidase F treatment reduced the 90 kDa protein to 77 kDa (FIG. 2B). The 77 kDa and 22 kDa products would add up to the exact size of the initial translation product of clone 1 before processing.

Figure 3A:
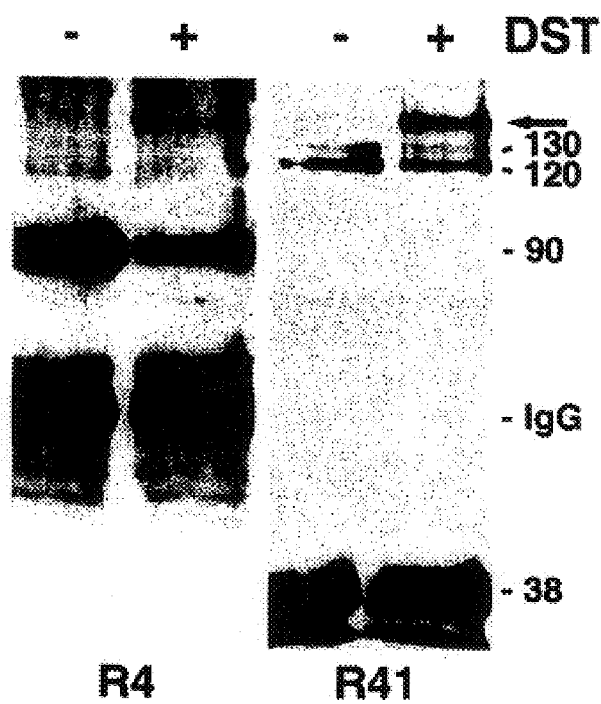
FIG. 3A is a representation of bovine aortic endothelial cells either untreated ("−") or treated with a crosslinker ("+") followed by immunoblot analysis using either polyclonal antibody R4 ("R4"), or polyclonal antibody R41 ("R41").
Figure 3B:
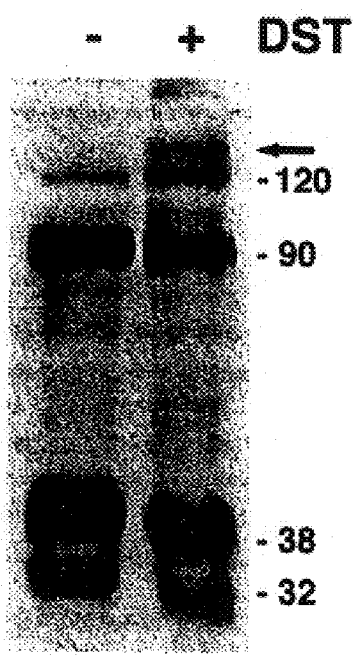
FIG. 3B is a representation of bovine aortic endothelial cells which were surface-biotinylated in the absence of ("−") or presence of ("+") a crosslinker followed by detection with streptavidin-horseradish peroxidase.

As shown in FIG. 2A, the 38 kDa and the 32 kDa components of the Lu-ECAM-1 complex are not recognized by mAb 6D3 in SDS-PAGE and Western blot analysis, suggesting that these components are likely noncovalently complexed with the 90 kDa protein. The Lu-ECAM-1 complex is resistant to dissociation by high salt, detergent, and EDTA, but readily dissociates when boiled in SDS in the presence or absence of reducing agents (e.g., dithiothrietol). To visualize the Lu-ECAM-1 complex, and to determine whether the proteins of the complex are associated intracellulary or extracellularly, the surface of bovine aortic endothelial cells was cross-linked. Confluent bovine aortic endothelial cells were surface biotinylated in the presence or absence of disuccinimidyl tartarate (DST), a reagent that restricts cross-linking to extracellular moieties of proteins in close contact. DST dissolved in dimethyl sulfoxide was added to the cells in a final concentration of 1 mM. Cross-linking was carried out at 4° C. with gentle shaking. The reactions were stopped by adding glycine to a final concentration of 50 mM. After quenching for 5 minutes, the cells were lysed for 1 hour in lysis buffer. Lysates were clarified by centrifugation, precipitated with mouse-IgG agarose beads, then immunoprecipitated with mAb 6D3. Immunoprecipitated proteins were analyzed by SDS-PAGE, transferred to nitrocellulose, and detected using avidin-horseradish peroxidase and chemiluminescence. As shown in FIG. 3A, immunoblots using either R4 (polyclonal anti-90 kDa protein antibody) or R41 (polyclonal anti-38 kDa protein antibody) detected a novel band migrating at approximately 140 kDa (arrow, FIG. 3A), with a concomitant reduction in intensities of the 90 kDa, 38 kDa, and 32 kDa components. As illustrated in FIG. 3B, all Lu-ECAM-1 complex components were biotinylated on bovine aortic endothelial cell surface. These results suggest that the Lu-ECAM complex is made up of either the 90 kDa and 38 kDa proteins complexed in an extracellular association, and/or the 90 kDa and 32 kDa proteins complexed in an extracellular association.

Figure 6:
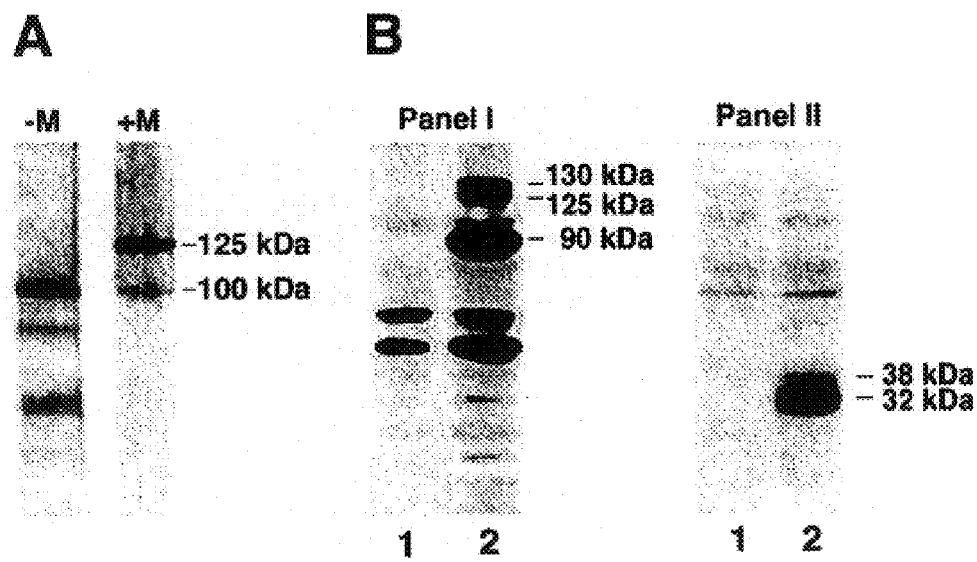
FIG. 6 is a representation of the expression of mCLCA1 by in vitro translation (A) and in transfected HEK293 cells (B).

In another illustration of this embodiment, the mCLCA1 protein was characterized. An in vitro transcription and translation system (TNT™, Promega) was used for the in vitro expression of the full length cDNA (SEQ ID NO:33). Canine microsomes were used to glycosylate the product of in vitro translation. In addition, HEK293 cells were transfected with the cDNA of mCLCA1 using standard methods known to those skilled in the art (CaPO$_4$ or Lipfectamine, Life Technologies). Products were analyzed on SDS-PAGE gels. In addition, mCLCA1 cDNA was also used for transfection of cells. Proteins prepared by standard in vitro translation techniques or from lysates of transfected HEK293 cells were analyzed on Western blotting by using rabbit polyclonal antibodies against N-terminal (CU8) and the C-terminal region (CU21) of Lu-ECAM peptide. As shown in FIG. 6, protein bands of 130, 125, 90 kDa and triplet bands of 32–38 kDa were detected in transfected cells. CU8 reacted exclusively with the large sized bands of 90, 125 and 130 kDa whereas CU21 reacted with only the triplet of the smaller bands. This recognition pattern is similar to that observed for Lu-ECAM-1 and suggests that the ORF of mCLCA1 cDNA encodes a precursor protein, represented by alternate glycoforms of 125 and 130 kDa, that is posttranslationally processed into 90 kDa and 38/32 kDa components.

Figure 7:
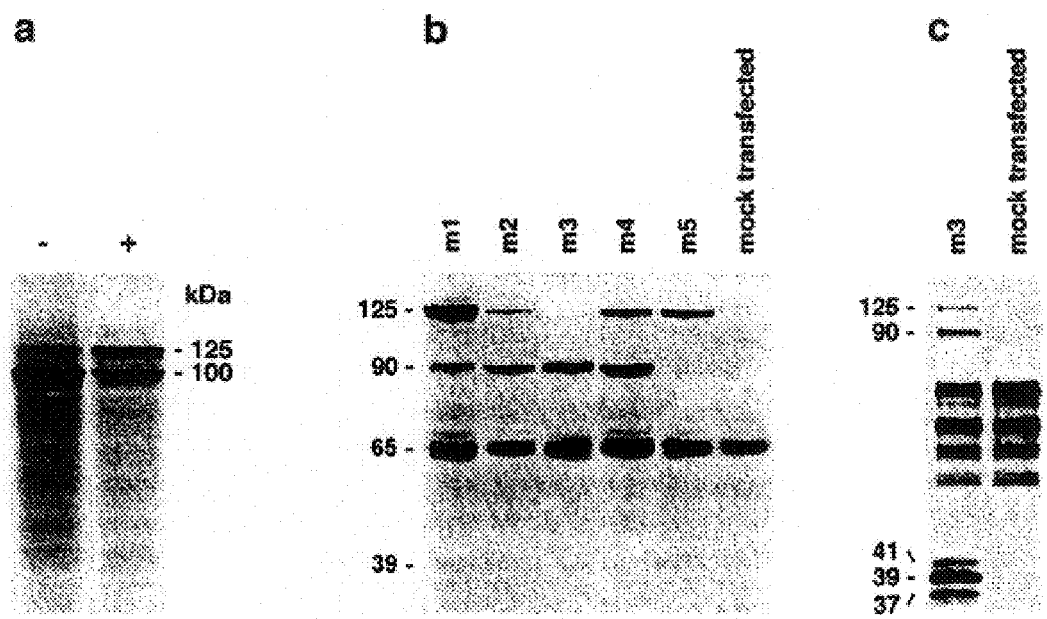
FIG. 7 is a representation of the biochemical analysis of hCLCA1 protein for in vitro translated (a), c-myc tagged hCLCA1 transfected HEK293 (b), and surface expression of c-myc tagged hCLCA1.

In another illustration of this embodiment, the hCLCA1 protein was characterized. The ORF of the hCLCA1 cDNA encodes a 914 amino acid protein with a calculated molecular weight of 100.9 kDA. In vitro translation of human CLCA1 cDNA yielded a single protein of approximately 100 kDa, consistent with its calculated size (FIG. 7). In the presence of canine microsomes the Mr of the polypeptide shifted to 125,000 indicating multiple glycosylations. Similar to Lu-ECAM-1 and mCLCA1, 37–40 kDa proteins were not detected in immunoblots of whole cell lysates but were coimmunoprecipitated with the 90 and 125 kDa protein. To ascertain whether the 125 kDa hCLCA1 protein is processed into 90 kDa and 30–40 kDa cleavage products in a manner similar to Lu-ECAM-1, c-myc tags were inserted in five different hydrophilic sites with high surface probability (m1–m5) and were overexpressed in HEK293 cells (Cravchik et al., 1993, *Gene* 137:139–143). Immunoblots of whole cell lysates probed with anti-myc antibodies revealed proteins of 125 and 90 kDa (FIG. 7b). However, immunoprecipitation of cell lysates following surface biotinylation indicated the presence of 37–41 kDa proteins similar to Lu-ECAM-1 and mCLCA1 (FIG. 7c).

In another illustration of this embodiment, the human CLCA2 protein was analyzed. The predicted size of the full length protein (104 kDa) is consistent with the result of an in vitro translation assay yielding primary translation product of approximately 105 kDa (FIG. 8a). To ascertain wheter the CLCA2 protein is cleaved into two subunits in mammalian cells as reported for other CLCAs, two constructs were generated with a c-myc tag within the amino or carboxy terminus respectively as described by Cravchik et al., 1993, *Gene* 137:139–143) and transfected into HEK293 cells. Immunoblots of cell lysates probed with anti-myc antibody identified an 86 kDa protein when the tag was inserted near the amino terminus (m1) and a 34 kDa protein when the tag was inserted near the amino terminus (m2)—FIG. 8b.

EXAMPLE 3

Tissue Distribution

This example illustrates the tissue distribution of CACC-AM. As an illustration, the distribution of Lu-ECAM-1/Lu-ECAM-1 complex in the respiratory tree, as demonstrated by immunohistochemistry. Tissue sections were probed with anti-Lu-ECAM-1 antibodies. Formalin-fixed sections of bovine trachea were first denatured by boiling for ten minutes in 4M urea in a microwave oven, then probed with polyclonal antibody R4 (raised against denatured Lu-ECAM-1). The sections were then incubated with donkey anti-rat IgG and avidin-peroxidase conjugate. The peroxidase conjugate was detected using diamino-benzidine as substrate, and then the slides were counterstained with hematoxylin. Lung sections were prepared and probed with mAb 6D3 as previously described (Zhu et al., 1993, *Int. J. Cancer* 53:628–633) except that a biotinylated secondary antibody was used, followed by the avidin-peroxidase conjugate, diamino-benzidine as substrate, and counterstaining with hematoxylin. The immunohistochemical analyses revealed that Lu-ECAM-1/Lu-ECAM-1 complex was expressed predominantly in endothelia of small to medium-size venules of the lung, and in the respiratory epithelia of bronchi and trachea. To confirm the distribution of expression of Lu-ECAM-1/Lu-ECAM-1 complex, and to distinguish it from that of the bovine epithelial chloride channel ("Ca-CC") described recently (Cunningham et al., 1995, supra), nucleic acid amplification was performed using specific primers as described herein in Example 4.

Tissue distribution for other CACC-AMs of the present invention were determined by Northern blot analysis and RT-PCR. Human multiple tissue Northern blots (Clontech) contained 2 μg poly-A+RNA per lane of the following tissues: heart, brain, placenta, lung, liver, skeletal muscle, kidney, pancreas, spleen, thymus, prostate, testis, ovary, small intestine, colon mucosa, peripheral blood leukocytes, stomach, thyroid, spinal cord, lymph node, trachea, adrenal gland, and bone marrow. Blots were hybridized labeled fragments for respective cDNAs. To exclude cross hybridization of related family members, highly stringent washing conditions were employed following the hybridization (two washes with 2×SSC, 0.1% SDS at 65° C. for 30 min, followed by two washes with 0.2×SSC, 0.1% SDS at 65° C. for 30 min). RT-PCR was performed using the above-mentioned conditions and primers to detect the cDNA fragments in poly-A+RNA samples from human tissues. PCR products were analyzed on an ethidium bromide stained agarose gel. To exclude amplification of a closely related family member, the PCR products were cut out of the gel, cloned into the pGem-T vector, and partially sequenced. In all RT-PCR assays, negative controls were included with water instead of RNA as template in the reverse transcription. To control for RNA quality as well as reverse transcription and PCR conditions, a fragment of EF-1a mRNA was amplified as described.

A mouse multiple tissue Northern blot when probed with HindIII fragment of mCLCA1 ORF revealed the presence of a 3.1 kb transcript in brain and spleen and transcripts of 5 kb and 3.1 kb in heart, lung, liver, and kidney.

For human CLCA1, a single mRNA species of 3.3 kb was detected in Northern blot hybridizations in small intestine and colon mucosa. Similar results were obtained with RT-PCR.

hCLCA2 mRNA was detected in trachea and mammary gland, using the 2832 ORF of hCLCA1. While CLCA2 was not detected in the lung by Northern blot hybridization, the more sensitive RT-PCR revealed its expression in lung in addition to trachea and mammary gland suggesting a significantly lower expression level in the lung.

No signals were detected in any of the tissues tested on Northern blots using the 2817 cDNA of hCLCA3. However, by RT-PCR a fragment of the hCLCA3 cDNA could be amplified form all tissues tested, i.e. spleen, lung, trachea, thymus and mammary gland.

EXAMPLE 4

This example demonstrates that Lu-ECAM-1 and the bovine epithelial chloride channel ("Ca-CC") described recently by (Cunningham et al., 1995, *J. Biol. Chem.* 270:31016–31026) are distinct molecules.

1. Genetic Similarity

Sequence alignment of the open reading frame of SEQ ID NO:1 with the CA-CC cDNA shows that the nucleotide sequences share 92% identity at the DNA level. Comparing the deduced amino acid sequence of Lu-ECAM-1 (SEQ ID NO:2) with that of CA-CC shows 88% identity at the amino acid level. However, the differences appear randomly distributed, and thus, Lu-ECAM-1 and CA-CC appear to represent products of different genes.

2. Subunit Differences

As shown in FIGS. 2A, 2B, 3A, and 3B, it is clear that the precursor Lu-ECAM-1 is a protein with an apparent molecular size of either 120 kDa or 130 kDa. The precursor Lu-ECAM-1 gets processed to a 90 kDa Lu-ECAM-1 protein, and to either a 38 kDa or 32 kDa Lu-ECAM-1-associated protein. In contrast, CA-CC is a 140 kDa multimeric complex that can be reduced to a band comprised of 38 kDa subunits in the presence of a reducing agent (Cunningham et al., 1995, supra). This difference in subunit structure is further evidence that Lu-ECAM-1/Lu-ECAM-1 complex is a glycoprotein distinct from CA-CC.

3. Molecular Expression Differences

It is possible that immunohistochemical staining with polyclonal antibody to Lu-ECAM-1 could detect CA-CC if CA-CC shared a cross-reactive epitope with Lu-ECAM-1. To distinguish Lu-ECAM-1 expression from CA-CC expression in tissues, reverse transcriptase polymerase chain reaction was performed. Messenger RNA (500 ng) from bovine lung tissue, from bovine spleen tissue, from bovine tracheal epithelium, and from cultured bovine aortic endothelial cells was reverse-transcribed with random oligonucleotide primers and reverse transcriptase in a 20 µl reaction volume. Primers specific for Lu-ECAM-1 sequences (primer pairs "L1": SEQ ID NOS: 17 and 18, "L2": SEQ ID NOs: 19 and 20), and primers specific for CA-CC sequences (primer pairs "T1":SEQ ID NOs: 21 and 22, and "T2" SEQ ID NOs: 23 and 24) were confirmed for selectivity by control experiments with a Lu-ECAM-1 cDNA clone. Amplification was performed using 1 µl of the respective cDNA substrate for 35 cycles of amplification in a reaction volume of 50 µl using 0.5 units of thermostable DNA polymerase, 200 µM of each dNTP, 1,5 mM $MgCl_2$, and 1 µM of the respective primer pair. The cycling protocol was 94° C. for 20 seconds, 55° C. for 10 seconds, and 72° C. for 10 seconds, with a time increment of 2 seconds per cycle for annealing and extension times. A final extension step was performed at 72° C. for 10 minutes. Aliquots (5 µl) of each amplification reaction was fractionated on a 1.5% agarose gel, and stained with ethidium bromide.

Figure 4A:
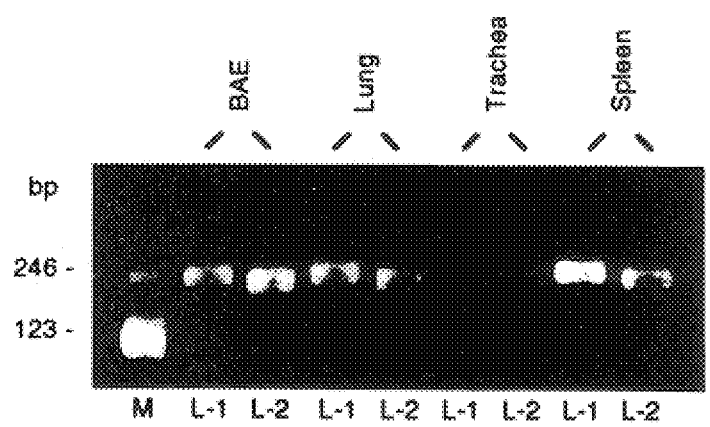
FIG. 4A is a representation of a ethidium bromide stained agarose gel containing the results of reverse transcriptase polymerase chain reaction analysis of bovine aortic endothelial cells ("BAEC"), lung tissue, tracheal epithelium, and spleen tissue using Lu-ECAM-1 specific primer pairs L1, and L2.
Figure 4B:
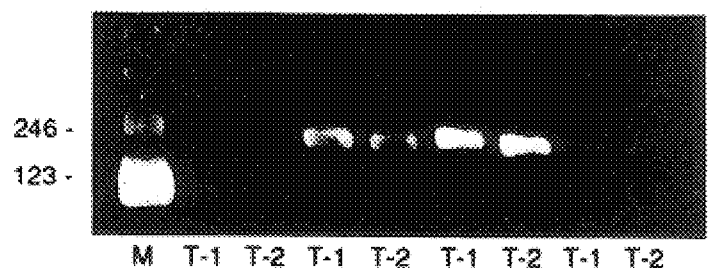
FIG. 4B is a representation of a ethidium bromide stained agarose gel containing the results of reverse transcriptase polymerase chain reaction analysis of bovine aortic endothelial cells ("BAEC"), lung tissue, tracheal epithelium, and spleen tissue using bovine tracheal chloride channel ("Ca-CC") specific primer pairs T1, and T2.

The calculated size for product amplified using primer pair L1 is 232 bp; the calculated size for product amplified using primer pair L2 is 218 bp; the calculated size for product amplified using primer pair T1 is 231 bp; and the calculated size for product amplified using primer pair T2 is 218 bp. As shown in FIG. 4A, Lu-ECAM-1 is expressed in bovine aortic endothelial cells, lung tissue, and spleen, tissue, but not in tracheal epithelium. In contrast, as shown in FIG. 4B, CA-CC is expressed in lung tissue and tracheal epithelium, but not in bovine aortic endothelial cells nor spleen tissue. These results further support that Lu-ECAM-1 and CA-CC are different molecular entities, with Lu-ECAM-1 being expressed in venular endothelial cells, and CA-CC being expressed in tracheal and bronchial epithelial cells.

EXAMPLE 5

This embodiment illustrates that a nucleic acid molecule comprising a nucleotide sequence encoding CACC-AM, or a variant sequence thereof, or encoding one or more CACC-AM associated proteins, can be inserted into various vectors including phage vectors and plasmids. Successful expression of the protein(s), requires that either the insert comprising the nucleotide sequence, or the vector itself, contain the necessary elements for transcription and translation (expression control elements) which is compatible with, and recognized by the particular host system used for expression. A variety of host systems may be utilized to express the recombinant protein(s), which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the nucleic acid molecule encoding the recombinant protease, to increase the expression of the recombinant protein(s), provided that this increased expression is compatible with (for example, non-toxic to) the particular host cell system used. The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene or the variant sequence and expression into the recombinant protein. For example, bacterial, phage, or plasmid promoters known in the art from which a high level of transcription has been observed in a host cell system comprising E. coli include the lac promoter, trp promoter, tac promoter, reca promoter, ribosomal RNA promoter, the PR and PL promoters, lacUV5, ompf, bla, lpp, and the like, may be used to provide transcription of the inserted DNA sequence encoding the recombinant protein.

As known to those skilled in the art, such vectors for expression in mammalian cells can be selected from plasmids, viruses, and retroviruses. For a recent review of vectors useful in gene therapy, see Weichselbaum and Kufe (1997, Lancet, 349:S10–S12). The features of a vector which make it useful in the methods of the present invention include that it have a selection marker for identifying vector which has inserted therein the nucleotide sequence to be expressed; restriction sites to facilitate cloning; and the ability to enter and/or replicate in mammalian cells. Examples of a preferred vector for the in vivo introduction of a recombinant vector into mammalian cells include, but are not limited to viral vectors. Virus-based vectors are one preferred vehicle as they infect cells in vivo, wherein during the infection process the viral genetic material is transferred into the cells. A retroviral vector, such as a plasmid containing AAV (Adeno-associated virus) sequences, has been described previously (see for example Chatterjee et al., 1992, Science, 258:1485–1488; U.S. Pat. No. 5,252,479, herein incorporated by reference). Examples of other vectors for the in vitro or in vivo introduction into mammalian cells include retroviral vectors (Miller et al., 1989, BioTechniques 7:980–990; Korman et al., 1987, Proc. Natl. Acad. Sci. USA 84:2150–54), papovavirus episomes (U.S. Pat. No. 5,624, 820, herein incorporated by reference), and adenovirus vectors (U.S. Pat. No. 5,585,362, herein incorporated by reference). Promoters are known to those skilled in the art, and may include viral or viral-like basal promoters like the SV40 late promoter, the RSV promoter, the CMV immediate early promoter, and a VL30 promoter; and cellular promoters (See, e.g., Larsen et al., 1995, Nucleic Acids Res. 23:1223–1230; Donis et al., 1993, BioTechniques 15:786–787; Donda et al., 1993, Mol. Cell. Endocrinol. 90:R23–26; and Huper et al., 1992, In Vitro Cell Dev. Biol. 28A:730–734).

In one illustration of this embodiment, a nucleotide sequence comprising clone 1 (SEQ ID NO:1) was placed under the control of a tetracycline-regulated promoter in a commercially available plasmid (pTet-Splice; GIBCO). The construction was accomplished in two steps. An amplified product was generated that corresponded to the 3' end of clone 1 cDNA (nucleotide 2391 to nucleotide 2780 of SEQ ID NO:1) using a 5' primer containing an EcoRI restriction site (SEQ ID NO:25) and a 3' primer containing a SpeI restriction site (SEQ ID NO:26). The cycling protocol included 93° C. for 35 seconds, 55° C. for 60 seconds, 72° C. for 3 minutes for 40 cycles followed by a 10 minute incubation at 72° C. using a thermostable DNA polymerase. The product was cleaved with EcoRI and SpeI, then cloned into corresponding restriction sites in the plasmid. The resultant plasmid was selected and then sequenced to confirm absence of mutations. This recombinant plasmid was then cleaved with EcoRI and BglII. To reconstitute the open reading frame encoding Lu-ECAM-1, the 2.3 kb EcoRI/BglII fragment was excised from clone 3 and inserted into the plasmid. The resulting plasmid, pTet-Splice-Lu-ECAM-1, was then co-transfected into HEK293 cells with another plasmid (pTet-tTAK) that encodes a transcriptional activator specific for the pTet-Splice vector. Transfection was done using a transfection reagent (lipofectamine) according to the manufacturers instructions. Cells were harvested 24 hours after the start of transfection. Immunoblot analysis of the cells using polyclonal R41 resulted in the detection of recombinant Lu-ECAM-1 precursor of 120 kDa, and recombinant Lu-ECAM-1-associated protein of 38 kDa. When the cells were probed in immunoblot with anti-peptide antibody CU8, detected was recombinant Lu-ECAM-1 precursor of 120 kDa, and recombinant Lu-ECAM-1 of 90 kDa.

In another embodiment of the invention, mCLCA1 cDNA was cut from the pBluescript vector (Stratagene) with SacI and PvuI, blunt ended with Klenow Polymerase and inserted into the tetracycline sensitive mammalian expression vector (pTet-splice, Life Technologies, Inc.) at the EcoRV site. HEK293 cells were cotransfected with mCLCA1 cDNA cloned into the pTet-splice alon with a vector expressing a tetracycline activator (pTet-tTak) using standard transfection techniques well known to those skilled in the art and as described above (Lipofectamine, Life Technologies, Inc.). Cells were cotransfected with a reporter vector as described above. In another illustration of this embodiment, human CLCA1, HEK293 cells were transfected with either pcDNA 3.1 containing the CLCA1 insert and a reporter vector (enhanced green fluorescent protein, EGFP, CLONTECH) or the reporter vector alone. Trnasfection can be carried out by standard techniques known to those skilled in the art including CaPO4 precipitation or Lipofectamine (Life Technologies).

For human CLCA2, HEK293 cells were transfected using Lipofectamine using manufacturer's instructions. For example, 5 ul lipid and 0.5 ul of CLCA2 were cloned into pcDNA 3.1 per 35 mm well in a 2–3 hour incubation. For expression studies, the 2,832 bp CLCA2 ORF was PCR amplified from human trachea poly-A$^+$ RNA (Clontech) following reverse transcription with Superscript RNase H$^-$ reverse transcriptase (Life Technologies) and random hexamer priming. PCR was performed with Pwo DNA Polymerase (Boehringer; initial denaturation at 94° C. for 3 min, 35 cycles of 940 for 50 s, 58° C. for 30 s, and 72° C. for 2 min with a time increment of 3 s per cycle for each extension step (72° C.), followed by a final extension step of 72° C. for 8 min). Primer sequences were (upstream primer: SEQ ID NO:41, downstream primer: SEQ ID NO:42 with NotI-linkers underlined). PCR products were gel purified, incubated with NotI, and cloned into the expression vector pcDNA3.1 (Invitrogen). Four different PCR products were sequenced to control for potential PCR-induced sequence errors. Cells were simultaneously cotransfected with a reporter vector as described above. Chloride channel conductance activity was recorded after allowing the cells to recover for 24 hours.

The 2817 bp fragment of the hCLCA3 cDNA cloned into pcDNA3.1 was simultaneously transcribed and translated as described for the other CACC-AMs. Samples were analyzed by 10% SDS-PAGE (5 µl of a 25 µl reaction), followed by drying of the gel and exposure to film for 8 h. Protease protection assays were performed as described [10] to ascertain whether hCLCA3 translation products were translocated into the microsomes and thus entered the secretory pathway. In the presence of microsomal membranes in vitro translated and $^{35}$S-labeled wild type hCLCA3 was digested with Proteinase K (Sigma; 100 µg/ml) for 60 min on ice with or without detergent present (0.5% Nonidet-P 40). The reaction was stopped by adding phenylmethylsulfonyl fluoride and the products were analyzed by 10% SDS-PAGE and exposure to film. To allow for immunological detection of the translation products, three immunotagged cDNA clones were constructed (m1 to m3) by inserting a partial sequence of the human c-myc protein (EQKLISEEDL (SEQ ID NO:47)) [11] into the amino termini of the first (m1), the second (m2), or both (m3) ORFS. Generation of these constructs using overlap extension PCR and Pwo DNA polymerase (Boehringer) was as described [4]. Correct sequences of the constructs were verified by sequencing. Immunotagged DNA constructs were either in vitro translated as described above or transfected into 70% confluent human embryonic kidney (HEK) 293 or chinese hamster ovary (CHO) cells via the Lipofectamine Plus method (Life Technologies). Cell lysates were harvested after 48 h, resolved via 10% SDS-PAGE, and electroblotted onto nitrocellulose. Blots were probed with mouse-anti-human c-myc antibody 9E10 (1 µg/ml; Calbiochem) as primary antibody, horseradish peroxidase-conjugated goat anti-mouse antibody (0.2 µg/ml) as secondary antibody, and developed using enhanced chemiluminescence (Amersham). Secretion of the recombinant hCLCA3 protein into the culture supernatant was assayed by concentrating the conditioned medium (24 to 48 h after transfection) of HEK 293 or CHO cells transfected with construct m3 using ultrafiltration devices with a molecular cutoff at 10 kDa (Ultrafree-15, Biomax-10 filter; Millipore; centrifugation at 2,000 g for 30 min at 4° C.).

EXAMPLE 6

This embodiment demonstrates that the CACC-AMs of the present invention can function as adhesion molecules. As an illustration, a recombinant Lu-ECAM-1, encoded by a nucleic acid molecule according to the present invention, has unexpectedly improved biological activity. Recombinant (r) Lu-ECAM-1 and wild type (wt) Lu-ECAM-1 were compared in their adhesion ability to lung-metastatic B16-F10 melanoma cells. Using anti-Lu-ECAM-1 mAb 6D3, wtLu-ECAM-1 was purified from extracts of bovine aortic endothelial cells, and rLu-ECAM-1 was purified from extracts of transfected HEK293 cells. The tumor cell adhesion assay was performed as described previously (Zhu et al., 1992, supra). Briefly, 100 µg/ml in phosphate buffered saline of either wtLu-ECAM-1 or rLu-ECAM-1 was used to coat wells of 96 plates overnight at 4° C. Wells were then washed with tissue culture medium, and each well is seeded with a suspension of tissue culture medium and $2\times10^4$ tumor cells which had been radio-labelled. After being spun onto the coated wells at 15 g for 1 minute, and incubated for 10 minutes at 37° C., nonadherent tumor cells were spun off at 150 g for 5 minutes. Adherent tumor cells were then dissolved in 1% SDS and counted in a liquid scintillation counter. Tumor cell attachment is recorded as the percent cells bound of the total cells seeded. Inhibition of tumor cell adhesion is determined by first incubating the Lu-ECAM-1 coated wells with mAb 6D3 (1 µg/ml) for 1 hour at room temperature before the tumor cells are added.

Figure 5:
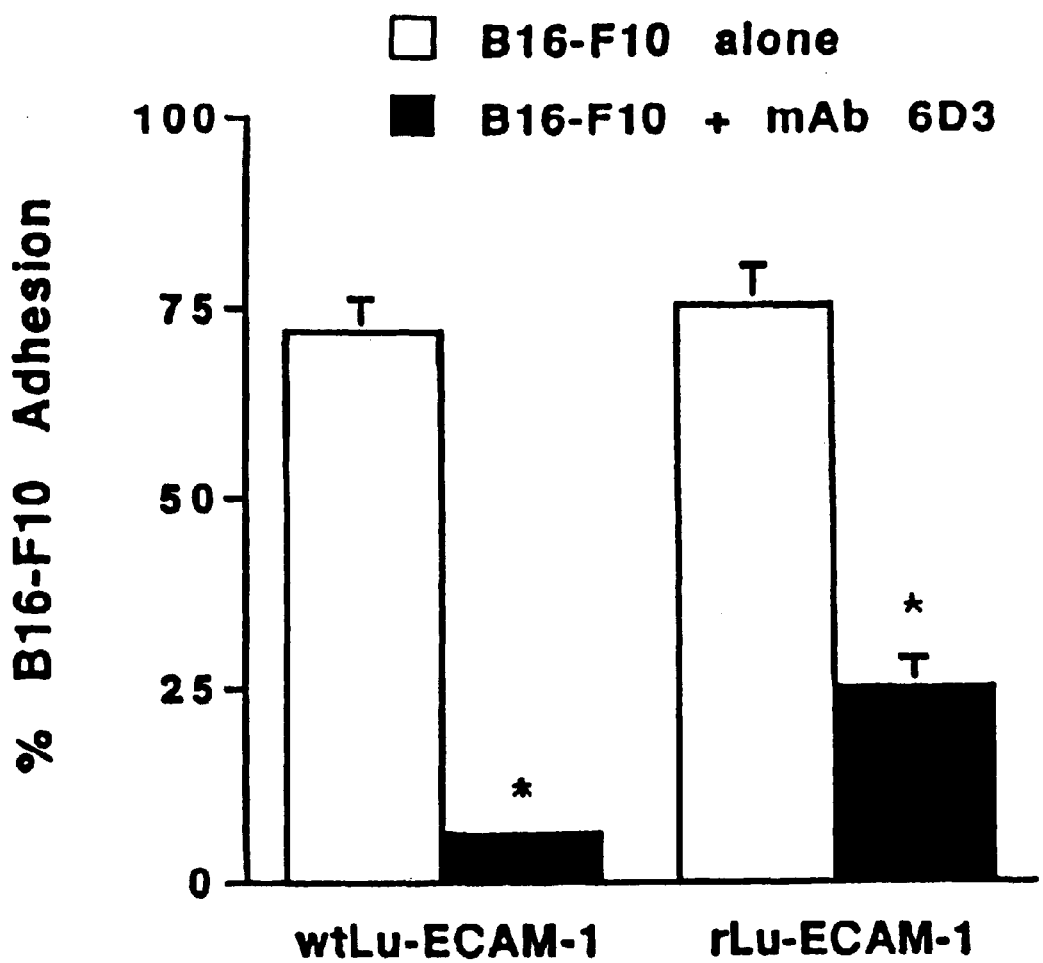
FIG. 5 is a bar graph illustrating lung-metastatic tumor cell adhesion to wild type Lu-ECAM-1 in the presence or absence of anti-Lu-ECAM-1 mAb 6D3; and lung-metastatic tumor cell adhesion to recombinant Lu-ECAM-1 in the presence or absence of anti-Lu-ECAM-1 mAb 6D3.

As shown in FIG. 5, recombinant Lu-ECAM-1 has unexpectedly improved biological activity (e.g., adhesive function to lung-metastatic tumor cells) as compared to wild type Lu-ECAM-1. More particularly, rLu-ECAM-1 supported adhesion of 87% of lung-metastatic tumor cells, whereas wtLu-ECAM-1 supported adhesion of only 43% of lung-metastatic tumor cells. Lung-metastatic tumor cell adhesion to wtLu-ECAM-1 was almost completely blocked by anti-Lu-ECAM-1 mAb 6D3, whereas lung-metastatic tumor cell adhesion to rLu-ECAM-1 was only partially inhibited (66%) by the concentration of anti-Lu-ECAM-1 mAb 6D3 used.

EXAMPLE 7

Figure 9:
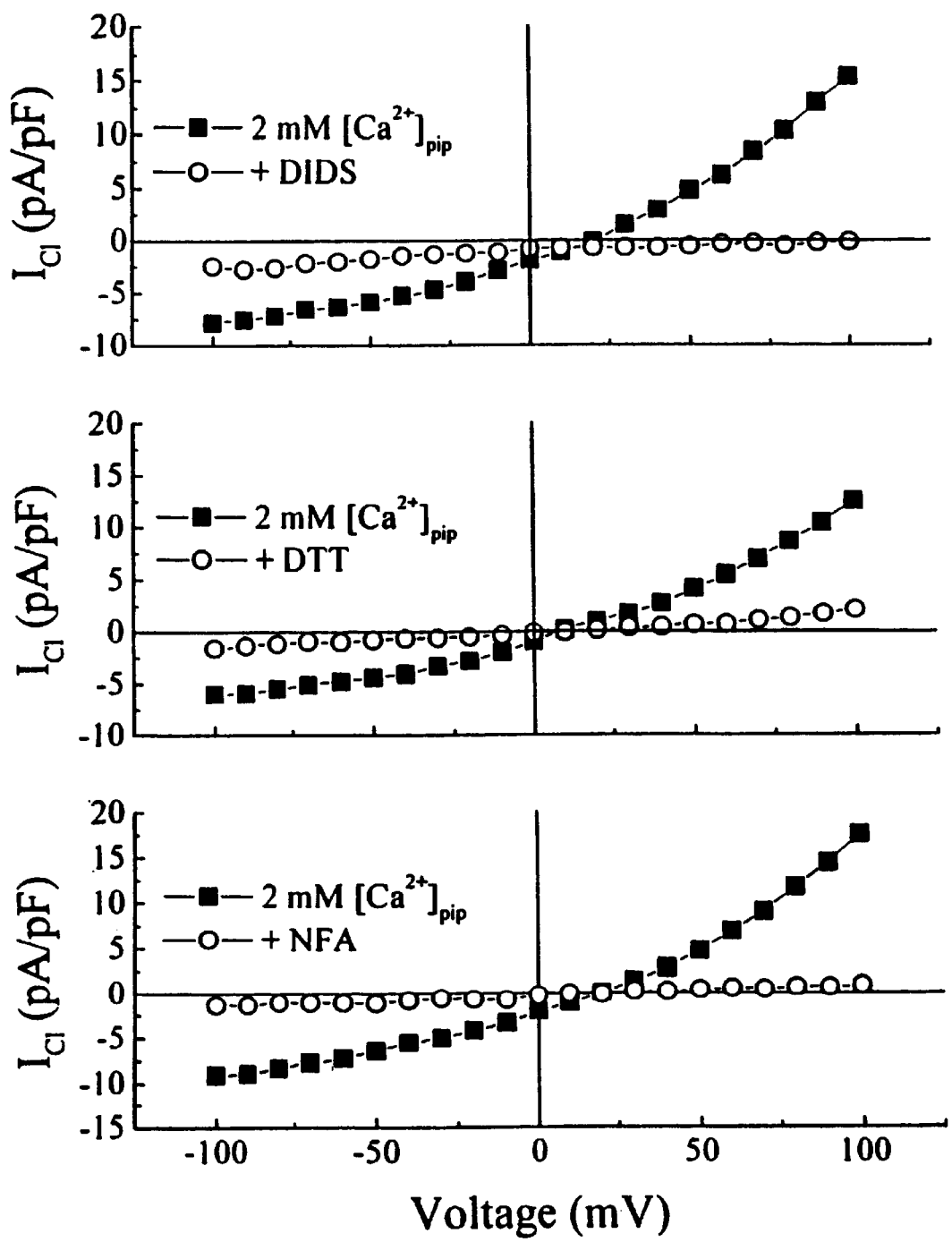
FIG. 9 is a representation of whole cell currents in mCLCA1-transfected HEK293 cells.

A comparison of the amino acid sequence of the CACC-AMs of the present invention is shown in FIG. 9. Sequence alignment and homology searches were carried out by using standard commercial software. For example, BLAST program was used for homology searches in existing data bases, and Megalign of the DNAStar package (Lasergene) was used for multiple sequence alignment. The sequence alignment of the four CACC-AMs of the present invention and the bovine CLCA (Cunningham et al. supra) indicates conservation throughout the entire length of the sequence, without the compartmentalization of more conserved domains. No significant homologies to any other chloride channel proteins were detected.

Table 1 illustrates a comparison of the size of the various mammalian Lu-ECAM-1 proteins and Lu-ECAM-1 associated proteins as encoded by the respective open reading frames.

TABLE 1

| Species | SEQ ID NO: | Total # of Amino Acids | Predicted Size |
|---|---|---|---|
| bovine | 2 and 3 | 905 a.a. | 90 kD, 32–28 kD |
| human hCLCA1 | 28 | 914 a.a. | 90 kD, 40 kD |
| human hCLCA3 | 30 | 1000 a.a. | 130 kD processing not known) |
| human hCLCA2 | 32 | 943 a.a. | 130 kD processing not known) |
| murine mCLCA | 34 | 902 a.a. | 130 kD, 125 kD, 90 kD, 32–38 kD |

Table 2 is a comparison among the mammalian Lu-ECAM-1 family showing both an approximated amino acid similarity and an approximated amino acid identity (expressed as "similarity/identity").

TABLE 2

|  | bovine (SEQ ID NOs: 2&3) | murine (SEQ ID NO: 34) | human (SEQ ID NO: 28) | human (SEQ ID NO: 30) | human (SEQ ID NO: 32) |
|---|---|---|---|---|---|
| bovine (SEQ ID NOs: 2&3) | 100/100 | 81.3/ 70.8 | 67.4/ 52.4 | 85.7/ 77.4 | 63.7/ 49.8 |
| murine mCLCA (SEQ ID NO: 34) | — | 100/100 | 67.5/ 52.7 | 80.9/ 69.5 | 62.8/ 48.4 |
| human hCLCA1 (SEQ ID NO: 28) | — | — | 100/100 | 65.3/ 51.4 | 62.3/ 44.7 |
| human hCLCA3 (SEQ ID NO: 30) | — | — | — | 100/100 | 62.1/ 48.2 |
| human hCLCA2 (SEQ ID NO: 32) | — | — | — | — | 100/100 |

Table 3 is a comparison among the mammalian Lu-ECAM-1 gene family showing approximated nucleic acid similarities (expressed in %).

TABLE 3

|  | bovine (SEQ ID NO: 1) | murine (SEQ ID NO: 33) | human (SEQ ID NO: 27) | human (SEQ ID NO: 29) | human (SEQ ID NO: 31) |
|---|---|---|---|---|---|
| bovine (SEQ ID NO: 1) | 100 | 76.7 | 63.1 | 85.9 | 64.4 |
| murine (SEQ ID NO: 33) | — | 100 | 62.6 | 76.1 | 61.2 |
| human (SEQ ID NO: 27) | — | — | 100 | 63.3 | 58.9 |
| human (SEQ ID NO: 29) | — | — | — | 100 | 62.6 |
| human (SEQ ID NO: 31) | — | — | — | — | 100 |

EXAMPLE 8

This embodiment illustrates that the full length cDNAs of the present invention encode calcium sensitive chloride channels. The various cDNAS were used for transfection of a cell line. For electrophysiological studies, cells were also cotransfected with a reporter vector (pEGFP, CLONTECH). Cotransfection with a reporter vector allows for easy identification of transfected cells by visualization under a fluorescent microscope. Whole cell recording was then carried out in the transfected cells to determine the presence of calcium sensitive chloride channels.

Transfected cells were used for electrophysiological recording. Cells were superfused with a bath solution containing 112 mM NMDG-Cl, 30 mM sucrose, 1 mM EGTA, 0.366 mM $CaCl_2$, 2 mM $MgCl_2$, 5 mM N-2-hydroxyxyethanylpiperazine-N-2-ethanesulfonic acid. Whole cell channel activity was recorded in transfected cells by using borosilicate glass electrodes (tip resistance 4–9 M ohms) filled with the bath solution. Recordings were carried out in the presence or absence of a calcium channel inhibitors (DIDS, niflumic acid and DTT). To determine the effect of ionomycin on channel activity, electrodes filled with standard bath solution containing either 5 mM ATP and 1 mM EGTA in the presence of low intracellular calcium. After gigaohm seal formation, cells were clamped at +20 mV. Whole cell currents were recorded at room temperature, sampled at 5–10 kHz and filtered at 1–2 kHz. The I-V relationship was determined using 300 ms voltage steps from a holding potential of +20 mV to potentials from –100 to +100 mV at 10 mV intervals. To normalize measured membrane currents to membrane currents to membrane capacitance, the capacitive current transient recorded in response to a 10 mV hyperpolarizing pulse was integrated and divided by the given voltage to give total membrane capacitance ($C_m$) for each cell.

Figure 10:
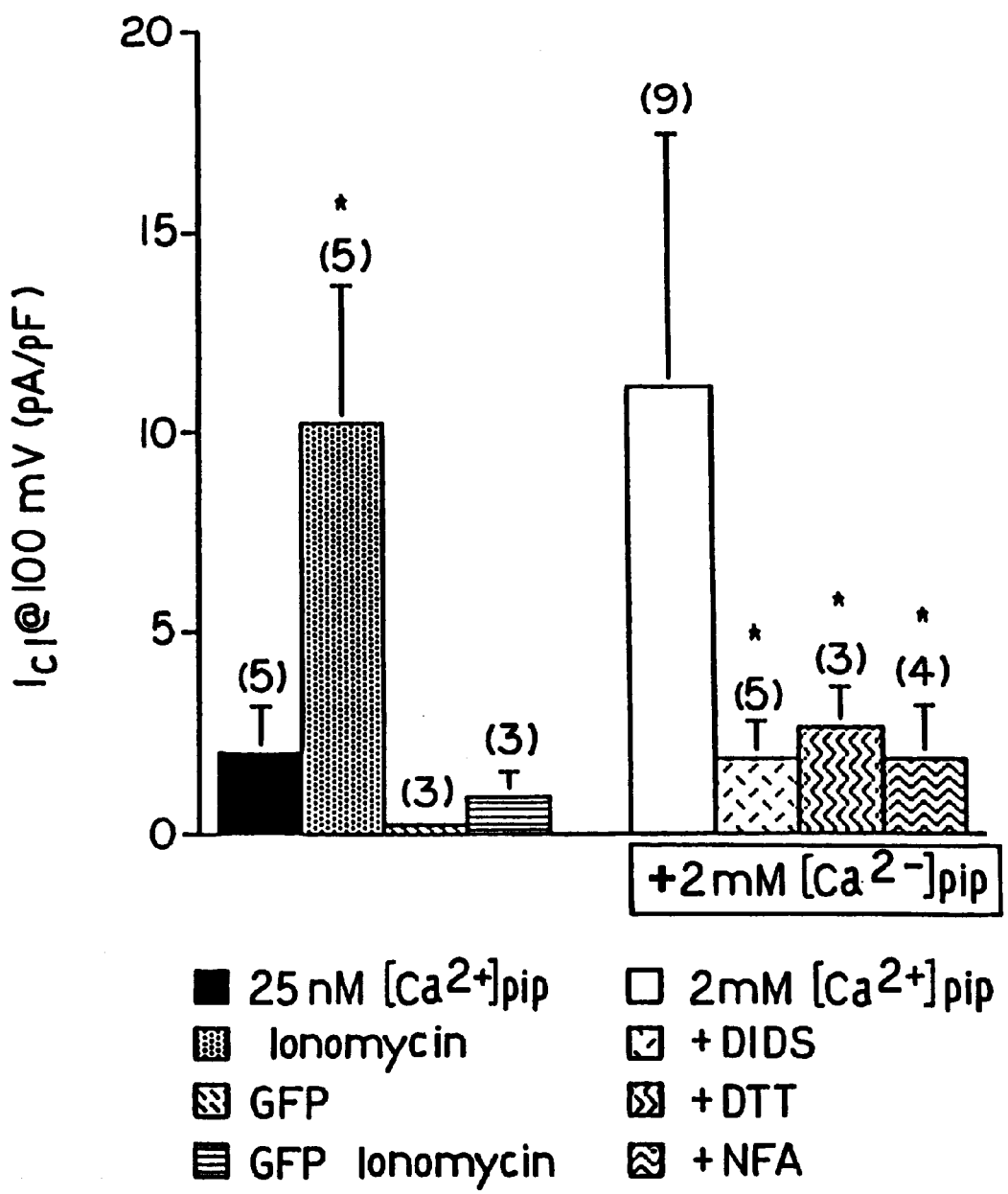
FIG. 10 is an illustration of the summary the effects of inhibitors on mCLCA1 current expression.

As shown in FIG. 9, expression of mCLCA1 in HEK293 cells was associated with the appearance of a novel $Ca^{2+}$ sensitive Cl-channel as determined by whole cell recordings in the presence and absence of the $Ca^{2+}$ ionophore ionomycin (2 uM). As shown in FIG. 9b, at low intracellular free Ca2+ concentrations, the basal current at +100 mV in mCLCA1-transfected cells was 2.05±1.09 pA/pF. With ionomycin the current increased to 10.23±3.46 pA/pF. No significant effect of these manipulations was seen in non-transfected or control-transfected cells. Basal currents in the presence of 2 mM Ca2+ in transfected cells averaged 12.01±6.31 pA/pF. Perfusion of 300 uM DIDS reduced the current to 1.84±0.96. A similar effect was seen with NFA and DTT. These results indicate that the expression of mCLCA1 in HEK293 cells is associated with the appearance of a Ca2+ sensitive chloride conductance. Under whole cell conditions, the current was outwardly rectified and inhibited by the anion channel blockers DIDS and NFA as well as the reducing agent DTT. This data is summarized in FIG. 10.

Figure 11:
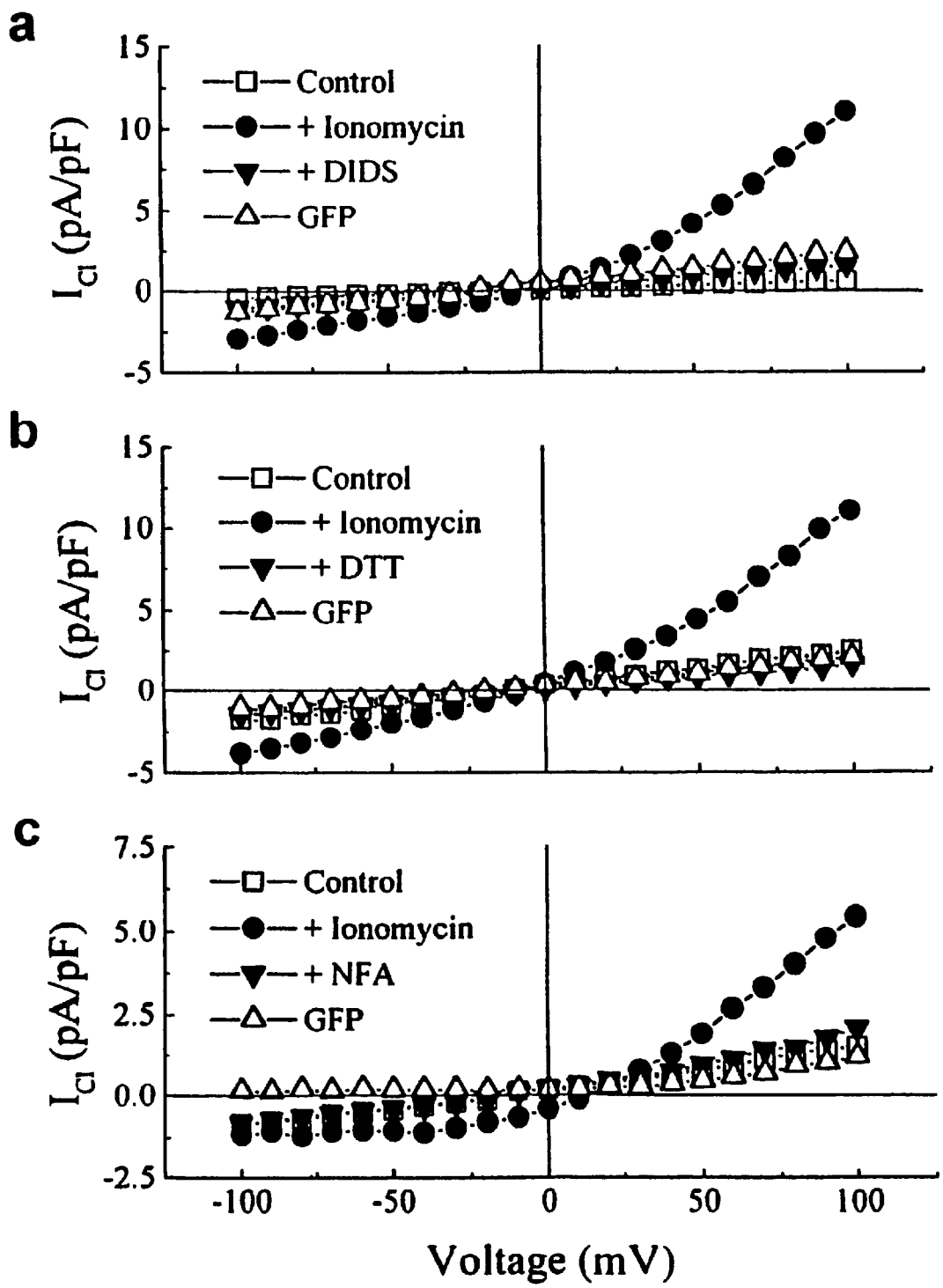
FIG. 11 is a representation of whole cell currents in hCLCA1-transfected HEK293 cells.
Figure 12:
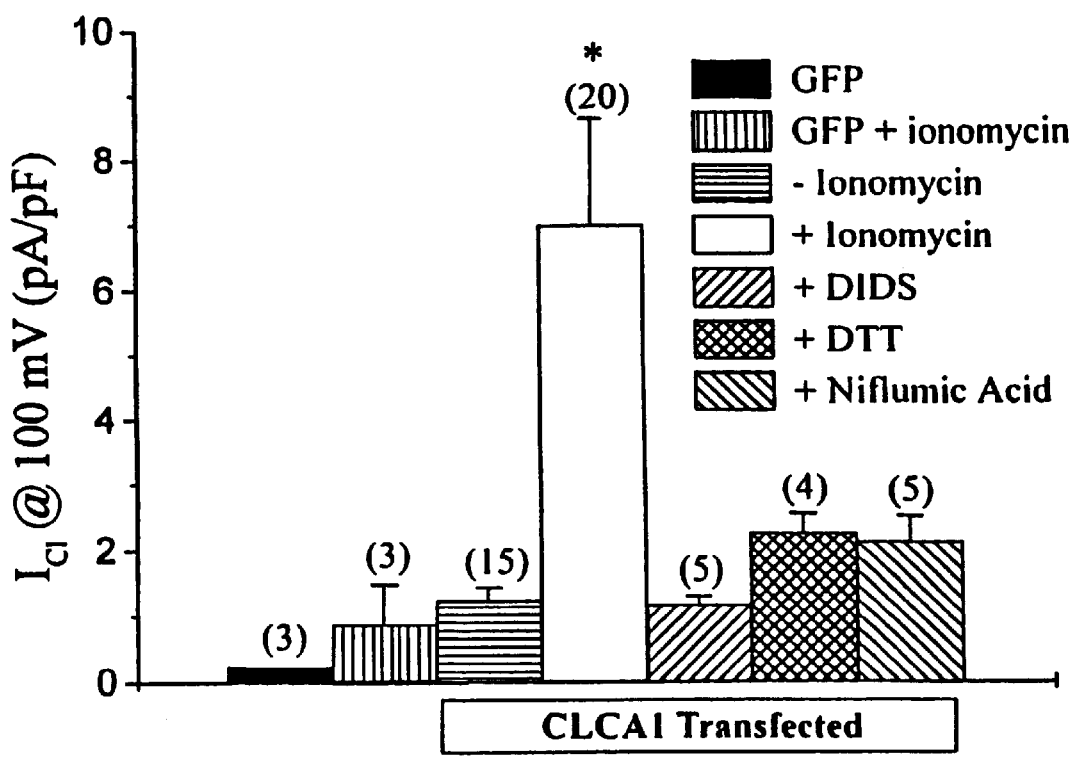
FIG. 12 is an illustration of the summary the effects of inhibitors on hCLCA1 current expression.

Whole cell recording of cells transfected with hCLCA1 cDNA demonstrated the induction of calcium sensitive chloride channels (FIG. 11). External perfusion of ionomycin (2 uM) was associated with an increase in the maximally activated current at +100 mV from 0.65 to 11.06 pA/pF. The current voltage relationship was outwardly rectified and reversed at 0 mV under symmetrical recording conditions. No effect of ionomycin was observed on non-transfected cells or control transfected cells. Addition of DIDS, DTT or niflumic acid reduced the currents to 1.63, 1.67 and 2.07 pA/pF respectively Cell attached patch recordings of single channels confirmed the presence of calcium sensitive anion channel (data not shown). This data is summarized in FIG. 12.

Figure 13A:
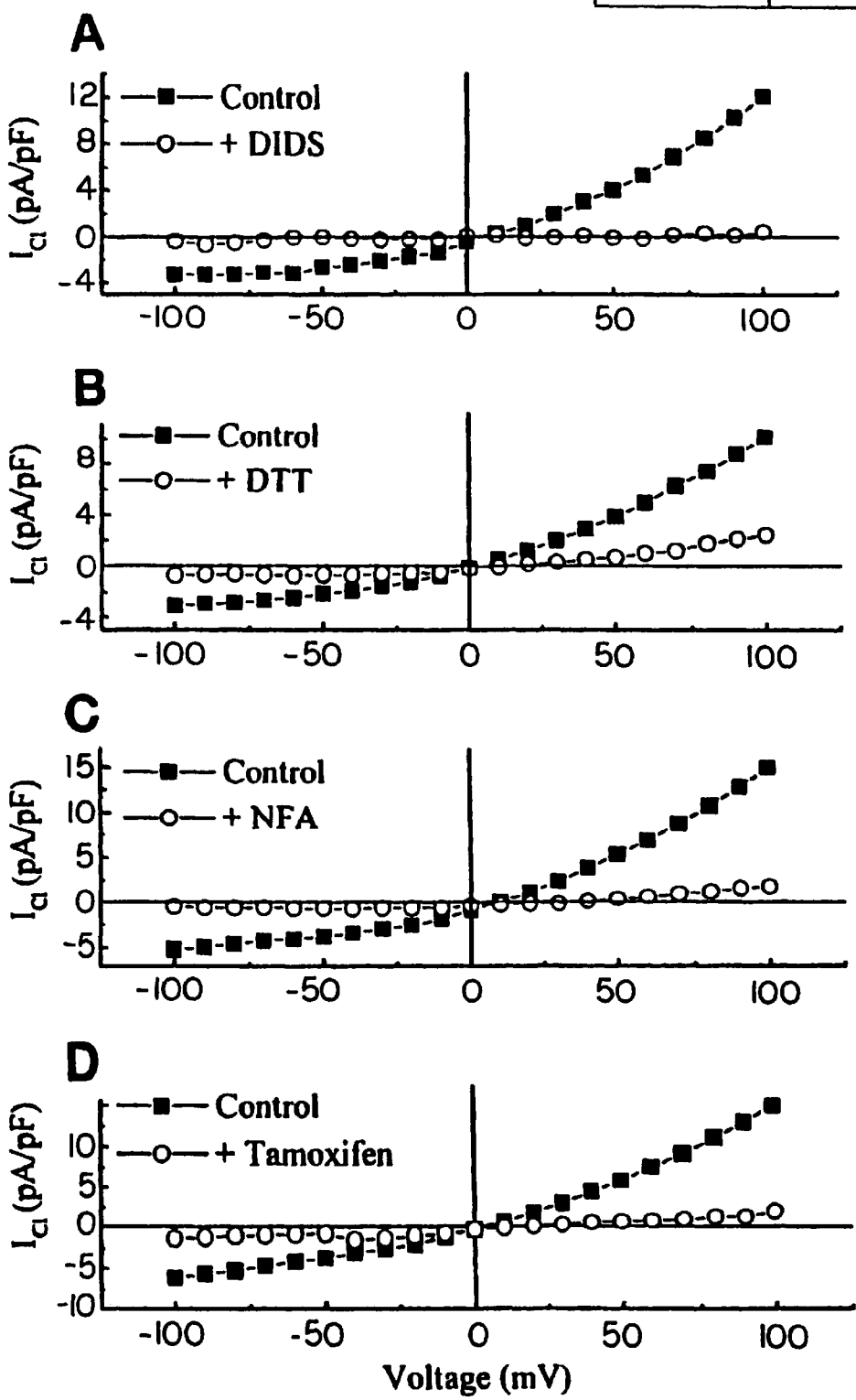
FIG. 13 is an illustration of the electrohpysiological analysis of hCLCA2.
Figure 13B:
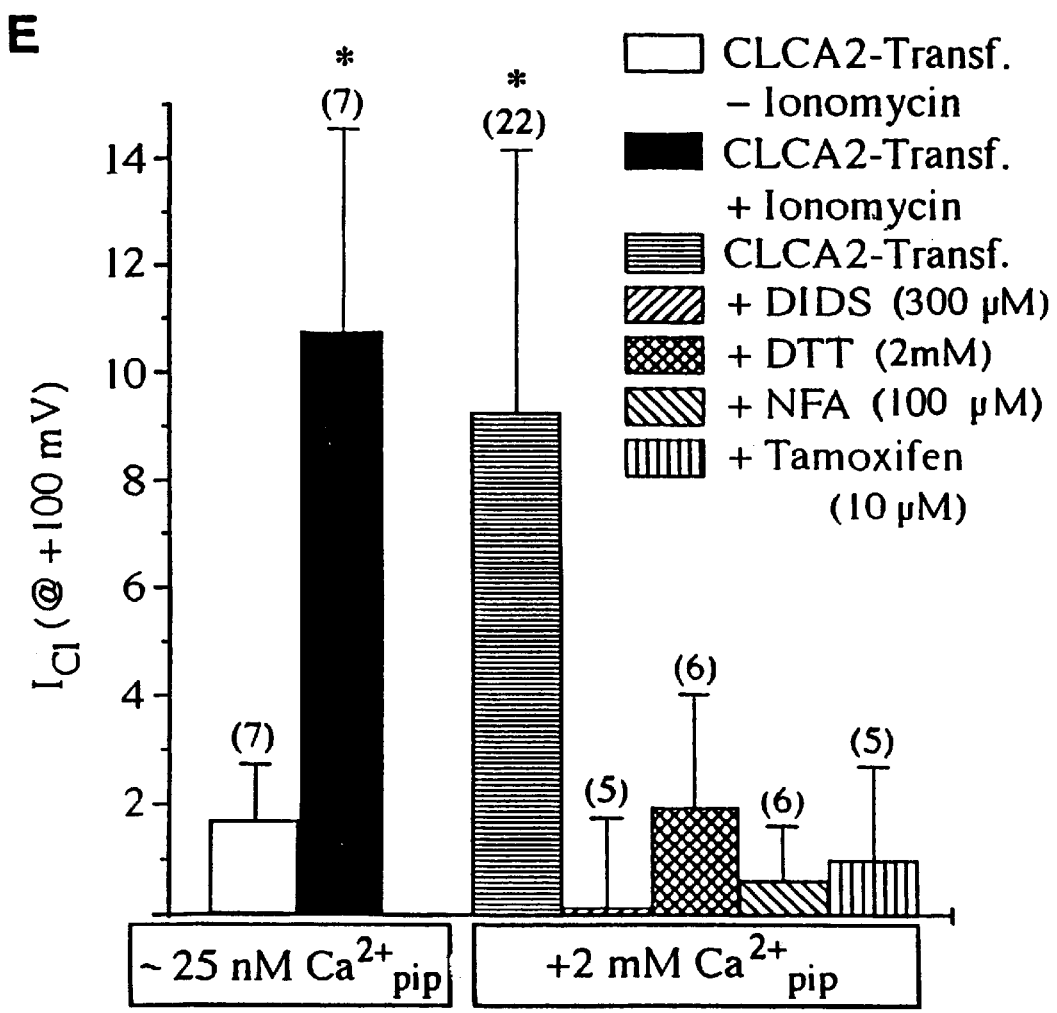

Whole cell recordings of hCLCA2 transfected HEK293 cells exhibited s slightly outwardly rectifying current/voltage relationship that was absent from control cells (transfected with vector alone; FIG. 13). This current was sensitive to DIDS (300 uM), DTT (2 mM), niflumic acid (100 uM), and tamoxifen (10 uM). When the pipet solution contained low Ca2= (about 25 nM) with 2 mM Ca2+ in the bath, perfusion of the Ca2+ ionophore ionomycin (4 uM) through the bath also activated the current (FIG. 13e).

These results indicate that the expression of CACC/AM molecules disclosed herein and their variants is associated with the appearance of calcium sensitive chloride channels.

EXAMPLE 9

This embodiment illustrates uses of the sequences according to the present invention. In one embodiment of the present invention, an individual having a primary tumor having lung-metastatic capabilities is treated with an anti-adhesion therapy comprising administering to the individual a therapeutically effective amount of a composition comprising either antibody raised to rLu-ECAM-1 or recombinant Lu-ECAM-1 complex, or a vector for expressing a soluble form of rLu-ECAM-1 or rLu-ECAM-1 complex which can then bind to the lung-metastatic tumor cells. Either composition may function to prevent lung-metastatic tumor cell adhesion to the lung venule endothelial cells, thereby preventing colonization by the metastatic tumor cells. As known to those skilled in the art, an effective amount of a therapeutic composition may depend on the route of administration (e.g., intravenous or other route known in the art), and physiological factors including the age, size, and rate of metabolism of the individual to be treated.

Another embodiment of the present invention is a method for providing calcium-dependent chloride conductance channels to mammalian cells. Recombinant Lu-ECAM-1 or rLu-ECAM-1 complex may form a chloride channel which may affect chloride secretion, and hence fluid secretion, from the cell. It may be that the chloride ion channel is coupled to the adhesion process involving the binding of Lu-ECAM-1 to a ligand, as similarly observed for the adherence and growth of lymphatic endothelial cells (Martin et al., 1996, supra). Thus, in mammalian cells in which the membrane chloride ion channels are deficient in number or function (e.g., in airway epithelial cells of cystic fibrosis patients), a method of providing to mammalian cells a calcium-dependent chloride conductance channel, rLu-ECAM-1 or rLu-ECAM-1 complex, comprises administering directly to the lung endothelial and/or epithelial cells (in vitro or in vivo) an expression vector. The expression vector contains a nucleic acid molecule (or a variant thereof) operably linked to expression control sequences, wherein the nucleic acid molecule encodes either rLu-ECAM-1 or rLu-ECAM-1 complex, with the resultant expression vector being introduced into the mammalian cell, and a functional calcium-dependent chloride conductance channel produced in the mammalian cells which contain the expression vector. The cells targeted for chloride cunductance channel production may include airway cells selected from the group consisting of tracheal, bronchial or lung cells. If the cells are transfected in vitro, the transfected cells may then be introduced in vivo into the area of the lungs of the individual which is deficient in chloride channel function.

Having described the preferred embodiments of the present invention, it will be apparent to one of ordinary skill in the art that various modifications may be made to the disclosed embodiments, and that such modifications are intended to be within the scope of the present invention.

We claim:

1. An isolated nucleic acid molecule comprising a nucleotide sequence encoding a protein having an amino acid sequence of SEQ ID NO:32.

2. A vector comprising the nucleic acid molecule of claim 1.

3. A recombinant vector containing the nucleic acid molecule according to claim 1, wherein the nucleic acid molecule is operatively linked to one or more control elements.

4. A host cell containing the vector of claim 3.

5. A method of providing calcium activated chloride channel activity to a mammalian cell comprising transfecting the mammalian cell with the vector of claim 3.

6. An isolated and purified polypeptide comprising the amino acid sequence of SEQ ID NO:32.

7. An isolated nucleic acid molecule comprising a nucleotide sequence of SEQ ID NO:31.

* * * * *

UNITED STATES PATENT AND TRADEMARK OFFICE
CERTIFICATE OF CORRECTION

PATENT NO. : 6,309,857 B1
DATED : October 30, 2001
INVENTOR(S) : Pauli et al.

Page 1 of 1

It is certified that error appears in the above-identified patent and that said Letters Patent is hereby corrected as shown below:

<u>Title page,</u>
Inventors, the first named inventor should be -- Bendicht U. Pauli --

Signed and Sealed this

Twenty-sixth Day of March, 2002

Attest:

JAMES E. ROGAN
*Attesting Officer*   *Director of the United States Patent and Trademark Office*